US010493281B2

(12) United States Patent
Giftakis et al.

(10) Patent No.: US 10,493,281 B2
(45) Date of Patent: Dec. 3, 2019

(54) TIMING THERAPY EVALUATION TRIALS

(75) Inventors: Jonathon E. Giftakis, Maple Grove, MN (US); Mark T. Rise, Monticello, MN (US); Paul H. Stypulkowski, North Oaks, MN (US); Timothy J. Denison, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1503 days.

(21) Appl. No.: 12/425,922

(22) Filed: Apr. 17, 2009

(65) Prior Publication Data
US 2009/0264967 A1 Oct. 22, 2009

Related U.S. Application Data

(60) Provisional application No. 61/046,200, filed on Apr. 18, 2008.

(51) Int. Cl.
*A61N 1/00* (2006.01)
*A61N 1/36* (2006.01)
(Continued)

(52) U.S. Cl.
CPC ..... *A61N 1/36135* (2013.01); *A61N 1/36082* (2013.01); *A61N 1/0534* (2013.01); *A61N 1/37211* (2013.01); *A61N 1/37247* (2013.01)

(58) Field of Classification Search
CPC .... A61N 1/36; A61N 1/3605; A61N 1/37247; A61N 1/37211; A61N 1/36082; A61N 1/36135; A61N 1/0534
(Continued)

(56) References Cited

U.S. PATENT DOCUMENTS 6,066,163 A 5/2000 John
6,263,237 B1 7/2001 Rise
(Continued)

FOREIGN PATENT DOCUMENTS

WO 01/76469 A2 10/2001
WO 03/035165 A1 5/2003
(Continued)

OTHER PUBLICATIONS

International Search Report and Written Opinion of international application No. PCT/US2009/041005, dated Oct. 29, 2009, 12 pp.
(Continued)

*Primary Examiner* — Lindsey G Wehrheim
(74) *Attorney, Agent, or Firm* — Shumaker & Sieffert, P.A.

(57) ABSTRACT

A characteristic of a washout period following the delivery of therapy to a patient according to a therapy program may be determined based on a physiological parameter of the patient. A washout period includes the period of time during which a carryover effect from the therapy delivery dissipates. Monitoring a washout period may be useful for timing the delivery of therapy according to different therapy programs during a therapy evaluation period. For example, at least one physiological signal of the patient may be monitored to automatically determine when a washout period has ended, e.g., when stimulation and carryover effects of therapy delivery according to a first therapy program have substantially dissipated, in order to determine when therapy delivery according to a second therapy program can be initiated.

41 Claims, 22 Drawing Sheets

(51) Int. Cl.
*A61N 1/05* (2006.01)
*A61N 1/372* (2006.01)

(58) Field of Classification Search
USPC .............. 607/2–26, 30–32, 45, 46, 61, 62,
607/115–148
See application file for complete search history.

(56) References Cited

U.S. PATENT DOCUMENTS

| | | | |
|---|---|---|---|
| 6,371,922 B1* | 4/2002 | Baumann et al. | 600/485 |
| 6,463,328 B1 | 10/2002 | John | |
| 6,490,486 B1 | 12/2002 | Bradley | |
| 6,622,036 B1 | 9/2003 | Suffin | |
| 6,708,064 B2 | 3/2004 | Rezai | |
| 7,231,245 B2 | 6/2007 | Greenwald et al. | |
| 7,277,758 B2 | 10/2007 | DiLorenzo | |
| 7,313,440 B2 | 12/2007 | Miesel | |
| 7,353,064 B2 | 4/2008 | Gliner et al. | |
| 7,353,065 B2 | 4/2008 | Morrell | |
| 7,418,290 B2 | 8/2008 | Devlin et al. | |
| 7,706,871 B2 | 4/2010 | Devlin et al. | |
| 8,116,874 B2 | 2/2012 | Tass | |
| 2001/0031993 A1 | 10/2001 | Salo et al. | |
| 2002/0013612 A1 | 1/2002 | Whitehurst | |
| 2002/0072770 A1* | 6/2002 | Pless | 607/2 |
| 2003/0074032 A1* | 4/2003 | Gliner | 607/45 |
| 2004/0093983 A1 | 5/2004 | Mishima et al. | |
| 2004/0111127 A1 | 6/2004 | Gliner | |
| 2004/0133248 A1* | 7/2004 | Frei et al. | 607/45 |
| 2004/0215286 A1 | 10/2004 | Stypulkowski | |
| 2004/0249422 A1 | 12/2004 | Gliner et al. | |
| 2005/0033379 A1 | 2/2005 | Lozano et al. | |
| 2005/0043774 A1 | 2/2005 | Devlin et al. | |
| 2005/0081847 A1 | 4/2005 | Lee et al. | |
| 2005/0209513 A1 | 9/2005 | Heruth et al. | |
| 2005/0216064 A1 | 9/2005 | Heruth et al. | |
| 2005/0216071 A1 | 9/2005 | Devlin et al. | |
| 2006/0058627 A1 | 3/2006 | Flaherty et al. | |
| 2006/0190051 A1* | 8/2006 | Gerber et al. | 607/41 |
| 2007/0005115 A1 | 1/2007 | Lozano et al. | |
| 2007/0123758 A1 | 5/2007 | Miesel et al. | |
| 2007/0129769 A1 | 6/2007 | Bourget et al. | |
| 2007/0150024 A1 | 6/2007 | Leyde et al. | |
| 2007/0173901 A1 | 7/2007 | Reeve | |
| 2007/0173902 A1 | 7/2007 | Maschino et al. | |
| 2007/0265536 A1 | 11/2007 | Giftakis et al. | |
| 2007/0293901 A1 | 12/2007 | Rousso et al. | |
| 2008/0027487 A1 | 1/2008 | Patel et al. | |
| 2008/0033502 A1 | 2/2008 | Harris et al. | |
| 2008/0221401 A1 | 9/2008 | Derchak et al. | |
| 2008/0269631 A1 | 10/2008 | Denison et al. | |
| 2008/0319511 A1 | 12/2008 | Pless | |

FOREIGN PATENT DOCUMENTS

| | | |
|---|---|---|
| WO | 2006/063558 A1 | 6/2006 |
| WO | 2007/048087 A2 | 4/2007 |
| WO | 2007/050780 A2 | 5/2007 |
| WO | WO 2008/013722 A1 | 1/2008 |

OTHER PUBLICATIONS

Erwin B. Montgomery, Jr., M.D, "Deep Brain Stimulation Programming," Feb. 20, 2006, 37 pages.

Patent Application Entitled "Psychiatric Disorder Therapy Control," U.S. Appl. No. 12/425,903, filed Apr. 17, 2009.

Patent Application Entitled "Analyzing a Washout Period Characteristic for Psychiatric Disorder Therapy Delivery," U.S. Appl. No. 12/426,065, filed Apr. 17, 2009.

Patent Application Entitled "Analyzing a Stimulation Period Characteristic for Psychiatric Disorder Therapy Delivery," U.S. Appl. No. 12/425,859, filed Apr. 17, 2009.

Notifiation Concerning Transmittal of International Preliminary Report on Patentability for corresponding patent application No. PCT/US2009/041005, dated Oct. 28, 2010, 10 pages.

Jun. J. Pilcher and Allen I. Huffcutt, "Effects of Sleep Deprivation on Performance: A Meta-Analysis," 1996, Sleep, vol. 19, Issue 04, pp. 318-326.

Response to European Office Action dated Feb. 25, 2014, from counterpart European Patent Application No. 09733103.7, filed on Jun. 26, 2014, 6 pp.

European Office Action from counterpart European Application No. 09 733 103.7-1657, dated Feb. 25, 2014, 7 pp.

Decision on Appeal from U.S. Appl. No. 12/425,903, dated Oct. 26, 2015, 14 pp.

Response to Decision on Appeal dated Oct. 26, 2015, from U.S. Appl. No. 12/425,903, filed Dec. 21, 2015, 11 pp.

* cited by examiner

US 10,493,281 B2

TIMING THERAPY EVALUATION TRIALS

This application claims the benefit of U.S. Provisional Application No. 61/046,200 to Giftakis et al., entitled, "TIMING THERAPY EVALUATION TRIALS" and filed on Apr. 18, 2008, the entire content of which is incorporated herein by reference.

TECHNICAL FIELD

The disclosure relates to medical devices, and, more particularly, to configuration of therapy parameters.

BACKGROUND

Implantable medical devices, such as electrical stimulators or therapeutic agent delivery devices, may be used in different therapeutic applications, such as deep brain stimulation (DBS), spinal cord stimulation (SCS), pelvic stimulation, gastric stimulation, peripheral nerve stimulation, functional electrical stimulation or delivery of pharmaceutical agent, insulin, pain relieving agent or anti-inflammatory agent to a target tissue site within a patient. A medical device may be used to deliver therapy to a patient to treat a variety of symptoms or patient conditions such as chronic pain, tremor, Parkinson's disease, other types of movement disorders, seizure disorders (e.g., epilepsy), urinary or fecal incontinence, sexual dysfunction, obesity, mood disorders, gastroparesis or diabetes. In some therapy systems, an implantable electrical stimulator delivers electrical therapy to a target tissue site within a patient with the aid of one or more electrodes, which may be deployed by medical leads. In addition to or instead of electrical stimulation therapy, a medical device may deliver a therapeutic agent to a target tissue site within a patient with the aid of one or more fluid delivery elements, such as a catheter or a therapeutic agent eluting patch.

During a programming session, which may occur during implant of the medical device, during a trial session, or during a follow-up session after the medical device is implanted in the patient, a clinician may generate one or more therapy programs that provide efficacious therapy to the patient, where each therapy program may define values for a set of therapy parameters. A medical device may deliver therapy to a patient according to one or more stored therapy programs. In the case of electrical stimulation, the therapy parameters may define characteristics of the electrical stimulation waveform to be delivered. Where electrical stimulation is delivered in the form of electrical pulses, for example, the parameters may include an electrode combination, an amplitude, which may be a current or voltage amplitude, a pulse width, and a pulse rate for the pulses. In the case of a therapeutic agent delivery device, the therapy parameters may include a dose (e.g., a bolus or a group of boluses) size, a frequency of bolus delivery, a concentration of a therapeutic agent in the bolus, a type of therapeutic agent to be delivered to the patient (if the medical device is configured to deliver more than one type of agent), a lock-out interval, and so forth.

SUMMARY

In general, the disclosure is directed to devices, systems, and methods for automatically determining at least one characteristic of a washout period following delivery of therapy to a patient. A washout period includes the period of time following delivery of therapy to a patient during which at least one carryover effect from the therapy dissipates. In the case of electrical stimulation therapy, the carryover effect generally refers to a physiological effect generated in response to the delivery of an electrical stimulation signal, where the effect persists after termination of the stimulation signal. Accordingly, at the end of the washout period, one or more physiological effects from the delivery of electrical stimulation therapy to the patient are substantially absent. Carryover effects from delivery of therapy may be automatically determined based on one or more physiological parameters of the patient, which may be monitored during the delivery of therapy and after the cessation of therapy delivery (i.e., the "post-stimulation" period). The physiological parameters may include, for example, at least one of brain activity (e.g., electroencephalogram or electrocorticogram), a heart rate, respiratory rate, electrodermal activity, facial electromyogram or thermal activity of the patient's body.

In some embodiments, at least one characteristic of a washout period is automatically determined for a plurality of therapy programs based on at least one physiological parameter of the patient. A therapy program defines respective values for a set of therapy parameters. In the case of electrical stimulation therapy, the therapy parameters may include voltage or current amplitude and frequency of the electrical signals, and, in the case of electrical pulses, the pulse width, pulse rate, and duty cycle of the pulses. A signal indicative of the physiological parameter (i.e., a physiological signal) may be monitored before, during, and after the delivery of therapy according to a particular therapy program. In response to the delivery of therapy, the physiological signal may change. Thus, the change in the signal during the post-stimulation period may be monitored to determine a characteristic of the washout period, such as a duration of the washout period, an amplitude of the physiological signal waveform during the washout period, a trend in the physiological signal waveform during the washout period, a power level of the physiological signal measured in a particular frequency band of the physiological signal waveform, ratios of power levels between different frequency bands, and the like.

The washout period may be useful for timing trials of different therapy programs. For example, during a trial session in which therapy is delivered to the patient according to a plurality of therapy programs to determine an efficacious therapy program or range of acceptable therapy parameter values, it may be desirable to deliver test stimulation according to subsequent therapy programs after the stimulation and at least some carryover effects of the prior delivered therapy program have substantially dissipated. The stimulation effects occur while therapy is delivered. Accordingly, at least one physiological signal of the patient may be monitored to automatically determine when the stimulation and carryover effects of the prior delivered therapy have substantially dissipated, i.e., when the washout period of the prior delivered therapy has substantially ended.

In some embodiments, washout periods characteristics, alone or in addition to other metrics, may be useful for ordering (e.g., ranking) therapy programs. Other metrics for ordering therapy programs may include the type, severity or duration of side effects, an efficacy rating, and a power rating, e.g., the power required for the medical device to generate and deliver the therapy according to the therapy program.

The characteristics of at least one physiological signal of the patient during the washout period may be useful for assessing the efficacy of a therapy program, and, in some cases, adjusting at least one parameter value of the therapy program.

The characteristics of the one or more physiological signals during the washout period may also be useful for determining a patient mood state during the washout period. The patient mood state may be a symptom of a psychiatric disorder with which the patient is afflicted. For example, a particular waveform trend or waveform amplitude of the physiological signal may be associated with a particular patient mood state, such as an anxious state, a depressive state, and the like. Thus, the monitored signal during the washout period may be compared to a trend template or amplitude threshold value to determine the patient mood state. The probability of the mood state occurring during therapy delivery based on the therapy program may be determined based on the determined patient mood state associated with a therapy program.

A therapy system for managing a psychiatric disorder of the patient may be controlled based on a patient mood state that is determined based on a characteristic of a physiological signal. Therapy may be delivered to a patient according to a therapy program, and a physiological parameter of the patient may be monitored during or after therapy delivery in order to determine a patient mood state. In some embodiments, the therapy delivery is stopped prior to determining the patient mood state and the therapy delivery is restarted upon detecting a negative mood state. In other embodiments, therapy delivery is delivered until a positive mood state is detected, at which point the therapy delivery may be stopped.

In one embodiment, the disclosure is directed to a method comprising delivering therapy to a patient according to a therapy program during a first period, wherein the therapy program defines a value for at least one therapy parameter for managing a psychiatric condition (e.g., a psychiatric disorder) of the patient, monitoring a physiological signal of the patient during a second period following the first period, and automatically determining a characteristic of a washout period based on the monitored physiological signal, wherein the washout period occurs during the second period, and wherein at least one carryover effect from the therapy substantially dissipates during the washout period. The therapy may be electrical stimulation therapy or delivery of one or more therapeutic agents.

In another embodiment, the disclosure is directed to a method comprising delivering therapy to a patient according to a therapy program during a first period, monitoring a physiological signal of the patient during a second period following the first period, receiving information indicative of a patient mood state, wherein the patient mood state occurs during the second period, associating the patient mood state with at least one characteristic of the physiological signal during the second period.

In another embodiment, the disclosure is directed to a system comprising a sensor that generates a signal as a function of at least one physiological parameter of a patient, a medical device that delivers therapy to a patient according to a therapy program to manage a psychiatric condition during a first period, wherein the therapy program defines a value for at least one therapy parameter, and a processor that monitors the signal during a second period following the first period, and automatically determines a characteristic of a washout period for the therapy program based on the signal, wherein the washout period occurs during the second period, and wherein at least one carryover effect from the therapy substantially dissipates during the washout period.

In another embodiment, the disclosure is directed to a system comprising means for delivering therapy to a patient according to a therapy program during a first period, wherein the therapy program defines a value for at least one therapy parameter for managing a psychiatric condition of the patient, means for monitoring a physiological signal of the patient during a second period following the first period, and means for automatically determining a characteristic of a washout period based on the monitored physiological signal, wherein the washout period occurs during the second period, and wherein at least one carryover effect from the therapy substantially dissipates during the washout period.

In another embodiment, the disclosure is directed to a method comprising receiving a signal indicative of a physiological parameter of a patient during a first period during which therapy according to a first therapy program is delivered to the patient, detecting a carryover effect from the delivery of the therapy according to the first therapy program based on the signal, where the carryover effect occurs during a washout period following the first period, and automatically initiating delivery of therapy to the patient according to a second therapy program at a time based on the washout period.

In another embodiment, the disclosure is directed to a method comprising establishing a baseline state of a physiological signal of a patient, delivering electrical stimulation therapy to a patient according to a first therapy program during a stimulation period, monitoring the physiological signal of the patient during a post-stimulation period following the stimulation period, automatically determining when the physiological signal returns to first state that is based on the baseline state, and automatically delivering electrical stimulation therapy to the patient according to a second therapy program after the physiological signal returns to the baseline state.

In another embodiment, the disclosure is directed to a system comprising a sensor that generates a signal as a function of a physiological parameter of a patient, a medical device that delivers therapy to the patient according to a first therapy program during a first period, and a processor that receives the signal from the sensor during a second period following the first period, detects a carryover effect from delivery of the therapy according to the first therapy program based on the signal, where the carryover effect occurs during a washout period during the second period, and automatically controls the medical device to deliver therapy to the patient according to a second therapy program at a time based on the washout period.

In another embodiment, the disclosure is directed to a system comprising means for receiving a signal from a sensing device monitoring a physiological parameter of a patient during a first period during which therapy according to a first therapy program is delivered to the patient, means for detecting a carryover effect from the delivery of the therapy according to the first therapy program based on the signal, wherein the carryover effect occurs during a washout period following the first period, and means for automatically initiating delivery of therapy to the patient according to a second therapy program at a time based on the washout period.

In another embodiment, the disclosure is directed to a method comprising delivering psychiatric disorder therapy to a patient via a medical device according to a therapy program, monitoring a physiological parameter of the patient in response to the psychiatric disorder therapy, wherein the physiological parameter comprises at least one of a respiratory rate, electrodermal activity, thermal activity or muscle activity, determining a patient mood state based on the physiological parameter, and controlling the delivery of the psychiatric disorder therapy based on the determined patient mood state.

In another embodiment, the disclosure is directed to a system comprising a medical device that delivers psychiatric disorder therapy to a patient according to a therapy program, a sensing module that generates a signal indicative of a physiological parameter of the patient, wherein the physiological parameter comprises at least one of a respiratory rate, electrodermal activity, thermal activity or muscle activity, and a processor that receives the signal from the sensing module, determines a patient mood state based on the signal, and controls the delivery of the psychiatric disorder therapy by the medical device based on the determined patient mood state.

In another embodiment, the disclosure is directed to a system comprising means for delivering psychiatric disorder therapy to a patient according to a therapy program, means for monitoring a physiological parameter of the patient in response to the psychiatric disorder therapy, wherein the physiological parameter comprises at least one of a respiratory rate, electrodermal activity or muscle activity, means for determining a patient mood state based on the physiological parameter, and means for controlling the means for delivering psychiatric disorder therapy based on the determined patient mood state.

In another embodiment, the disclosure is directed to a method comprising delivering therapy to a patient according to a therapy program during a stimulation period, wherein the therapy program defines a value for at least one therapy parameter for managing a psychiatric condition of the patient, monitoring a physiological signal of the patient during the stimulation period, automatically determining a characteristic of the stimulation period based on the monitored physiological signal, determining a patient mood state based on the characteristic of the stimulation period, and associating the patient mood state with the therapy program in a memory.

In another embodiment, the disclosure is directed to a method comprising delivering therapy to a patient according to a therapy program during a time period, monitoring a physiological signal of the patient during the time period, receiving information indicative of a patient mood state, wherein the patient mood state occurs during the time period, and associating the patient mood state with at least one characteristic of the physiological signal during the time.

In another embodiment, the disclosure is directed to a system comprising a memory, a sensor that generates a signal as a function of at least one physiological parameter of a patient, a medical device that delivers therapy to a patient according to a therapy program to manage a psychiatric condition during a stimulation period, wherein the therapy program defines a value for at least one therapy parameter, and a processor that monitors the signal during the stimulation period, automatically determines a characteristic of the stimulation period based on the signal, determines a patient mood state based on the characteristic of the stimulation period, and associates the patient mood state with the therapy program in the memory.

In another embodiment, the disclosure is directed to a system comprising a memory, means for delivering therapy to a patient according to a therapy program during a stimulation period, wherein the therapy program defines a value for at least one therapy parameter for managing a psychiatric condition of the patient, means for monitoring a physiological signal of the patient during the stimulation period, means for automatically determining a characteristic of the stimulation period based on the monitored physiological signal, means for determining a patient mood state based on the characteristic of the stimulation period, and means for associating the patient mood state with the therapy program in the memory.

In another embodiment, the disclosure is directed to a method comprising delivering psychiatric disorder therapy to a patient via a medical device according to a therapy program, monitoring a physiological parameter of the patient in response to the psychiatric disorder therapy according to the therapy program, determining a first patient mood state based on the physiological parameter, receiving input indicating a second mood state experienced by the patient in response to the delivery of the psychiatric disorder therapy according to the therapy program, determining whether the first and second mood states are consistent to generate a consistency determination, and associating the consistency determination with the therapy program.

In another embodiment, the disclosure is directed to a system comprising a medical device that delivers psychiatric disorder therapy to a patient according to a therapy program, a sensing module that generates a signal indicative of a physiological parameter of the patient, and a processor that receives the signal from the sensing module, determines a first patient mood state based on the signal, receives input indicating a second mood state experienced by the patient in response to the delivery of the psychiatric disorder therapy according to the therapy program, determines whether the first and second mood states are consistent to generate a consistency determination, and associates the consistency determination with the therapy program.

In another aspect, the disclosure is directed to a computer-readable medium comprising instructions. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein.

The details of one or more examples are set forth in the accompanying drawings and the description below. Other features, objects, and advantages of the invention will be apparent from the description and drawings, and from the claims.

DETAILED DESCRIPTION

Figure 1:
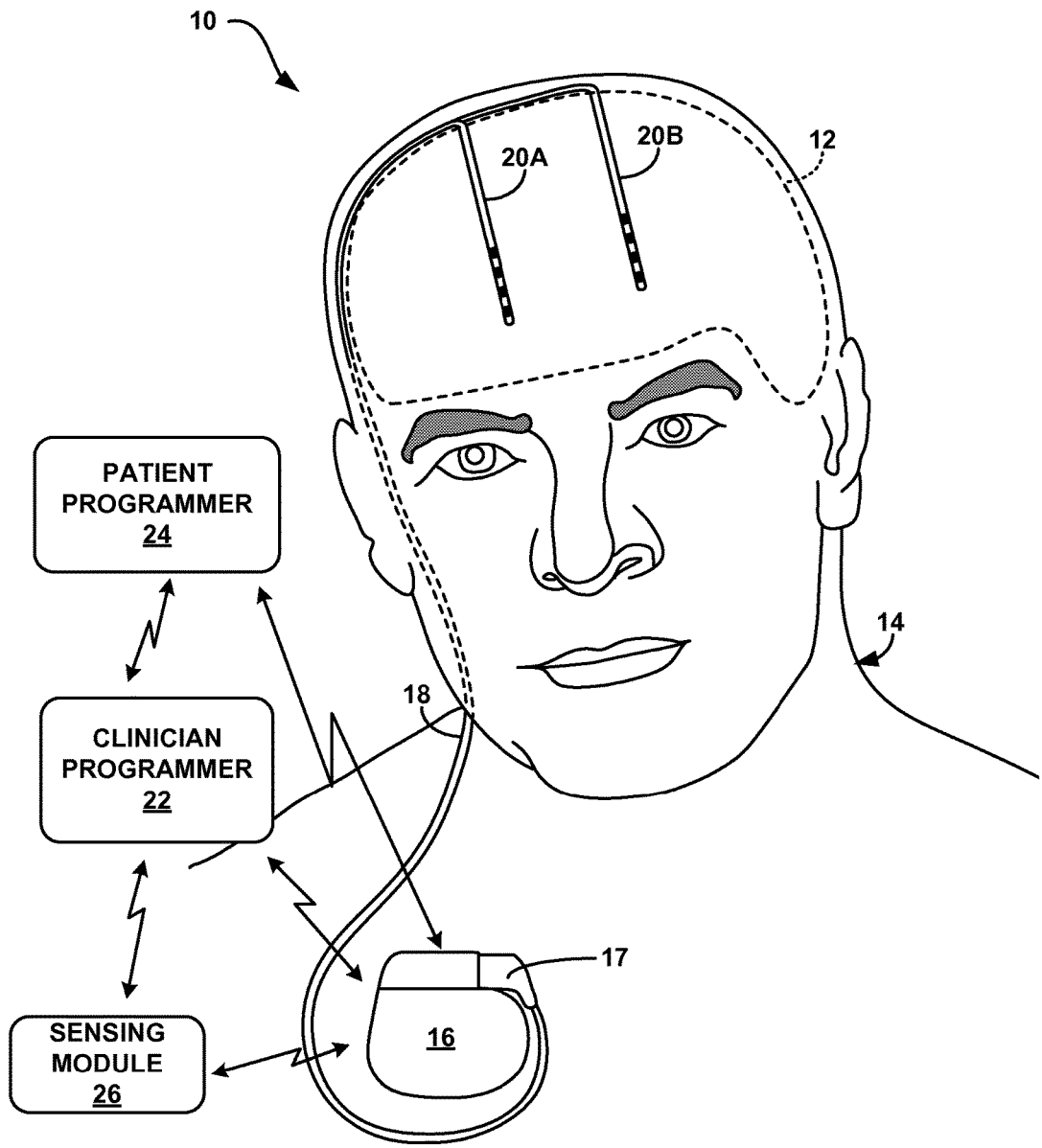
FIG. 1 is a conceptual diagram illustrating an example embodiment of a therapy system including an implantable medical device, a patient programmer, and a clinician programmer.

FIG. 1 is a conceptual diagram illustrating an embodiment of a therapy system 10 that is implanted proximate to brain 12 of patient 14 in order to help manage a patient condition, such as a psychiatric disorder. Examples of psychiatric disorders that therapy system 10 may be useful for managing include major depressive disorder (MDD), bipolar disorder, anxiety disorders, post traumatic stress disorder, dysthymic disorder, and obsessive-compulsive disorder (OCD). While patient 14 is generally referred to as a human patient, other mammalian or non-mammalian patients are also contemplated. Therapy system 10 includes implantable medical device (IMD) 16, connector block 17, lead extension 18, leads 20A and 20B, clinician programmer 22, patient programmer 24, and sensing module 26 (also referred to as "sensor 26"). IMD 16 includes a therapy module that delivers electrical stimulation therapy to one or more regions of brain 12 via leads 20A and 20B (collectively referred to as "leads 20"). In the embodiment shown in FIG. 1, therapy system 10 may be referred to a deep brain stimulation (DBS) system because IMD 16 provides electrical stimulation therapy directly tissue within brain 12, e.g. a tissue site under the dura mater of brain 12. In other embodiments, leads 20 may be positioned to deliver therapy to a surface of brain 12 (e.g., the cortical surface of brain 12).

In the embodiment shown in FIG. 1, IMD 16 may be implanted within a chest cavity of patient 14. In other embodiments, IMD 16 may be implanted within other regions of patient 14, such as a subcutaneous pocket in the abdomen of patient 14 or proximate the cranium of patient 14. Implanted lead extension 18 is coupled to IMD 16 via connector block 17, which may include, for example, electrical contacts that electrically couple to respective electrical contacts on lead extension 18. The electrical contacts electrically couple the electrodes carried by leads 20 to IMD 16. Lead extension 18 traverses from the implant site of IMD 16 within a chest cavity of patient 14, along the neck of patient 14 and through the cranium of patient 14 to access brain 12.

Leads 20 are implanted within the right and left hemispheres, respectively, of brain 12 in order deliver electrical stimulation to one or more regions of brain 12, which may be selected based on many factors, such as the type of patient condition for which therapy system 10 is implemented to manage. Different neurological or psychiatric disorders may be associated with activity in one or more of regions of brain 12, which may differ between patients. For example in the case of MDD, bipolar disorder, OCD or other anxiety disorders, leads 20 may be implanted to deliver electrical stimulation to the anterior limb of the internal capsule of brain 12, and only the ventral portion of the anterior limb of the internal capsule (also referred to as a VC/VS), the subgenual component of the cingulate cortex, anterior cingulate cortex Brodmann areas 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, the inferior thalamic peduncle, the dorsal medial nucleus of the thalamus, the habenula, or any combination thereof Although leads 20 are shown in FIG. 1 as being coupled to a common lead extension 18, in other embodiments, leads 20 may be coupled to IMD 16 via separate lead extensions or directly coupled to IMD 16. Leads 20 may deliver electrical stimulation to treat any number of neurological disorders or diseases in addition to psychiatric disorders, such as movement disorders or seizure disorders. Examples of movement disorders include a reduction in muscle control, motion impairment or other movement problems, such as rigidity, bradykinesia, rhythmic hyperkinesia, nonrhythmic hyperkinesia, dystonia, tremor, and akinesia. Movement disorders may be associated with patient disease states, such as Parkinson's disease or Huntington's disease. An example seizure disorder includes epilepsy.

Leads 20 may be implanted within a desired location of brain 12 via any suitable technique, such as through respective burr holes in a skull of patient 14 or through a common burr hole in the cranium. Leads 20 may be placed at any location within brain 12 such that the electrodes of the leads are capable of providing electrical stimulation to targeted tissue during treatment. Electrical stimulation generated from the signal generator (not shown) within the therapy module of IMD 16 may help prevent the onset of events associated with the patient's psychiatric disorder or mitigate symptoms of the psychiatric disorder. For example, electrical stimulation therapy delivered by IMD 16 to a target tissue site within brain 12 may help prevent a manic event if patient 14 has a bipolar disorder or help patient 14 maintain a mood state between a manic state and a depressive state. The exact therapy parameter values of the stimulation therapy, such as the amplitude or magnitude of the stimulation signals, the duration of each signal, the waveform of the stimuli (e.g., rectangular, sinusoidal or ramped signals), the frequency of the signals, and the like, may be specific for the particular target stimulation site (e.g., the region of the brain) involved as well as the particular patient and patient condition.

In the case of stimulation pulses, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities. Known techniques for determining the optimal stimulation parameters may be employed. In one embodiment, electrodes of leads 20 are positioned to deliver stimulation therapy to an anterior limb of the internal capsule of brain 12 in order to manage symptoms of a MDD of patient 14, and stimulation therapy is delivered via a selected combination of the electrodes to the anterior limb of the internal capsule with electrical stimulation including a frequency of about 2 hertz (Hz) to about 2000 Hz, a voltage amplitude of about 0.5 volts (V) to about 50 V, and a pulse width of about 60 microseconds (μs) to about 4 milliseconds (ms). However, other embodiments may implement stimulation therapy including other stimulation parameters.

The electrodes of leads 20 are shown as ring electrodes. Ring electrodes may be relatively easy to program and are typically capable of delivering an electrical field to any tissue adjacent to leads 20. In other embodiments, the electrodes of leads 20 may have different configurations. For example, the electrodes of leads 20 may have a complex electrode array geometry that is capable of producing shaped electrical fields. The complex electrode array geometry may include multiple electrodes (e.g., partial ring or segmented electrodes) around the perimeter of each lead 20, rather than a ring electrode. In this manner, electrical stimulation may be directed to a specific direction from leads 20 to enhance therapy efficacy and reduce possible adverse side effects from stimulating a large volume of tissue. In some embodiments, a housing of IMD 16 may include one or more stimulation and/or sensing electrodes. In alternative examples, leads 20 may have shapes other than elongated cylinders as shown in FIG. 1. For example, leads 20 may be paddle leads, spherical leads, bendable leads, or any other type of shape effective in treating patient 14.

In some embodiments, leads 20 may include sensing electrodes positioned to detect electrical signals (also referred to as bioelectrical brain signals) within one or more region of patient's brain 12. Alternatively, another set of sensing electrodes may monitor the electrical signal. The monitored electrical signals may include an electroencephalogram (EEG) signal. Electrodes implanted closer to the target region of brain 12 may help generate an EEG signal that provides more useful information than an EEG generated via a surface electrode array because of the proximity to brain 12. The EEG signal that is generated from implanted electrode array may also be referred to as an electrocorticography (ECoG) signal. In some embodiments, the electrical signals from within brain 12 may be used to determine a characteristic of a washout period, as described below with respect to FIG. 8. In other embodiments, an EEG signal of patient 14 may be monitored with external electrodes, e.g., scalp electrodes.

In some embodiments, the electrical signals from within brain 12 may be used to determine at least one characteristic of a washout period following delivery of therapy to a patient according to a therapy program. A washout period is the period of time following delivery of therapy to patient 14 during which one or more carryover effects from the therapy delivery substantially dissipates. In the case of electrical stimulation therapy, the carryover effect generally refers to a physiological effect from delivery of electrical stimulation signals that persist after termination of the signals. The end of the washout period associated with a therapy program may be the time at which at least one of the physiological effects resulting from the delivery of electrical stimulation therapy to patient 14 according to the therapy program have substantially dissipated, such that patient 14 returns to a baseline condition. The baseline condition may be, for example, the mood state or state of a physiological parameter prior to delivery of therapy according to the therapy program, or prior to the delivery of any therapy to patient 14.

One type of characteristic of the washout period may include the duration of the washout period, i.e., the time it takes for a physiological signal to return to a particular state, which may be a baseline state. The baseline state may be characterized by a range of amplitude values or a waveform and may be based on the state of patient 14 prior to delivery of stimulation according to a particular therapy program or prior to any therapy delivery. Other characteristics of the washout period may include the greatest or smallest amplitude of the physiological signal during the washout period, the average or median value of the physiological signal amplitude during the washout period, a trend in the physiological signal waveform during the washout period (e.g., a rate of change over time), a power level of the physiological signal measured in a particular frequency band of the physiological signal waveform during the washout period, ratios of power levels between different frequency bands during the washout period, and the like.

A carryover effect during the washout period may be detected by monitoring one or more physiological signals of patient 14 in addition to or instead of the EEG (or ECoG) signal. In embodiments in which therapy system 10 is used to manage a psychiatric disorder of patient 14, the physiological signals that are monitored may be indicative of the patient's mood state, although not necessarily symptomatic of the patient's mood disorder. In this way, characteristics of the physiological signal during the washout period may be a surrogate marker for a patient mood state. In different embodiments, suitable physiological signals for detecting a carryover effect and determining a characteristic of a washout period may include, but are not limited to, signals indicative of brain activity, heart rate, respiratory rate, electrodermal activity (e.g., skin conductance level or galvanic skin response), muscle activity (e.g., via EMG), thermal sensing (e.g. to detect facial flushing), or cardiac Q-T interval.

Brain activity may be indicated by, for example, monitoring electrical signals of the brain, such as EEG or ECoG signals. The heart rate and respiratory rate may be determined by measuring the heart rate and respiratory rate at any suitable place on the patient's body, and need not be directly measured from the heart or lungs. The electrodermal and thermal activity of patient 14 may be measured at the patient's face or any other suitable place on the patient's body, such as on the patient's hands (e.g., the palms), arms, legs, torso, neck, and the like. Thermal activity may indicate, for example, the temperature of the patient's skin due to skin flushing or an increase in blood flow in the region of the patient's skin. Monitoring the patient's muscle activity may detect changes to the patient's demeanor, such as changes to the patient's facial features (e.g., by detect facial contraction), tensing of the patient's neck and should muscles, clenching of the patient's hands, and the like. Such muscle movement may be detected via an EMG sensor.

A cardiac Q-T interval is a measure of the time between the start of the Q wave of the heart's electrical cycle and the end of the T wave, and is typically dependent upon the heart rate. Respiratory rate, heart rate, electrodermal activity, facial flushing, and cardiac Q-T interval signals may each be indicative of the patient's anxiety level. For example, a relatively high respiratory rate, heart rate, electrodermal activity, facial flushing, and Q-T interval may be indicative of a relatively high anxiety level of patient 14.

A decrease in the patient's anxiety level during a washout period may be desirable in situations in which therapy system 10 is used to provide therapy to manage an anxiety disorder or OCD. On the other hand, an increase in the patient's anxiety level during the washout period may be desirable in situations in which therapy system 10 is used to provide therapy to manage MDD. As described in further detail below, a therapy program may be selected such that the patient's heart rate or respiratory rate remains within a particular range in order to reduce or minimize the possibility of interfering with the patient's normal function or in order to reduce or minimize the possibility of causing patient 14 to achieve an abnormal emotional arousal state, such as elation, hypomania or mania.

Sensing module 26 is configured to monitor a physiological signal of patient 14 to detect a stimulation and/or carryover effect from therapy delivery and to determine a washout period characteristic for a particular therapy program. Sensing module 26 may be external to patient 14, may be implanted within patient 14 or may include portions both implanted and external to patient 14. In some embodiments, sensing module 26 may be incorporated in a common housing with IMD 16, may include electrodes on an outer housing of IMD 16 or may be coupled to IMD 16 via leads 20 or separate leads. Sensing module 26 is shown schematically in FIG. 1.

As described below with reference to FIG. 6, in some embodiments, sensing module 26 includes electrodes positioned on the patient's face in order to detect the electrical potential generated by the patient's facial muscle cells when the patient's face contracts. That is, in some embodiments, sensing module 26 may include one or more electrodes positioned to detect EMG signals, which may indicate changes to the patient's facial expressions. Certain EMG signals may be associated with particular facial expressions, e.g., during a learning process. In some embodiments, sensing module 26 may include one or more thermal sensing electrodes positioned on the patient's face in order to detect facial flushing, and/or one or more sensing electrodes to detect electrodermal activity, which may indicate changes in conductivity of the patient's skin (e.g., attributable to perspiration). In addition to or instead of the EMG or thermal sensing electrodes, sensing module 26 may include a respiration belt or an electrocardiogram (ECG) belt, as described below with reference to FIG. 6.

If sensing module 26 determines one or more physiological parameters of patient 14 within brain 12, sensing module 26 and IMD 16 may deliver and sense therapy to the same or different target tissue sites. For example, in one embodiment, sensing module 26 may detect an EEG signal within the CG25 of brain 12, while IMD 16 delivers therapy to the VC/VS. The CG25 of brain 12 may also be referred to as the subgenual cingulate. As another example, sensing module 26 may detect an EEG signal within the VC/VS of brain 12, while IMD 16 delivers therapy to the CG25. As another example, both IMD 16 and sensing module 26 may be configured to deliver therapy and sense, respectively, within the VC/VS of brain 12. In other cases, both IMD 16 and sensing module 26 may be configured to deliver therapy and sense, respectively, within the CG25 of brain 12.

IMD 16 includes a therapy module that generates the electrical stimulation delivered to patient 14 via leads 20. In the embodiment shown in FIG. 1, IMD 16 generates the electrical stimulation according to one or more therapy parameters, which may be arranged in a therapy program (or a parameter set). In particular, a signal generator (not shown) within IMD 16 produces the stimulation in the manner defined by the therapy program or group of programs selected by the clinician and/or patient 14. The signal generator may be configured to produce electrical pulses to treat patient 14. In other embodiments, the signal generator of IMD 16 may be configured to generate a continuous wave signal, e.g., a sine wave or triangle wave. In either case, IMD 16 generates the electrical stimulation therapy for DBS according to therapy parameter values defined by a particular therapy program.

A therapy program defines respective values for a number of parameters that define the stimulation. For example, the therapy parameters may include voltage or current pulse amplitudes, pulse widths, pulse rates, pulse frequencies, electrode combinations, and the like. IMD 16 may store a plurality of programs. In some cases, the one or more stimulation programs are organized into groups, and IMD 16 may deliver stimulation to patient 14 according to a program group. During a trial stage in which IMD 16 is evaluated to determine whether IMD 16 provides efficacious therapy to patient 14, the stored programs may be tested and evaluated for efficacy.

IMD 16 may include a memory to store one or more therapy programs (e.g., arranged in groups), and instructions defining the extent to which patient 14 may adjust therapy parameters, switch between programs, or undertake other therapy adjustments. Patient 14 may generate additional programs for use by IMD 16 via patient programmer 24 at any time during therapy or as designated by the clinician.

Generally, an outer housing of IMD 16 is constructed of a biocompatible material that resists corrosion and degradation from bodily fluids. IMD 16 may be implanted within a subcutaneous pocket close to the stimulation site. Although IMD 16 is implanted within a chest cavity of patient 14 in the embodiment shown in FIG. 1, in other embodiments, IMD 16 may be implanted within cranium. In addition, while IMD 16 is shown as implanted within patient 14 in FIG. 1, in other embodiments, IMD 16 may be located external to the patient. For example, IMD 16 may be a trial stimulator electrically coupled to leads 20 via a percutaneous lead during a trial period. If the trial stimulator indicates therapy system 10 provides effective treatment to patient 14, the clinician may implant a chronic stimulator within patient 14 for long term treatment.

Clinician programmer 22 may be a computing device including, for example, a personal digital assistant (PDA), a laptop computer, a desktop PC, a workstation, and the like that permits a clinician to program electrical stimulation therapy for patient 14, e.g., using input keys and a display. For example, using clinician programmer 22, the clinician may specify therapy programs that include one or more therapy parameters and/or organize the therapy programs into therapy program groups (i.e., groups including one or more therapy parameters) for use in delivery of DBS. Clinician programmer 22 supports telemetry (e.g., radio frequency (RF) telemetry) with IMD 16 to download stimulation parameters and, optionally, upload operational or physiological data stored by IMD 16. In this manner, the clinician may periodically interrogate IMD 16 to evaluate efficacy and, if necessary, modify the stimulation parameters.

Like clinician programmer 22, patient programmer 24 may be a handheld computing device. Patient programmer 24 may also include a display and input keys to allow patient 14 to interact with patient programmer 24 and IMD 16. In this manner, patient programmer 24 provides patient 14 with an interface for limited control of electrical stimulation therapy provided by IMD 16. For example, patient 14 may use patient programmer 24 to start, stop or adjust electrical stimulation therapy. In particular, patient programmer 24 may permit patient 14 to adjust stimulation parameters such as duration, amplitude, pulse width and pulse rate within an adjustment range specified by the clinician via clinician programmer 22, select from a library of stored stimulation therapy programs, or reset the current therapy cycle.

Patient programmer 24 includes input mechanisms to allow patient 14 to enter information related to a patient event or information in response to the delivery of therapy according to a particular therapy program. For example, any of the above-listed input mechanisms may be used to enter information including, but not limited to, information characterizing the patient mood during a washout period following delivery of therapy to patient 14 according to a specific therapy program. The information entered by patient 14 may be associated with the specific therapy program.

Clinician programmer 22 may be used to program and/or interrogate IMD 16 and patient programmer 24, as described in further detail below. IMD 16, clinician programmer 22, and patient programmer 24 may communicate via cables or a wireless communication, as shown in FIG. 1. Clinician programmer 22 and patient programmer 24 may, for example, communicate via wireless communication with IMD 16 using RF telemetry techniques known in the art. Clinician programmer 22 and patient programmer 24 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

Although IMD 16 configured to deliver electrical stimulation is illustrated in the embodiment shown in FIG. 1, in other embodiments, therapy system 10 may include a medical device configured to deliver a therapeutic agent in addition to or instead of IMD 16. The therapeutic agent may be used to provide therapy to patient 14 to manage a psychiatric disorder of patient 14, and may be delivered to the patient's brain 12, blood stream or tissue. In some embodiments, the medical device that delivers the therapeutic agent is implanted within patient 14, while in other embodiments, the medical device is external to patient 14. For example, the medical device may be an implanted or external drug pump that delivers a therapeutic agent to a target tissue site within patient 14 with the aid of one or more catheters. As another example, the medical device may be an external patch that is worn on a skin surface of patient 14, where the patch elutes a therapeutic agent, which is then absorbed by the patient's skin. Other types of therapeutic agent delivery systems are contemplated.

Figure 2:
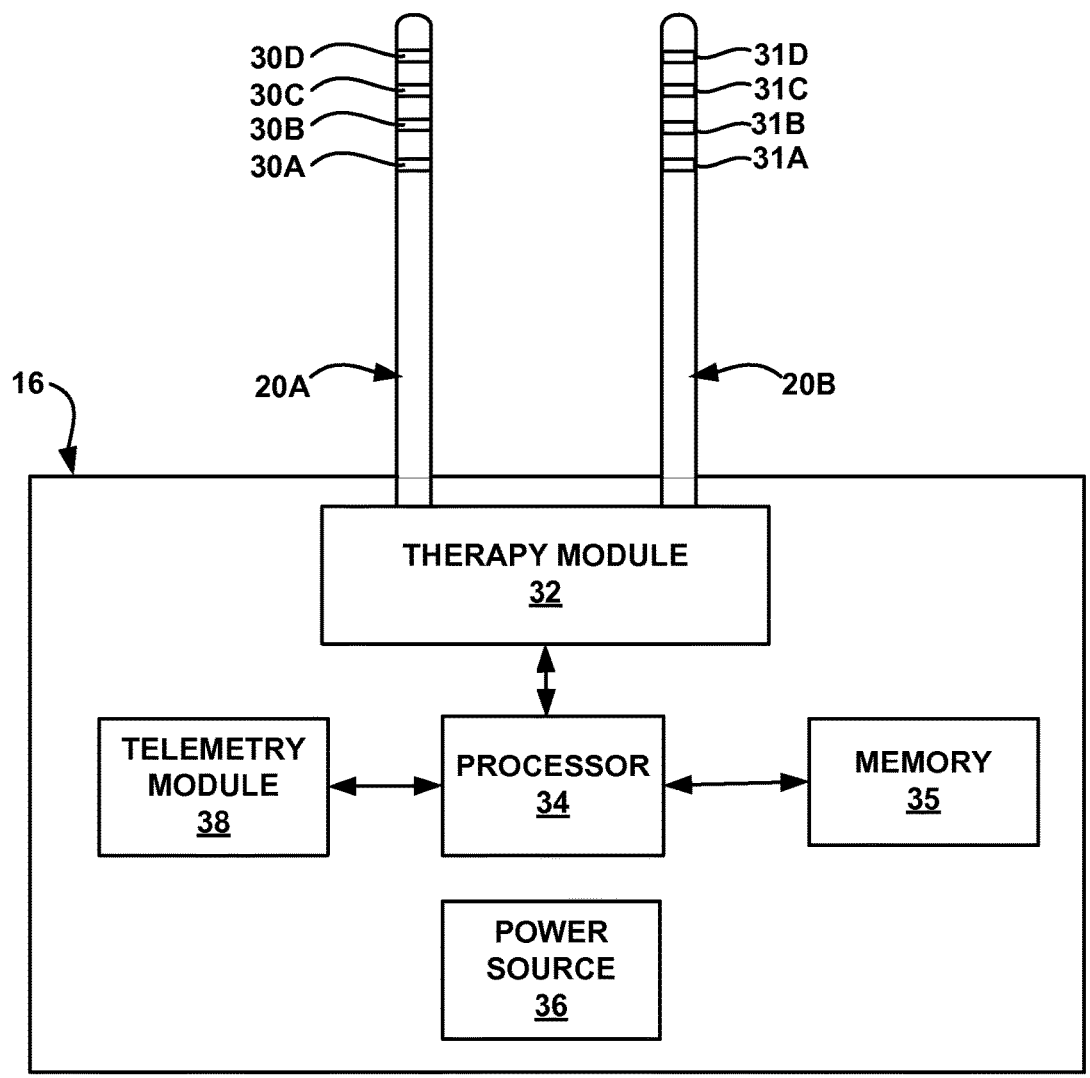
FIG. 2 is a schematic block diagram illustrating example components of the implantable medical device of FIG. 1.

FIG. 2 is a functional block diagram illustrating components of an embodiment of IMD 16 in greater detail. IMD 16 is coupled to leads 20A and 20B, which include electrodes 30A-30D and 31A-31D, respectively. Although IMD 16 is coupled directly to leads 20, in other embodiments, IMD 16 may be coupled to leads 20 indirectly, e.g., via lead extension 18 (FIG. 1). In the example shown in FIG. 2, IMD 16 includes therapy module 32, processor 34, memory 35, power source 36, and telemetry module 38.

IMD 16 may deliver electrical stimulation therapy to brain 12 of patient 14 via electrodes 30A-30D of lead 20A and electrodes 31A-30D of lead 20B (collectively "electrodes 30 and 31"). In the embodiment shown in FIG. 2, implantable medical leads 20 are substantially cylindrical, such that electrodes 30, 31 are positioned on a rounded outer surface of leads 20. As previously described, in other embodiments, leads 20 may be, at least in part, paddle-shaped (i.e., a "paddle" lead). In some embodiments, electrodes 30, 31 may be ring electrodes. In other embodiments, electrodes 30, 31 may be segmented or partial ring electrodes, each of which extends along an arc less than 360 degrees (e.g., 90-120 degrees) around the outer perimeter of the respective lead 20. The use of segmented or partial ring electrodes 30, 31 may also reduce the overall power delivered to electrodes 30, 31 by IMD 16 because of the ability to more efficiently deliver stimulation to a target stimulation site by eliminating or minimizing the delivery of stimulation to unwanted or unnecessary regions within patient 16.

The configuration, type, and number of electrodes 30, 31 illustrated in FIG. 2 are merely exemplary. For example, IMD 16 may be coupled to one lead with eight electrodes on the lead or three or more leads with the aid of bifurcated lead extensions. Electrodes 30, 31 are electrically coupled to a therapy module 32 of IMD 16 via conductors within the respective leads 20A, 20B. Each of electrodes 30, 31 may be coupled to separate conductors so that electrodes 30, 31 may be individually selected, or in some embodiments, two or more electrodes 30 and/or two or more electrodes 31 may be coupled to a common conductor. In one embodiment, an implantable signal generator or other stimulation circuitry within therapy module 32 delivers electrical signals (e.g., pulses or substantially continuous-time signals, such as sinusoidal signals) to a target tissue site within patient 14 via at least some of electrodes 30, 31 under the control of processor 34. The stimulation energy generated by therapy module 32 may be delivered from therapy module 32 to selected electrodes 30, 31 via a switching module and conductors carried by leads 16, as controlled by processor 34.

Processor 34 may include any one or more of a microprocessor, a controller, a digital signal processor (DSP), an application specific integrated circuit (ASIC), a field programmable gate array (FPGA), discrete logic circuitry, or the like. The functions attributed to processors described herein may be embodied in a hardware device via software, firmware, hardware or any combination thereof. Processor 34 controls the implantable signal generator within therapy module 32 to deliver electrical stimulation therapy according to selected therapy parameters. Specifically, processor 34 controls therapy module 32 to deliver electrical signals with selected voltage or current amplitudes, pulse widths (if applicable), and rates specified by one or more therapy programs, which may be arranged into therapy program groups. In one embodiment, processor 34 controls therapy module 32 to deliver stimulation therapy according to one therapy program group at a time. The therapy programs may be stored within memory 35. In another embodiment, therapy programs are stored within at least one of clinician programmer 22 or patient programmer 24, which transmits the therapy programs to IMD 16 via telemetry module 38.

In addition, processor 34 may also control therapy module 32 to deliver the electrical stimulation signals via selected subsets of electrodes 30, 31 with selected polarities. For example, electrodes 30, 31 may be combined in various bipolar or multi-polar combinations to deliver stimulation energy to selected sites, such as sites within brain 12. The above-mentioned switch matrix may be controlled by processor 34 to configure electrodes 30, 31 in accordance with a therapy program.

In embodiments in which IMD 16 senses a patient parameter, such as an EEG, ECoG, heart rate or respiratory rate of patient 14, processor 34 may control therapy module 32 to sense the patient parameter. The sensed parameter signals generated by therapy module 32 may be stored within memory 35. Memory 35 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. Memory 35 may store program instructions that, when executed by processor 34, cause IMD 16 to perform the functions ascribed to IMD 16 herein. In some embodiments, memory 35 may also store the parameters for therapy programs or program groups and/or patient physiological data (such as sensed physiological signals) obtained by IMD 16 or another sensing device.

During a trial session, which may occur after implantation of IMD 16 or prior to implantation of IMD 16, a clinician may determine the therapy parameter values that provide efficacious therapy to patient 14. Processor 34 may control therapy module 32 based on information provided by clinician programmer 22, patient programmer 24 or another computing device. For example, the clinician may interact with clinician programmer 22 to select a particular therapy program and clinician programmer 22 may transmit a control signal to IMD 16, which is received by telemetry module 38 of IMD 16. The control signal may cause processor 34 to control therapy module 32 to deliver therapy based on the parameter values specific by the clinician-selected therapy program. As another example, clinician programmer 22, patient programmer 24 or another computing device may utilize a search algorithm that automatically selects therapy programs for trialing, i.e., testing on patient 14. When a therapy program is trialed, therapy is delivered to patient 14 according to the therapy program for a predetermined amount of time, which may be a few minutes to a few hours or days, in order to assess the efficacy of the therapy program in managing the patient's condition. The efficacy of the therapy program may be analyzed in terms of the therapeutic benefits to patient 14, as well as the existence of side effects, which may include the presence, severity, and duration of the side effects.

Figure 3:
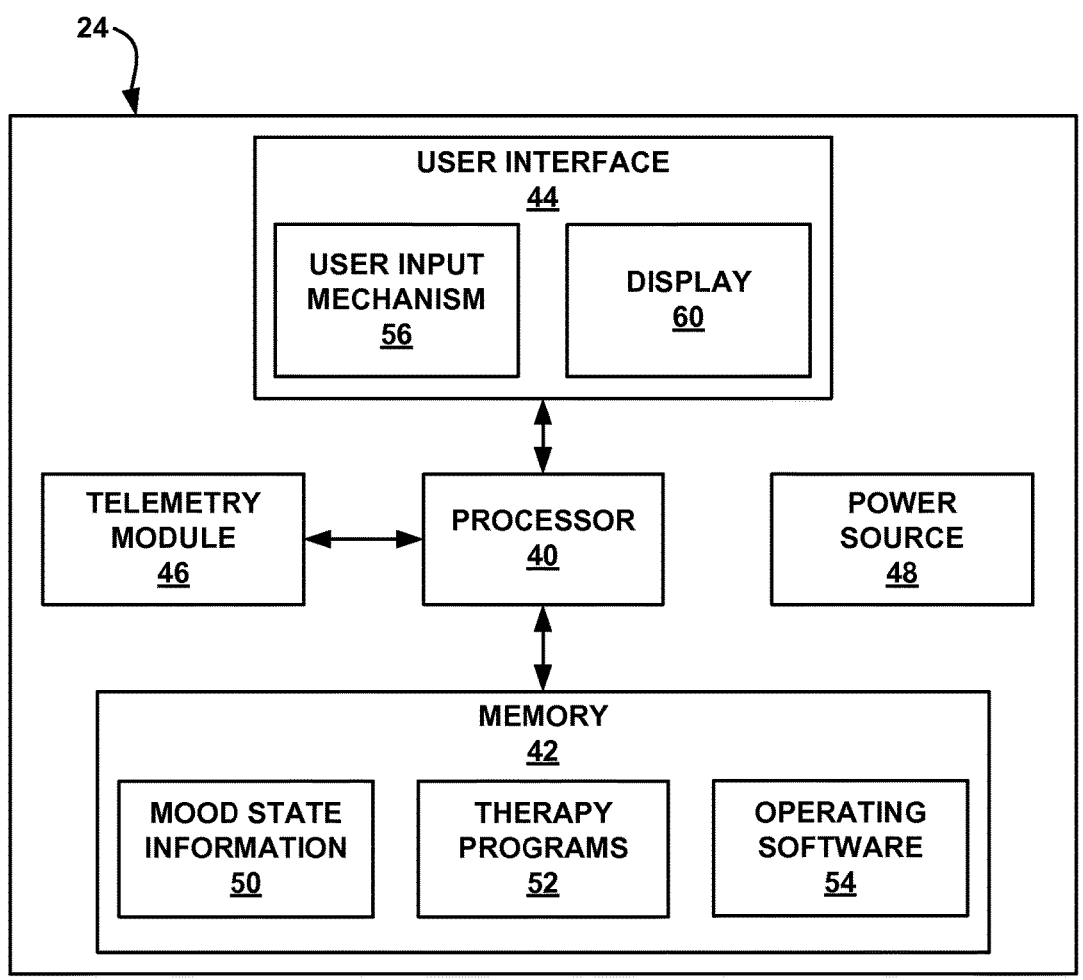
FIG. 3 is a schematic block diagram illustrating example components of the patient programmer of FIG. 1.

FIG. 3 is a functional block diagram illustrating components of an example patient programmer 24, which includes processor 40, memory 42, user interface 44, telemetry module 46, and power source 48. Processor 40 controls user interface 44 and telemetry module 46, and stores and retrieves information and instructions to and from memory 42. Patient programmer 24 may be a dedicated hardware device with dedicated software for programming of IMD 16. Alternatively, patient programmer 24 may be an off-the-shelf computing device running an application that enables programmer 24 to program IMD 16.

Patient 14 may use patient programmer 24 to select therapy programs (e.g., sets of stimulation parameter values), generate new therapy programs, modify therapy programs through individual or global adjustments or transmit the new programs to a medical device, such as IMD 16 (FIGS. 1 and 2). Patient 14 may interact with patient programmer 24 via user interface 44, which includes user input mechanism 56 and display 60. Patient 14 may input information via user interface 44 relating to the therapeutic efficacy of a therapy program or a mood state during a washout period following therapy delivery by IMD 16 according to a particular therapy program.

User input mechanism 56 may include any suitable mechanism for receiving input from patient 14 or another user. In one embodiment, user input mechanism includes an alphanumeric keypad. In another embodiment, user input mechanism 56 includes a limited set of buttons that are not necessarily associated with alphanumeric indicators. For example, the limited set of buttons may include directional buttons that permit patient 14 to scroll up, down, or sideways through a display presented on display 60, select items shown on display 60, as well as enter information. The limited set of buttons may also include "increment/decrement" buttons in order to increase or decrease a stimulation frequency or amplitude of stimulation delivered by IMD 16.

User input mechanism 56 may include any one or more of push buttons, soft-keys (e.g., with functions and contexts indicated on display 60), voice activated commands, mechanisms activated by physical interactions, magnetically triggered mechanisms, mechanisms activated upon password authentication push buttons, contacts defined by a touch screen, or any other suitable user interface. In some embodiments, buttons of user input mechanism 56 may be reprogrammable. That is, during the course of use of patient programmer 24, the buttons of user input mechanism 56 may be reprogrammed to provide different programming functionalities as the needs of patient 14 change or if the type of IMD 16 implanted within patient 14 changes. User input mechanism 56 may be reprogrammed, for example, by clinician programmer 22 (FIG. 1) or another computing device.

Display 60 may include a color or monochrome display screen, such as a liquid crystal display (LCD), light emitting diode (LED) display or any other suitable type of display. Patient programmer 24 may present information related to stimulation therapy provided by IMD 16, as well as other information, such as historical data regarding the patient's condition and past event information. Processor 40 monitors activity from user input mechanism 56, and controls display 60 and/or IMD 16 function accordingly. In some embodiments, display 60 may be a touch screen that enables the user to select options directly from the display. In such cases, user input mechanism 56 may be eliminated, although patient programmer 24 may include both a touch screen and user input mechanism 56. In some embodiments, user interface 44 may also include audio circuitry for providing audible instructions or sounds to patient 14 and/or receiving voice commands from patient 14.

User interface 44 may also include an LED or another indication (e.g., via display 60) that provides confirmation to patient 14 that an operation was carried out or that information input via user input mechanism 56 was received. For example, following cessation of therapy delivery according to a therapy program, user interface 44 may prompt patient 14 to provide feedback during the washout period. After patient 14 provides feedback, user interface 44 may activate an LED to provide positive feedback to patient 16 regarding the successfully received information.

Processor 40 may comprise any combination of one or more processors including one or more microprocessors, DSPs, ASICs, FPGAs, or other equivalent integrated or discrete logic circuitry. Accordingly, processor 40 may include any suitable structure, whether in hardware, software, firmware, or any combination thereof, to perform the functions ascribed herein to processor 40. Memory 42 may include any volatile or nonvolatile memory, such as RAM, ROM, EEPROM or flash memory. Memory 42 may also include a removable memory portion that may be used to provide memory updates or increases in memory capacities. A removable memory may also allow patient data to be easily transferred to clinician programmer 22, or to be removed before patient programmer 24 is used by a different patient.

Memory 42 stores, among other things, mood state information 50, therapy programs 52, and operating software 54. Memory 42 may have any suitable architecture. For example, memory 42 may be partitioned to store mood state information 50, therapy programs 52, and operating software 54. Alternatively, mood state information 50, therapy programs 52, and operating software 54 may each include separate memories that are linked to processor 40.

Therapy programs 52 portion of memory 42 stores data relating to the therapy programs implemented by IMD 16. In some embodiments, the actual settings for the therapy programs, e.g., the stimulation amplitude, pulse rate, pulse frequency and pulse width data, are stored within therapy programs 52. In other embodiments, an indication of each therapy program or group of therapy programs, e.g., a single value associated with each therapy program or group, may be stored within therapy programs 52, and the actual parameters may be stored within memory 35 of IMD 16. The "indication" for each therapy program or group may include, for example, alphanumeric indications (e.g., Therapy Program Group A, Therapy Program Group B, and so forth), or symbolic indications.

Operating software 54 may include instructions executable by processor 40 for operating user interface 44, telemetry module 46 and managing power source 48. Memory 42 may also store any therapy data retrieved from IMD 16 during the course of therapy. The clinician may use this therapy data to determine the progression of the patient's disease in order to predict or plan a future treatment.

Patient programmer 24 may communicate via wireless telemetry with IMD 16, such as using RF communication or proximal inductive interaction. This wireless communication is possible through the use of telemetry module 46. Accordingly, telemetry module 46 may be similar to the telemetry module contained within IMD 16. Telemetry module 46 may also be configured to communicate with clinician programmer 22 or another computing device via wireless communication techniques, or direct communication through a wired connection. Examples of local wireless communication techniques that may be employed to facilitate communication between patient programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with patient programmer 24 without needing to establish a secure wireless connection.

Power source 48 delivers operating power to the components of patient programmer 24. Power source 48 may include a battery and a power generation circuit to produce the operating power. In some embodiments, the battery may be rechargeable to allow extended operation. Recharging may be accomplished electrically coupling power source 48 to a cradle or plug that is connected to an alternating current (AC) outlet. In addition, recharging may be accomplished through proximal inductive interaction between an external charger and an inductive charging coil within patient programmer 24. In other embodiments, traditional batteries (e.g., nickel cadmium or lithium ion batteries) may be used. In addition, patient programmer 24 may be directly coupled to an alternating current outlet recharge power source 48, or to power patient programmer 24. Power source 48 may include circuitry to monitor power remaining within a battery. In this manner, user interface 44 may provide a current battery level indicator or low battery level indicator when the battery needs to be replaced or recharged. In some cases, power source 48 may be capable of estimating the remaining time of operation using the current battery.

Figure 4:
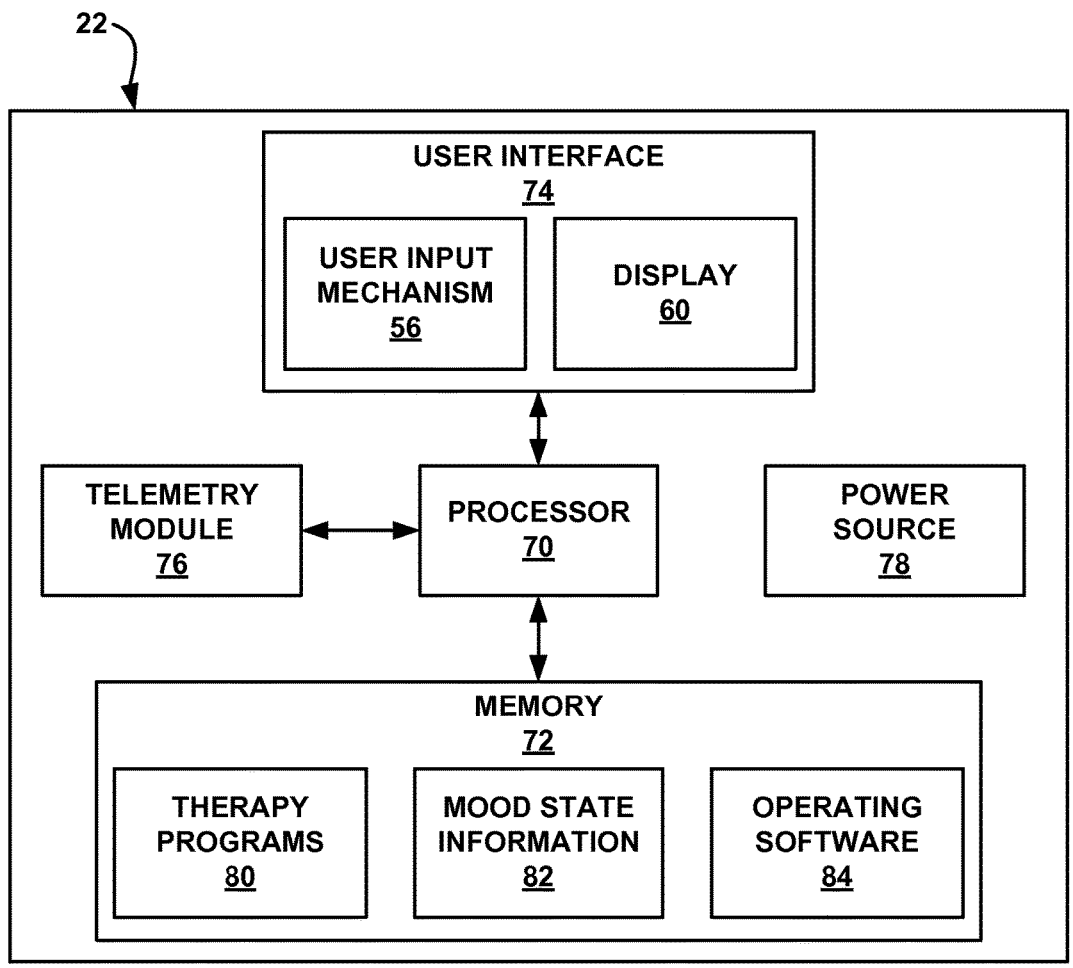
FIG. 4 is a schematic block diagram illustrating example components of the clinician programmer of FIG. 1.

FIG. 4 is a functional block diagram illustrating components of clinician programmer 22, which may be similar to patient programmer 24. Clinician programmer 22 may include a processor 70, memory 72 including therapy programs 80, mood state information 82, and operating software 84, user interface 74 including user input mechanism 56 and display 60, telemetry module 76, and power source 78. The functions performed by each component may be similar to the functions described above with reference to patient programmer 24. Additionally, clinician programmer 22 may include more features than patient programmer 24. For example, while clinician programmer 22 may be configured for more advanced programming features than patient programmer 24. This may allow a user to modify more therapy parameters with clinician programmer than with patient programmer 24. Patient programmer 24 may have a relatively limited ability to modify therapy parameters of IMD 16 in order to minimize the possibility of patient 14 selecting therapy parameters that are harmful to patient 14. Similarly, clinician programmer 22 may conduct more advanced diagnostics of IMD 16 than patient programmer 24.

As described in further detail below, processor 70 of clinician programmer 22 may interrogate IMD 16 and/or patient programmer 24 to retrieve any collected information stored within memories 35, 42, such as information associated with therapy programs, which may include information received from patient 14 relating to a mood state, or physiological parameter values. The physiological parameter values may be values monitored during the stimulation period, i.e., when IMD 16 is actively delivering stimulation signals to target tissue within patient 14, or during the washout period, i.e., the period following the stimulation period. For example, memory 72 of clinician programmer 22 may include software including instructions that cause processor 70 of clinician programmer 22 to interrogate IMD 16 and/or patient programmer 24. The information associated with therapy programs may be stored within therapy program information portion 80 of memory 72.

In general, during a programming session, a clinician may select values for a number of programmable therapy parameters in order to define the electrical stimulation therapy to be delivered by IMD 16 to patient 14. For example, the clinician may select a combination of electrodes carried by one or more implantable leads, and assigns polarities to the selected electrodes. In addition, the clinician may select an amplitude, which may be a current or voltage amplitude, a pulse width, and a pulse rate, in the case of an IMD 16 that delivers stimulation pulses to patient 14. A group of parameter values, including electrode configuration (electrode combination and electrode polarity), amplitude, pulse width and pulse rate, may be referred to as a therapy program in the sense that they drive the neurostimulation therapy to be delivered to the patient.

Programs selected during a programming session using clinician programmer 22 may be transmitted to and stored within one or both of patient programmer 24 and IMD 16. Where the programs are stored in patient programmer 24, patient programmer 24 may transmit the programs selected by patient 14 to IMD 16 for delivery of neurostimulation therapy to patient 14 according to the selected program. Where the programs are stored in IMD 16, patient programmer 24 may receive a list of programs from IMD 16 to display to patient 14, and transmit an indication of the selected program to IMD 16 for delivery of neurostimulation therapy to patient 14 according to the selected program.

During a programming session, which may also be referred to as a therapy program trial session, the clinician may specify a program using clinician programmer 22 by selecting values for various therapy parameters. When a program is specified, the clinician may test the program by directing clinician programmer 22 to control IMD 16 to deliver therapy according to the program to patient 14. The clinician or patient 14 may enter rating information into the programming device for each tested program. The rating information for a tested program may include information relating to effectiveness of delivery of stimulation therapy according to the program in treating symptoms of the patient, side effects experienced by the patient due to the delivery of neurostimulation therapy according to the program, or both. In the case of psychiatric disorder stimulation therapy, efficacy information may include an indication of patient mood state during therapy delivery and during a washout period following therapy delivery. The patient mood state information may include, for example, patient feedback (received via patient programmer 22) and/or physiological parameter values that are associated with a particular patient mood state.

During the programming session, multiple therapy programs may be tested (or trialed). That is, during a programming session, IMD 16 may deliver therapy to patient 14 according to a first therapy program, followed by a second therapy program, and so forth, in order to assess the efficacy of each therapy program. Clinician programmer 22 may maintain a session log in memory 72, where the session log includes a listing of programs tested on patient 14, rating information provided by the clinician or patient 14 for programs of the list, washout period information, and mood state information. The listing may be ordered according to the rating information in order to facilitate the selection of programs from the list by the clinician.

For at least some of the tested therapy programs, at least one characteristic of a washout period may be determined based on one or more monitored physiological signals of patient 14. As previously indicated, washout period characteristics may include the duration of the washout period or one or more waveform characteristics of one or more physiological signals during the washout period.

FIGS. 5A-5E are schematic diagrams of a physiological signal waveform prior to, during, and after delivery of electrical stimulation signals by IMD 16. The diagrams shown in FIGS. 5A-5E illustrate different types of physiological signal waveforms that may occur during a period following delivery of stimulation ("post-stimulation period"), which may indicate the presence of one or more carryover effects generated by therapy delivery according to the therapy parameter values of a particular therapy program, and may be used to determine a washout period characteristic. The post-stimulation period may be immediately after the stimulation period. The washout period generally refers to the portion of the post-stimulation period during which carryover effects generated by therapy delivery are present.

Figure 5A:
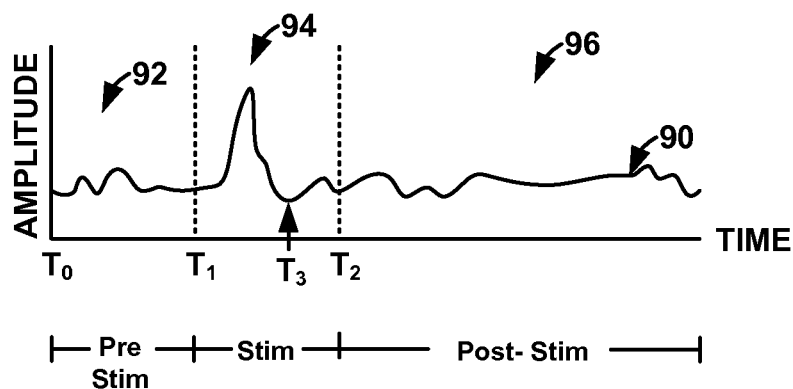
FIGS. 5A-5E are schematic diagrams of physiological signal waveforms prior to, during, and after delivery of electrical stimulation signals by a medical device.

FIG. 5A illustrates a scenario in which therapy delivery according to a first therapy program generates a stimulation effect but does not generate a carryover effect, and, therefore, the washout period has a duration of approximately 0 seconds (sec. or s). Processor 70 of clinician programmer 22 may establish a baseline characteristic of physiological signal 90 during a pre-stimulation period 92, prior to delivery of stimulation by IMD 16 according to the first therapy program. While processor 70 is primarily referred to throughout the description of FIGS. 5A-5E, in other embodiments, a processor of another device, such as patient programmer 24 or IMD 16, may monitor a physiological signal and determine one or more washout period characteristics for a particular therapy program.

In some embodiments, processor 70 establishes a baseline state of physiological signal 90 prior to any stimulation delivery by IMD 16 or prior to stimulation delivery by IMD 16 according to the first therapy program or another therapy program. The baseline state may be defined by a signal characteristic, such as an peak, average or median amplitude value of physiological signal 90, a trend in physiological signal 90 (e.g., a trend in inflection points or a slope), a power level within one or more frequency bands of physiological signal 90, a range of any of the aforementioned signal characteristics, and the like. In some embodiments, the baseline state of physiological signal 90 may be based on the physiological signal 90 prior to therapy delivery according to the first therapy program, i.e., prior to time $T_1$. For example, the baseline state may be a characteristic of signal 90 that indicates patient 14 is in a baseline mood state, which may be the mood state that occurs when therapy system 10 does not deliver any therapy to patient 14. For example, if patient 14 is afflicted with MDD, the baseline mood state may be a severe or moderately depressed mood state.

As shown in FIG. 5A, during the delivery of stimulation signals by IMD 16, i.e., during stimulation period 94, the waveform of physiological signal 90 may differ from the waveform observed during pre-stimulation period 92. The first therapy program defines a frequency of stimulation signals delivered to patient 14 during stimulation period 94, i.e., the rate at which the stimulation signals are delivered. Accordingly, stimulation signals in the form of electrical pulses may be separated by an interval of time. Stimulation period 94 refers to the entire stimulation session, including the delivery of the stimulation signal and the intervals between signals, rather than merely the period of time that corresponds to the delivery of a stimulation signal.

The change in the amplitude of physiological signal 90 during stimulation period 94 indicates that therapy delivery according to the first therapy program resulted in a stimulation effect on patient 14. During stimulation period 94, physiological signal 90 returns to the baseline amplitude value at time $T_3$. After therapy module 32 of IMD 16 (FIG. 2) terminates therapy delivery according to the first therapy program, as indicated by the post-stimulation period 96 beginning at time $T_2$, physiological signal 90 substantially returns to the baseline state, e.g., the baseline signal characteristic determined during pre-stimulation period 92.

Processor 70 may determine when physiological signal 90 returns to a baseline state by comparing the respective characteristic of physiological signal 90 during post-stimulation period 96 to the baseline state. For example, processor 70 may compare an amplitude of signal 90 during post-stimulation period 96 to a baseline amplitude. In some cases, signal 90 may not return to the exact baseline amplitude (or other signal characteristic defining the baseline state) during post-stimulation period 96. Thus, in some embodiments, processor 70 may determine that signal 90 has returned to the baseline state if the amplitude value of signal 90 falls within a predetermined range of the baseline value, such as about 1% to about 10% of the baseline amplitude value. The clinician may select the predetermined percentage, which may depend upon the type of physiological signal that is monitored.

The time windows for pre-stimulation period 92, stimulation period 94, and post-stimulation period 96 may be fixed or may be defined by the clinician, e.g., based on the actually time periods during which the delivery of electrical stimulation therapy begins and ends. For example, in some cases, the clinician may test one therapy program longer than another, thereby resulting in a longer stimulation period 94 for one therapy program compared to another therapy program.

Figure 5B:
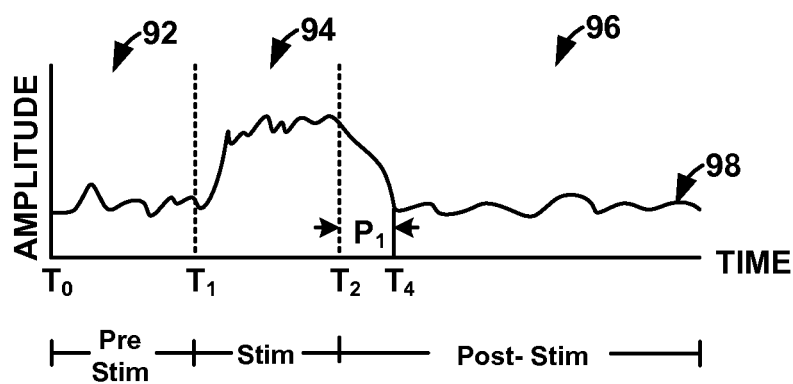

FIG. 5B illustrates a waveform of physiological signal 98 prior to, during, and after stimulation delivery according to a second therapy program that generates a stimulation effect and an immediate carryover effect. A baseline state of physiological signal 98 may be established during a pre-stimulation period 92, which may be prior to delivery of any stimulation by IMD 16 or prior to delivery of stimulation by IMD 16 according to the second therapy program. The baseline state of a physiological signal may change over time. For example, if physiological signal 90 (FIG. 5A) indicates the same patient parameter as physiological signal 98, the baseline states of physiological signals 90, 98 may differ depending on whether any prior therapy programs were tested prior to the determination of the baseline states.

In some cases, if the first therapy program is tested prior to the second therapy program, such that the pre-stimulation period 92 of FIG. 5B follows the post-stimulation period 96 of FIG. 5A, the baseline state of physiological signal 98 may be characterized by a higher amplitude value than the baseline state of physiological signal 90 due to changes in the physiological parameter of patient 14 that were generated based on therapy delivery according to the first therapy program. Thus, processor 70 may implement an adaptive baseline state for a physiological signal to account for physiological effects from prior therapy delivery. However, as discussed above, in some examples, a single baseline state may be established, e.g., at the beginning of the trial stimulation. Processor 70 may generate the adaptive baseline state by determining the baseline state for a physiological signal prior to therapy delivery according to each tested therapy program.

After IMD 16 begins delivery of electrical stimulation to patient 14 based on the second therapy program, an amplitude of signal 98 increases, as shown in during stimulation period 94 in FIG. 5B, thereby indicating the presence of a stimulation effect from the delivery of therapy according to the second therapy program. The second therapy program differs from the first program in one or more respects. For example, the values of one or more therapy parameters of the second therapy program may differ from the values of the respective therapy parameters of the first therapy program. As examples, the first and second therapy programs may have different voltage or current amplitudes, signal durations, total stimulation period durations, or may define different electrode combinations for delivering therapy, and so forth. In addition, the first and second therapy programs may be delivered to different target tissue sites within patient 14. After termination of therapy delivery according to the second therapy program, physiological signal 98 remains at the elevated amplitude until time $T_4$. Thereafter, physiological signal 98 returns to a baseline state, which was established during pre-stimulation period 92.

The washout period $P_1$ associated with the second therapy program may be defined as the period between time $T_4$ and time $T_2$, i.e., the end of the stimulation period 94. The carryover effect shown by signal 98 in the example shown in FIG. 5B may be characterized as an immediate carryover effect because of its occurrence immediately after stimulation period 94. With some immediate carryover effects, such as the one seen in FIG. 5B, the change in physiological signal 98 is detected during stimulation period 94 and carries over into post-stimulation period 96, after IMD 16 terminates therapy delivery. In other embodiments, an immediate carryover effect may occur although physiological signal 98 did not change during stimulation period 94. Processor 70 may determine a characteristic of washout period $P_1$ during washout period $P_1$, such as the peak amplitude of signal 98 during washout period $P_1$, the average or median amplitude during washout period $P_1$, a waveform morphology (e.g., slope of the waveform or pattern in inflection points) during washout period $P_1$, and the like. In some embodiments, the one or more characteristics of washout period $P_1$ may be the duration of washout period $P_1$, which may be determined to be the duration of time between time $T_4$ and time $T_2$.

In some embodiments, processor 70 may determine a characteristic of stimulation period 94. The characteristic may include, for example, a duration or percentage of time a physiological signal 98 change from a baseline state was observed during stimulation period 94, or a trend in physiological signal 98 waveform during stimulation period 94, a power level of the physiological signal 98 measured in a particular frequency band during stimulation period 94, ratios of power levels between different frequency bands during stimulation period 94, and the like. The stimulation period characteristic may be used to evaluate the therapy program. For example, the stimulation period characteristic may indicate the affect of the therapy delivery on the physiological parameter of patient 12. In addition, in embodiments in which a plurality of therapy programs are tested, a stimulation period characteristic may be determined for each of the therapy programs and may be used to compare the efficacy of the therapy programs.

Figure 5C:
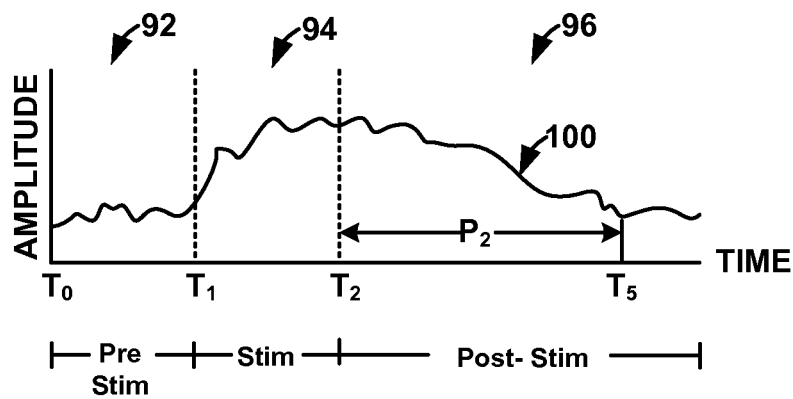

FIG. 5C illustrates a waveform of physiological signal 100 prior to, during, and after stimulation delivery according to a third therapy program that generates a stimulation effect and an immediate carryover effect. Again, a baseline state of physiological signal 100 may be established during a pre-stimulation period 92, prior to delivery of any stimulation by IMD 16 prior to delivery of stimulation according to the third therapy program in the case of an adaptive baseline state. After IMD 16 begins delivery of electrical stimulation to patient 14 based on the third therapy program, an amplitude of signal 100 increases, thereby indicating a stimulation effect from therapy delivery according to the third therapy program. After termination of therapy delivery according to the third therapy program at time $T_2$, physiological signal 100 remains above the baseline amplitude until time $T_5$.

Thereafter, physiological signal 100 returns to the baseline state, which was established generated during pre-stimulation period 92.

The washout period $P_2$ associated with the third therapy program may be defined as the period between time $T_5$ and time $T_2$, i.e., the end of the stimulation period 94. The carryover effect shown by signal 100 in the example shown in FIG. 5C may be characterized as an immediate carryover effect because of its occurrence immediately after stimulation period 94. The carryover effect resulting from therapy delivery by the third therapy program is longer than the carryover effect resulting from the second therapy program, shown in FIG. 5B, thus, the washout period $P_2$ shown in FIG. 5C has a longer duration than washout period $P_1$ shown in FIG. 5B.

Figure 5D:
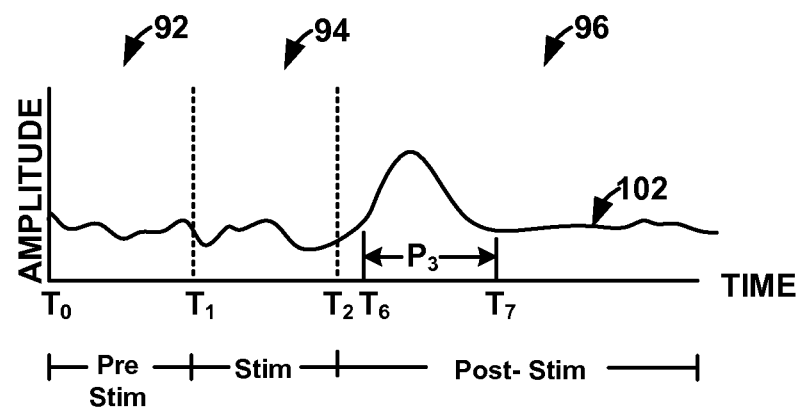

FIG. 5D illustrates a waveform of physiological signal 102 prior to, during, and after delivery of stimulation according to a fourth therapy program that does not generate a significant stimulation effect, but generates a carryover effect within patient 14. Again, a baseline waveform of physiological signal 102 may be established during a pre-stimulation period 92, prior to delivery of any stimulation by IMD 16 or prior to delivery of stimulation according to the fourth therapy program. After IMD 16 begins delivery of electrical stimulation to patient 14 based on the fourth therapy program, an amplitude of signal 102 remains substantially similar to the baseline state of stimulation signal 102, i.e., as shown by signal 102 during the pre-stimulation period 92 in FIG. 5A. This indicates that therapy delivery according the parameter values defined by the fourth therapy program does not generate a stimulation effect within patient 14. That is, the therapy delivery did not impact the physiological signal 102.

After termination of therapy delivery according to the fourth therapy program, physiological signal 102 remains at or below the baseline amplitude until time $T_6$, at which time the amplitude of the physiological signal 102 waveform increases. The increase in amplitude of the physiological signal 102 waveform during post-stimulation period 96 indicates that therapy delivery according to the fourth therapy program generated a carryover effect within patient 14. In addition, because the increase in amplitude of the physiological signal 102 waveform did not occur immediately after stimulation period 94, the carryover effect may be characterized as a delayed carryover effect. With a delayed carryover effect, the change in physiological signal 102 is detected during post-stimulation period 96, with or without prior detection of signal changes during stimulation period 94.

Physiological signal 102 returns to at or below the amplitude of the baseline signal generated during the pre-stimulation period 92 at time $T_7$. Accordingly, a washout period $P_3$ associated with the fourth therapy program may be defined as the duration between time $T_7$ and $T_2$. In other embodiments, washout period $P_3$ associated with the fourth therapy program may be defined as the duration between time $T_7$ and $T_6$, as shown in FIG. 5D, i.e., the actual duration of time at which physiological signal 102 differs from the baseline state.

Figure 5E:
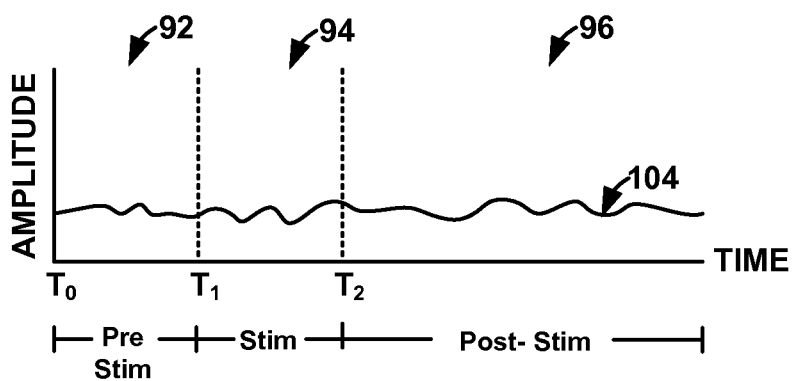

FIG. 5E illustrates a waveform of physiological signal 104 prior to, during, and after stimulation delivery according to a fifth therapy program that does not generate a stimulation effect or a carryover effect within patient 14. As FIG. 5E illustrates, physiological signal 104 remains substantially the same during pre-stimulation period 92, stimulation period 94, and post-stimulation period 96. The duration of a washout period associated with the fifth therapy program may be characterized as approximately 0 seconds.

The physiological signals 90 (FIG. 5A), 98 (FIG. 5B), 100 (FIG. 5C), 102 (FIG. 5D), and 104 (FIG. 5E) may be any suitable signal detectable within patient 14 that changes in response to delivery of therapy to patient 14, and indicates a physiological parameter of patient 14 that varies as a function of a patient mood state, such as an anxious state or a depressive state. Examples of suitable physiological signals include, but are not limited to, signals indicating a patient's heart rate, respiratory rate, ECG morphology, core temperature, electrodermal activity, EEG or ECoG activity, thermal sensing or facial EMG activity.

While the examples of stimulation effects and carryover effects in FIGS. 5B-5D illustrate an increase in an amplitude of a physiological signal during stimulation period 94 and/or during post-stimulation period 96, in some embodiments, the physiological signal may decrease in amplitude relative to the baseline state during at least one of the stimulation period 94 or post-stimulation period 96. Accordingly, if the physiological signal returns to a baseline state, the signal may increase in value.

Figure 6:
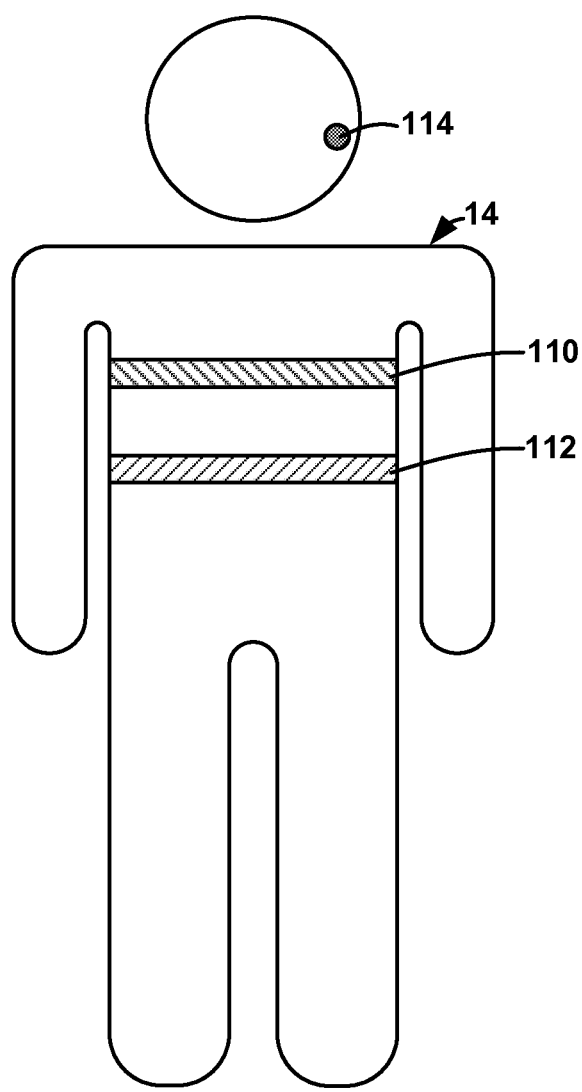
FIG. 6 is a schematic diagram illustrating example external sensing devices that may be used to monitor a physiological parameter of a patient.

FIG. 6 is a schematic diagram illustrating different examples embodiments of sensing module 26 (FIG. 1) that may be used to monitor a physiological parameter of patient 14 in order to detect a carryover effect from therapy delivery. As indicated above with respect to FIG. 1, signals generated by sensing module 26, which may be implanted or external to patient 14, may be transmitted to IMD 16 or at least one of programmers 22, 24 via wireless signals or a wired connection. IMD 16 or programmers 22, 24 may monitor and analyze the signals from sensing module 26 to detect a carryover effect from therapy delivery, and determine one or more characteristics of a washout period following active therapy delivery.

In some embodiments, sensing module 26 may include ECG electrodes, which may be carried by an ECG belt 110. ECG belt 110 incorporates a plurality of electrodes for sensing the electrical activity of the heart of patient 14. In the embodiment shown in FIG. 6, ECG belt 110 is worn by patient 14. The heart rate and, in some embodiments, ECG morphology of patient 14 may be monitored based on the signal provided by ECG belt 110. Examples of suitable ECG belts for sensing the heart rate of patient 14 are the "M" and "F" heart rate monitor models commercially available from Polar Electro OY of Kempele, Finland. In some embodiments, instead of ECG belt 110, patient 14 may wear a plurality of ECG electrodes (not shown in FIG. 6) attached, e.g., via adhesive patches, at various locations on the chest of patient 14. An ECG signal derived from the signals sensed by such an array of electrodes may enable both heart rate and ECG morphology monitoring, as is known in the art. In addition to or instead of ECG belt 110, IMD 16 may sense the patient's heart rate, e.g., using electrodes on a housing of IMD 16, electrodes of leads 20, electrodes coupled to other leads or any combination thereof.

In other embodiments, sensing module 26 may include a respiration belt 112 that outputs a signal that varies as a function of respiration of the patient may also be worn by patient 14 to monitor activity to determine whether patient 14 is in a particular mood state or to determine the stimulation or carryover effects of therapy delivery on patient 14. For example, in an anxious mood state, the patient's respiration rate may increase relative to a baseline respiration rate associated with a non-anxious mood state of patient 14. Respiration belt 112 may be a plethysmograpy belt, and the signal output by respiration belt 112 may vary as a function of the changes is the thoracic or abdominal circumference of patient 14 that accompany breathing by patient 14. An example of a suitable respiration belt is the TSD201 Respiratory Effort Transducer commercially available from Biopac Systems, Inc. of Goleta, Calif. Alternatively, respiration belt 112 may incorporate or be replaced by a plurality of electrodes that direct an electrical signal through the thorax of patient 14, and circuitry to sense the impedance of the thorax, which varies as a function of respiration of patient 14, based on the signal. The respiration belt may, for example, be used to generate an impedance cardiograph (ICG), which detects properties of blood flow in the thorax. In some embodiments, the ECG and respiration belts 110, 112 may be a common belt worn by patient 14.

In some embodiments, sensing module 26 may also include electrode 114, which may be a surface electrode or intramuscular electrode. Electrode 114 may be positioned to monitor muscle activity (e.g., EMG), the temperature of the patient's facial skin (e.g., a thermal sensing electrode), or the moisture level of the patient's skin (e.g., via electrodermal activity). Alternatively, electrode 114 may be positioned to monitor the muscle activity, temperature, moisture level or extent of perfusion of other regions of the patient's body, such as an arm, leg or torso. Electrode 114 may be coupled to clinician programmer 22, or another device, which may monitor the signals generated by electrode 114 as a function of the physiological parameter and transmit the signals to clinician programmer 22. Each of the types of sensing device 110, 112, and 114 described above may be used alone or in combination with each other, as well as in addition to other sensing devices.

During a programming session during which IMD 16 delivers therapy to patient 14 according to a plurality of therapy programs, it may be desirable to time the trialing of the different therapy programs such that one or more carryover effects from stimulation delivery according to the prior-trialed therapy program have substantially dissipated. That is, during a programming session, it may be desirable to determine the times at which different therapy programs should be applied, and the time intervals between successive programs based on one or more carryover effects.

Waiting to deliver trial stimulation according to a particular therapy program until after one or more carryover effects from a prior-trialed therapy program may help reduce or even eliminate contamination between therapy programs. For example, with respect to the example of FIG. 5B, which illustrates physiological signal 98 prior to, during, and after stimulation delivery according to a second therapy program, it may be undesirable to initiate therapy delivery according to a different therapy program until after time $T_4$, which indicates the end of the washout period and the time at which carryover effects from therapy delivery according to the second therapy program have substantially dissipated. Initiating therapy delivery according to a different therapy program between times $T_2$ and $T_4$ may result in inaccurate therapeutic effects on patient 14 due to lingering carryover effects from the previous therapy program. For example, the amplitude increase of physiological signal 98 occurring between times $T_2$ and $T_4$ may result in an increased amplitude of physiological signal 98 in response to the therapy delivery by the subsequently-trialed therapy program due to cumulative or interactive effects of the stimulation from the therapy programs.

Figure 7A:
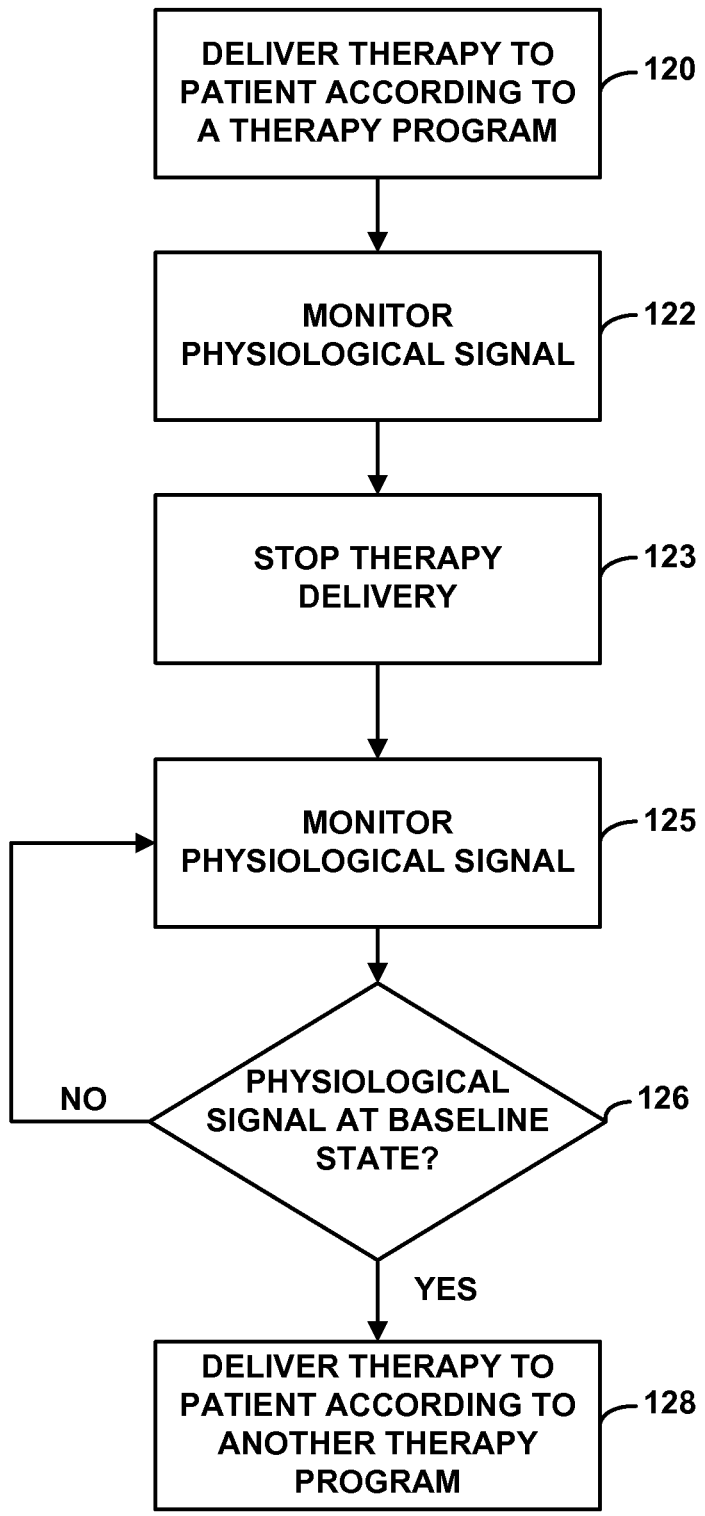
FIGS. 7A-7C are flow diagrams illustrating example techniques for timing delivery of therapy according to different therapy programs during a programming session.

FIG. 7A is a flow diagram illustrating an example technique for automatically timing delivery of therapy programs during a programming session based on the duration of a washout period. The automatic technique for timing trials of therapy delivery may more accurately and precisely time trials of different therapy programs to help reduce contamination between the stimulation and post-stimulation effects of the trialed therapy programs compared to a technique in which a clinician manually monitors a physiological signal of patient 14 or manually observes patient 14 to estimate when one or more carryover effects from a trialed therapy program have substantially dissipated.

The manual techniques for timing the delivery of therapy programs during a trial period are susceptible to human error. For example, as previously indicated, in some cases, a baseline state of a physiological signal may change during a programming session. While processor 70 of clinician programmer 22 may readily adapt the baseline state of the physiological signal to the patient's current condition, a clinician may find it difficult, cumbersome or time-consuming to continually monitor the patient's baseline state. As another example, the clinician may not be able to easily manually observe subtle changes to a physiological signal during stimulation period 94 and post-stimulation period 96. Processor 70 implements various algorithms to compare the physiological signal waveform to a threshold value or pattern template in order to detect a stimulation effect or carryover effect. Accordingly, the clinician may not detect the subtle changes to a physiological signal through visual observation that processor 70 may be to detect with the comparison algorithms. Changes to physiological signals that indicate a change to a patient's mood state may be subtle.

Figure 7B:
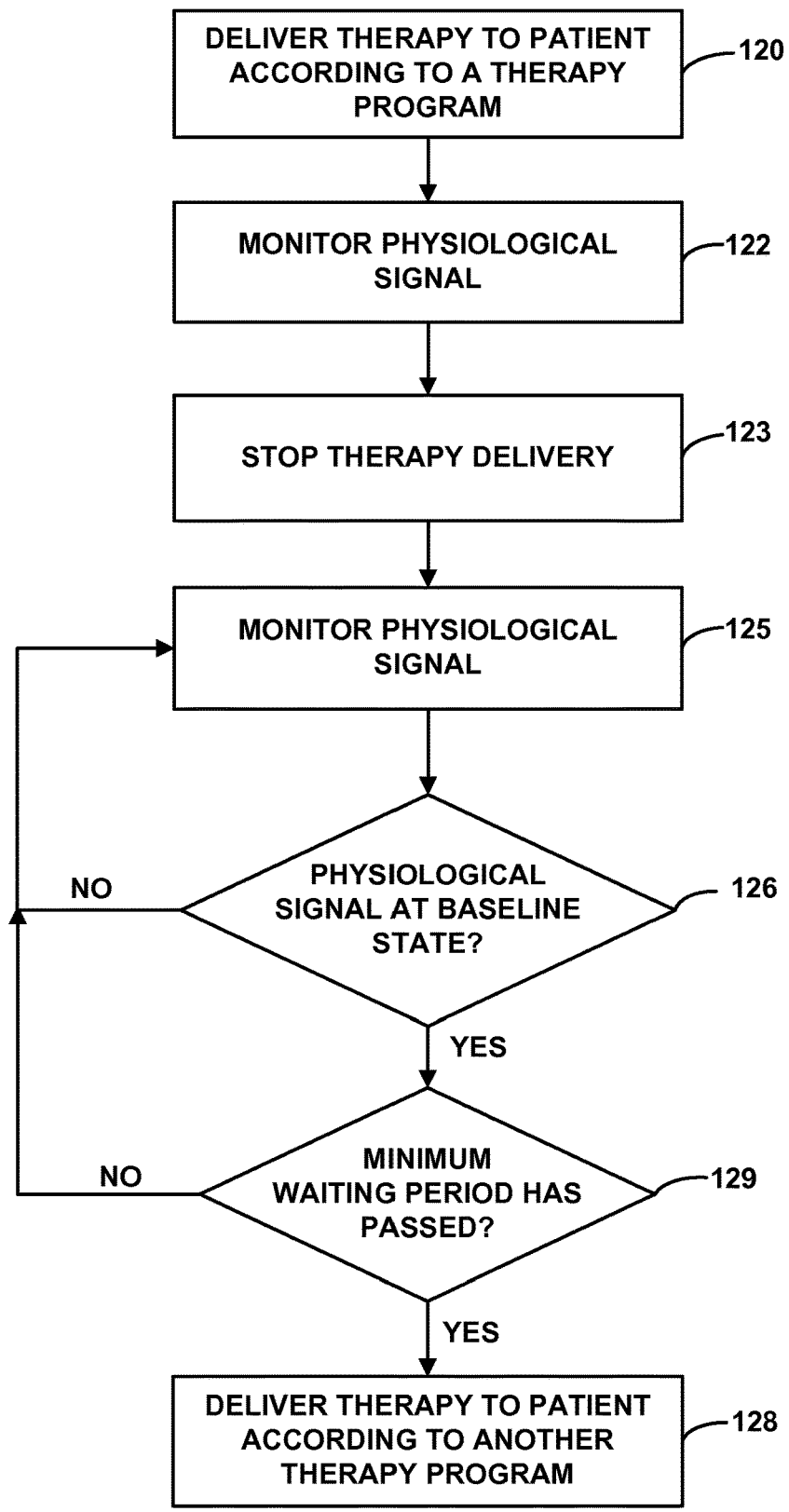
Figure 7C:
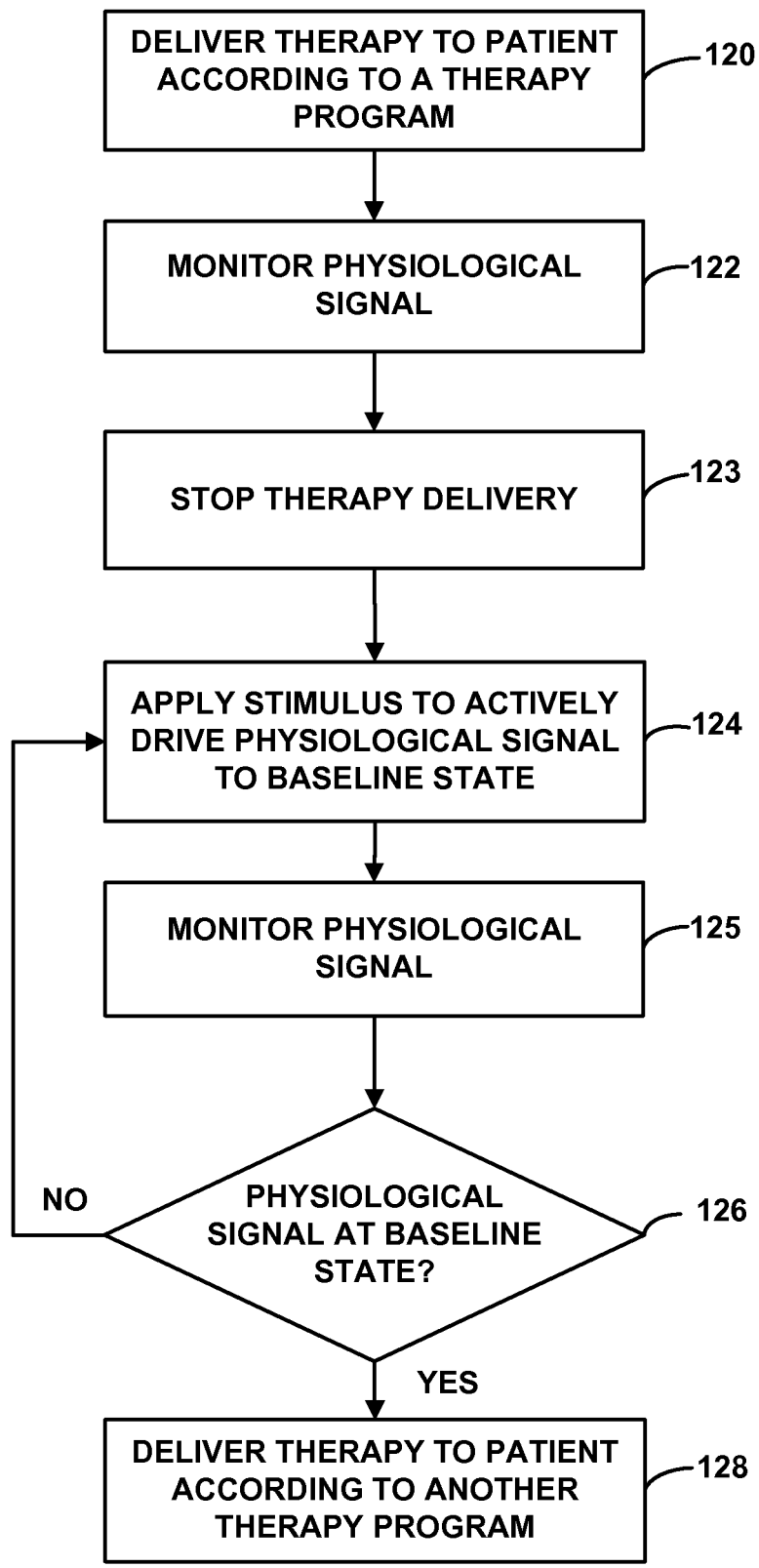

While clinician programmer 22 and its processor 70 are primarily referred to throughout the description of FIGS. 7A-7C, as well as FIGS. 8-16, in other embodiments, processor 40 of patient programmer 24 or a processor of another device may perform any of the techniques described with respect to FIG. 7A or any of the other figures. Under the control of a clinician, e.g., via clinician programmer 22, processor 34 of IMD 16 may control therapy module 32 to deliver electrical stimulation therapy to patient 14 according to the stimulation parameter values defined by a therapy program (120). For example, the clinician may select the therapy program from a list of therapy programs stored in clinician programmer 22 (FIG. 3) by interacting with user interface 74. Processor 70 of clinician programmer 22 may then transmit a control signal to processor 34 of IMD 16 by the telemetry module 76 of clinician programmer 22. The control signal may set forth the parameter values of the therapy program or may merely be an identifier associated with the therapy program, and the actual parameter values may be stored within memory 35 of IMD 16 and associated with the identifier in memory 35.

As an alternative to a clinician-selected therapy program, processor 70 of programmer 22 may automatically select the parameter values for the therapy program. For example, processor 70 may implement a methodical system of identifying potentially beneficial therapy parameter values for patient 14. In one embodiment, processor 70 may implement a tree-based technique for selecting the therapy program. A programming tree structure may include a plurality of levels that are associated with a different therapy parameter. The tree may include nodes that are connected to nodes of adjacent levels, whereby each node defines values for at least one therapy parameter. A clinician or patient 14 may interact with processor 70 via user interface 74 in order to create a program path by moving through one node at each level of the tree according to efficacy feedback from patient 14 and/or one or more sensors that detect physiological parameters of patient 14.

Examples of tree-based techniques for modifying a therapy program or generating a new therapy program are described in commonly-assigned U.S. patent application Ser. No. 11/799,114 to Gerber et al., entitled, "TREE-BASED ELECTRICAL STIMULATION PROGRAMMING FOR PAIN THERAPY," and filed on Apr. 30, 2007; commonly-assigned U.S. patent application Ser. No. 11/799,113 to Gerber et al., entitled, "TREE-BASED ELECTRICAL STIMULATOR PROGRAMMING," and filed on Apr. 30, 2007; and commonly-assigned U.S. patent application Ser. No. 11/414,527 to Gerber et al., entitled, "TREE-BASED ELECTRICAL STIMULATOR PROGRAMMING," and filed on Apr. 28, 2006, which are each incorporated herein by reference in their entireties.

In another embodiment, processor 70 may implement a genetic algorithm-based technique for selecting the therapy program, such as the one described in commonly-assigned U.S. Pat. No. 7,239,926 to Goetz et al., entitled, "SELECTION OF NEUROSTIMULATION PARAMETER CONFIGURATIONS USING GENETIC ALGORITHMS," which issued on Jul. 3, 2007 and is incorporated herein by reference in its entirety. In one embodiment described in U.S. Pat. No. 7,239,926 to Goetz et al., genetic algorithms guide the selection of stimulation parameter values by suggesting the parameter values that are most likely to be efficacious given the results of tests already performed during an evaluation (or programming) session. Genetic algorithms encode potential solutions to a problem as members of a population of solutions. This population is then judged based on a fitness function. The best performers, i.e., the best fit solutions, are then retained and a new generation is created based upon their characteristics. The new generation is composed of solutions similar in nature to the best performers of the previous generation.

Other suitable techniques for selecting a therapy program include the decision-tree based techniques described in commonly-assigned U.S. patent application Ser. No. 10/767,545 to Goetz, entitled, "SELECTION OF NEUROSTIMULATOR PARAMETER CONFIGURATIONS USING DECISION TREES," which was filed on Jan. 29, 2004, and U.S. Pat. No. 6,901,754 to Goetz, entitled, "SELECTION OF NEUROSTIMULATOR PARAMETER CONFIGURATIONS USING BAYESIAN NETWORKS," which was filed on Jan. 29, 2004. The entire content of U.S. patent application Ser. No. 10/767,545 and U.S. Pat. No. 6,901,754 is incorporated herein. As described in U.S. patent application Ser. No. 10/767,545 to Goetz, a parameter configuration search algorithm may be used to guide the clinician and/or processor 70 in the selection of parameter configurations for a therapy program. The search algorithm relies on a decision tree to identify potential optimum parameter configurations, where the decision tree interactively guides the clinician by suggesting the configurations that are most likely to be efficacious given the results of determinations along the path of the decision tree based on efficacy observations already performed during an evaluation session.

As described in U.S. Pat. No. 6,901,754 to Goetz, processor 70 or a clinician may execute a parameter configuration search algorithm that relies on a Bayesian network structure that encodes conditional probabilities describing different states of the parameter configuration. The Bayesian network structure may provide a conditional probability table that represents causal relationships between different parameter configurations and clinical outcomes. The search algorithm uses the Bayesian network structure to infer likely efficacies of possible parameter configurations based on the efficacies of parameter configurations already observed.

Processor 70 may monitor one or more physiological signals of patient 14 (122) at least during the stimulation period, and, in some cases, prior to the stimulation period to determine a baseline physiological parameter state. During the trial therapy session, processor 70 may control IMD 16 to deliver therapy to patient 14 according to the therapy program for a limited period of time. For example, after about 20 seconds to about 60 minutes, such as about 30 seconds to about one minute, processor 70 may control IMD 16 to stop therapy delivery (123). Alternatively, IMD 16 may be preprogrammed to automatically stop therapy delivery (123) independently of any clinician programmer 22 or clinician control. As another alternative, processor 60 may generate a prompt for the clinician to take an action or approve an action.

After IMD 16 has stopped therapy delivery according to the trialed therapy program (123), processor 70 of programmer 22 may continue monitoring the physiological signal during the post-stimulation period until the monitored physiological signal returns to a particular state, which may be the baseline state (125, 126), thereby indicating one or more carryover effects from the therapy delivery have substantially terminated. The baseline state may be stored in memory 72 (FIG. 4) of clinician programmer 22 or a memory of another device. The baseline state may be an exact baseline value of the physiological signal at the time prior to the stimulation period, or may be a value substantially close to the baseline value, such as within certain percentage (e.g., within about 5% to about 25%, depending on the type of signal). For example, in some cases, the physiological signal may return to the baseline state (125, 126), but may have an average amplitude value that is greater than the amplitude value prior to the stimulation period. In other embodiments, processor 70 of programmer 22 may determine when the physiological signal returns to another state, which may be selected by the clinician and may or may not be based on the baseline state. In some embodiments, the state may be defined as a single value or a range of values.

As previously indicated, processor 70 may determine the baseline state of the relevant physiological signal prior to therapy delivery according to the trialed therapy program (120) or prior to any therapy delivery by IMD 16. Processor 70 may determine whether the signal returned to a baseline state using different techniques, which may depend on the physiological signal characteristic that characterizes the baseline state of the signal.

In embodiments in which the baseline state of the physiological signal is characterized by a peak amplitude value, average amplitude value, mean amplitude value or another amplitude value, processor 70 may compare the amplitude value of the physiological signal to the relevant amplitude value, which may be stored as a threshold value in memory 72. Rather than continuously comparing the amplitude of the physiological signal, processor 70 may sample the physiological signal during the post-stimulation period 96 (FIGS. 5A-5E) and average the amplitude of the physiological signal for each sampled period, which may be, e.g., a few milliseconds or a few seconds in duration.

In embodiments in which the baseline state of the physiological signal is characterized by a trend in the physiological signal waveform, processor 70 may compare a trend in the physiological signal during the post-stimulation period 96 (FIGS. 5A-5E) to a template stored in memory 72. A similar technique for comparing the physiological signal waveform to a template is described below with respect to FIG. 14. In embodiments in which the baseline state of the physiological signal is characterized by a frequency band characteristic of the physiological signal waveform, such as an energy level in a frequency band or a ratio of energy levels in more than one frequency band, processor 70 may compare the relevant frequency band characteristics of the physiological signal waveform during the post-stimulation period 96 (FIGS. 5A-5E) to a template or threshold value stored in memory 72. A similar technique for analyzing a frequency band characteristic of a physiological signal waveform is described below with respect to FIG. 15.

If processor 70 determines that the physiological signal has not returned to the baseline state (126), processor 70 may continue monitoring the physiological signal (125) until the signal returns to the baseline state, thereby indicating that one or more carryover effects from therapy delivery according to the therapy program have substantially dissipated. On the other hand, if processor 70 determines that the physiological signal has returned to the baseline state (126), processor 70 may initiate the delivery of trial stimulation according to another therapy program (128). Again, processor 70 may automatically initiate the trialing of another therapy program or may initiate the therapy delivery according to another therapy program after providing a notification to a clinician and receiving approval from the clinician to proceed to the next therapy program.

For example, in the example shown in FIG. 5A, for example, physiological signal 90 returns to the baseline state during stimulation period 94 and there is substantially no carryover effect, and, therefore, processor 70 may automatically determine that the physiological signal 90 is at the baseline state approximately immediately following the cessation of therapy delivery. As another example, in the example shown in FIG. 5B, processor 70 may automatically determine that physiological signal 98 returns to the baseline state at approximately time T$_4$, which occurs after the end of the stimulation period 94 and denotes the end of the washout period P$_1$. With respect to delayed carryover effects, as shown with respect to physiological signal 102 in FIG. 5D, processor 70 may continue monitoring physiological signal 102 for a period of time following stimulation period 94 in order to detect the delayed carryover effect. In the example shown in FIG. 5D, processor 70 may automatically determine that physiological signal 98 returns to the baseline at approximately time T$_7$.

Processor 70 may control IMD 16 to delivery therapy according to another therapy program (i.e., a "next-trialed" therapy program) (128). In some embodiments, processor 70 may generate an indication to the clinician that the next therapy program may be trialed, e.g., by a visible (e.g., a green light that lights up), audible, or somatosensory indication (e.g., a vibration). The clinician may then select a therapy program to test and processor 70 may control IMD 16 to delivery therapy according to the clinician-selected therapy program.

As another example, the clinician may provide input indicating approval for processor 70 to automatically select another therapy program to test. Alternatively, processor 70 may generate the indication that the next therapy program may be tested and automatically select another therapy program to test. The indication may, therefore, be an indication that another therapy program is being tested in addition to being an indication that one or more carryover effects from the prior-trialed therapy program have substantially dissipated. As with the prior-trialed therapy program, the clinician or processor 70 may select the next-trialed therapy program from a list of therapy programs stored in clinician programmer 22 (FIG. 3) by interacting with user interface 44, or processor 70 of clinician programmer 22 may automatically select the second therapy program. The therapy parameter values for the second therapy program may be stored within IMD 16 and/or within clinician programmer 22.

In one embodiment, as described by U.S. Pat. No. 7,239,926 to Goetz et al., processor 70 may receive an indication of observed efficacy of the prior-trialed therapy program, and select another therapy program for IMD 16 based on the indication of observed efficacy and a genetic algorithm. A genetic algorithm may suggest cross-over between different solutions identified by the genetic algorithm or mutation of one or more solutions identified by the genetic algorithm, or random electrode changes.

FIG. 7B is a flow diagram illustrating another example technique for automatically timing delivery of therapy programs during a programming session based on the duration of a washout period. Just as with the technique shown in FIG. 7A, therapy may be delivered to patient 14 according to a therapy program (120), and processor 70 may monitor a physiological signal of patient that changes as the mood state of patient 14 changes (122). Upon the cessation of therapy delivery according to the therapy program (123), processor 70 may determine whether the physiological signal has returned to the baseline state (126). If the physiological signal has not returned to the baseline state, processor 70 may continue monitoring the physiological signal (125).

If the physiological signal has returned to the baseline state, processor 70 may determine whether a minimum waiting period has passed (129). The minimum waiting period may be, for example, a minimum period of time following the end of the stimulation period 94 for the trial therapy delivery according to the therapy program. The minimum waiting period may be selected by the clinician or may be pre-programmed into clinician programmer 22, e.g., by the manufacturer or distributor of IMD 16 or programmer 22. For example, the minimum waiting period may be minimum desired spacing between the trial sessions for different therapy programs.

If the minimum waiting period has passed, processor 70 may initiate therapy delivery to patient 14 according to another therapy program (128). If the minimum waiting period has not passed, processor 70 may continue monitoring the physiological signal (125) and determine whether the signal is at the baseline state (126) until the minimum waiting period has passed (129) prior to initiating therapy delivery according to the next trialed therapy program (128). Processor 70 may continue comparing the physiological signal to the baseline state in order to detect one or more delayed carryover effects. Timing the trialing of therapy programs using a minimum waiting period may help regulate the rate at which processor 70 switches between therapy programs during the programming session, and helps minimize the possibility that processor 70 will not detect a delayed carryover effect.

FIG. 7C is a flow diagram illustrating another example technique for automatically timing delivery of therapy programs during a programming session based on the duration of a washout period. Therapy may be delivered to patient 14 according to a therapy program (120), and processor 70 may monitor a physiological signal of patient that changes as the mood state of patient 14 changes (122). Upon the cessation of therapy delivery according to the therapy program (123), processor 70 may control the application of a stimulus to actively drive of the physiological signal to a baseline state (124). The physiological signal may be actively driven to the baseline state using any technique that increases the speed at which the physiological signal returns to the baseline state compared to the passive return to the baseline state, i.e., without substantial interference from an external stimulus.

For example, in embodiments in which therapy system 10 is used to manage a MDD of patient 14, processor 70 may present an unpleasant or distressing image (e.g., a picture or video) to patient 14 via display 60 (FIG. 4) of clinician programmer 20 or prompt the clinician or another user to present the unpleasant image to patient 14. As another example, IMD 16 may deliver electrical stimulation to patient 14 to cause the physiological signal to return to a baseline state. For example, in embodiments in which a therapy system is used to manage pain of patient 14 (e.g., in the case of spinal cord stimulation), IMD 16 may provide stimulation to patient 14 to cause pain or processor 70 may prompt patient 14 to engage an activity that is known to cause patient 14 pain. Other techniques for expressly driving the physiological signal to a baseline state are contemplated, and may be dependent on the type of patient condition the therapy system is used to manage.

After the attempt to actively drive the physiological signal to the baseline state, processor 70 may determine whether the physiological signal has returned to the baseline state (126). If the physiological signal has not returned to the baseline state, processor 70 may control the application of another stimulus to attempt to actively drive the physiological signal to the baseline state (124). If the physiological signal has returned to the baseline state, processor 70 may initiate the delivery of therapy to patient 14 according to another therapy program (128). In some embodiments, processor 70 may also wait the minimum wait period (as discussed with respect to FIG. 7B) prior to initiating therapy delivery according to the next-trialed therapy program.

Determining the times at which different therapy programs should be applied, and the time intervals between successive programs based on one or more carryover effects may be used to time the testing of therapy programs for other types of therapy applications. Accordingly, the techniques shown in FIGS. 7A-7C are applicable to many types of therapy systems 10 in addition to or instead of DBS system 10 shown in FIG. 1.

In some cases, a washout period may be used to track the effects of DBS (or other types of therapy) on sensed physiological parameters of patient 14 and identify one or more carryover effects from the stimulation. In the case of therapy used to manage a psychiatric disorder of patient 14, the physiological parameters may indicate changes in the patient's mood state. For example, a change in the patient's respiratory rate, heart rate, and galvanic skin response may indicate changes in the patient's overall arousal level or anxiety level. As another example, a change in the patient's facial expression (e.g., monitored by EMG) or facial flushing (e.g., monitored by thermal sensing) may indicate a change in an mood state. Changes in the patient's EEG or ECoG signal, detected by template matching, peak detection, comparison to a threshold amplitude or energy level value may, may also indicate a change in the patient's mood state. An example technique for performing template matching between the physiological signal waveform and a template waveform is described below with reference to FIG. 14.

In some embodiments, changes to a patient's mood state during the washout period, i.e., in response to therapy delivery may be indicative of the efficacy of therapy, while in other embodiments, changes to the patient's mood state may be indicative of an undesirable response to the therapy delivery. For example, if therapy system 10 provides therapy to patient 14 to manage MDD, a slight increase in emotional arousal indicated by a physiological parameter of patient 14 during the washout period may indicate a positive response to the therapy. On the other hand, if therapy system 10 provides therapy to patient 14 to manage an anxiety disorder, a slight increase in emotional arousal during the washout period may indicate a negative response to therapy because the increase in emotional arousal may suggest an increase in the patient's anxiety level.

Changes in a physiological parameter of patient 14 that is suggestive of the patient's mood state may be assessed by monitoring the physiological signal during pre-stimulation period 92, stimulation period 94, and post-stimulation period 96 (FIGS. 5A-5E). As described above, the time windows for pre-stimulation period 92, stimulation period 94, and post-stimulation period 96 may be fixed or may be defined by the clinician, e.g., based on the actually time periods during which the delivery of electrical stimulation therapy begins and ends.

Figure 8:
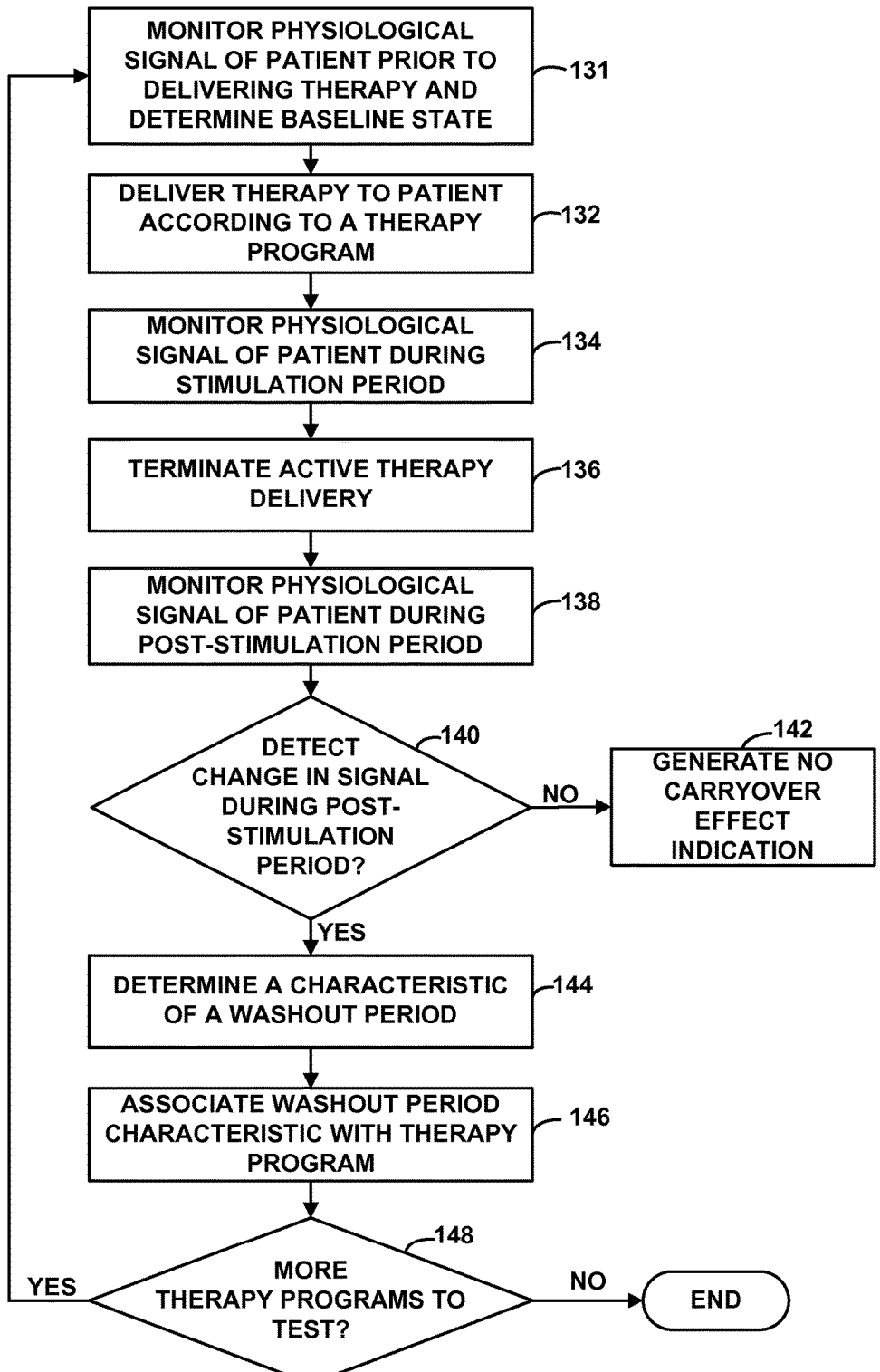
FIG. 8 is a flow diagram illustrating a technique for automatically determining a characteristic of a washout period following therapy delivery according to a therapy program and associating the washout period characteristic with the therapy program.

FIG. 8 is a flow diagram illustrating an example technique for automatically determining a characteristic of a washout period following therapy delivery by a therapy program and associating the washout period characteristic with the therapy program. The characteristic of the washout period may be used to evaluate the efficacy of the therapy program. Examples of suitable washout period characteristics include, but are not limited to, a duration of the washout period, an amplitude of the physiological signal waveform during the washout period, a trend in the physiological signal waveform during the washout period, a power level of the physiological signal measured in a particular frequency band of the physiological signal waveform, ratios of power levels between different frequency bands, and the like. While psychiatric disorder therapy is primarily referred to in the description of FIG. 8, as well as FIGS. 9-10, in other embodiments, therapy programs for managing other patient conditions may be evaluated and ordered based on washout period characteristics.

Prior to delivering electrical stimulation therapy (or another type of therapy) to patient 14 according to a therapy program, processor 70 may monitor a physiological parameter of patient 14 (131). For example, processor 70 may receive input from sensing module 26 (FIG. 1) during the pre-stimulation period 92 (FIGS. 5A-5E). Processor 70 may determine a baseline state for the monitored physiological signal, e.g., by selecting an amplitude value or waveform trend during the pre-stimulation period 92 (131). In one embodiment, processor 70 determines an average or median amplitude of the physiological signal waveform during the pre-stimulation period 92, which may be a predetermined period of time prior to therapy delivery, such as about 30 seconds to about 10 minutes, and sets the average or median amplitude as a baseline amplitude value. Other time ranges for the pre-stimulation period 92 are also contemplated. In another embodiment, processor 70 may determine the peak amplitude value of the physiological signal waveform during the pre-stimulation period, and set the peak amplitude value as the baseline value. In other embodiments, processor 70 may determine a trend of the physiological signal waveform during the pre-stimulation period, and set the trend as a baseline waveform.

Processor 70 may control IMD 16 to deliver therapy to patient 14 according to a therapy program (132), which may be clinician-selected or automatically selected by clinician programmer 22. Processor 70 may monitor one or more physiological signals of patient 14 during the stimulation period 94 (FIGS. 5A-5E) (134). For example, processor 70 may determine whether the therapy delivery had a stimulation effect on patient 14 by comparing the physiological signal sensed during stimulation period 94 to the baseline state. As one example, if the peak amplitude of the physiological signal waveform during the stimulation period 94 exceeds a baseline amplitude value, the physiological signal may indicate that the therapy delivery according to the therapy program had an effect on patient 14.

Processor 70 may control IMD 16 to terminate active therapy delivery (136). In some embodiments, IMD 16 may be preprogrammed to actively deliver electrical stimulation signals to patient 14 for a predetermined time period, such as about 1 minute to about 60 minutes, although other stimulation period durations are contemplated. Thus, in some embodiments, IMD 16 may automatically terminate active therapy delivery independently of any control by clinician programmer 22. Processor 70 may monitor the physiological signal during the post-stimulation period 96 (FIGS. 5A-5E) (138) and determine whether the physiological signal changed from the baseline state during the post-stimulation period 96, e.g., by comparing one or more characteristics of the physiological signal sensed during the post-stimulation period 96 to the baseline state established during the pre-stimulation period 92 (140). If processor 70 does not detect a change in the physiological signal from the baseline state during the post-stimulation period 96 (140), processor 70 may generate an indication that indicates the therapy delivery according to the therapy program did not result in a carryover effect (142). The no carryover effect indication may be a value, flag or signal that is stored in memory 72 (FIG. 4) of clinician programmer 22 and associated with the therapy program.

If the baseline state is characterized by a threshold amplitude value, processor 70 may compare a peak, average, median or any other amplitude value of the signal during a the post-stimulation period 96 to a baseline amplitude value in order to determine whether the physiological signal differs from the baseline state during the post-stimulation period 96. The peak, average, median or other amplitude value that is compared to the baseline amplitude value may be the amplitude value during a particular time range following the stimulation period 94. For example, processor 70 may compare the peak, average or median amplitude value of the physiological signal during a one minute period following stimulation period 94 to the baseline amplitude value. The time period may be selected by the clinician, and may be long enough to confirm that there are no delayed carryover effects from the therapy delivery.

In other embodiments, processor 70 may determine whether the physiological signal differs from the baseline by comparing a trend in the physiological signal during the particular time range of the post-stimulation period to a template. For example, processor 70 may compare the physiological signal during the particular time range following the stimulation period 94 to a template to determine whether the physiological signal differs from the baseline. In one embodiment, processor 70 implements a temporal correlation technique, during which processor 70 samples the physiological signal with a sliding window and compares the sample to a template to determine whether the sampled signal correlates well with the template. For example, processor 70 may perform a correlation analysis by moving a window along a digitized plot of the amplitude of the measured physiological signals at regular intervals following the stimulation period 94, such as between about one millisecond to about one second intervals, to define a sample of the physiological signal. The sample window may be slid along the plot of the physiological signal waveform until a correlation is detected between the waveform of the baseline template and the waveform of the sample of the physiological defined by the window.

By moving the window at regular time intervals, multiple sample periods are defined. The correlation may be detected by, for example, matching multiple points between the template waveform and the waveform of the plot of the physiological signal over time, or by applying any suitable mathematical correlation algorithm between the sample in the sampling window and a corresponding set of samples stored in the template waveform. As examples, if rate of change (i.e., the slope) of the monitored physiological signal immediately following the stimulation period 94 correlates to the slope of a trend template, the physiological signal may indicate a lack of a carryover effect from the therapy delivery. As another example, if inflection points in the physiological signal waveform substantially correlate to a template immediately following stimulation period 94, the physiological signal may indicate a lack of a carryover effect from the therapy delivery.

In another embodiment, processor 70 implements a frequency correlation technique, during which processor 70 analyzes the physiological signal in the frequency domain to compare selected frequency components of the sensed physiological signal to corresponding frequency components of the template signal. In each of the embodiments described above, the one or more templates or baseline amplitude values may be stored within memory 72 of clinician programmer 22 or another device.

If processor 70 detects a change in the physiological signal from the baseline value or waveform during the post-stimulation period (140), processor 70 may determine a characteristic of a washout period (144). The washout period indicates the period during the post-stimulation period 96 in which a carryover effect from delivery of therapy according to the therapy program is observed, which may be determined by comparing the physiological signal to the baseline state. The washout period may be the period during which the physiological signal substantially differs from the baseline state by at least a threshold amount.

In one embodiment, the characteristic of the washout period may include the duration of the washout period. Processor 70 may determine the duration of the washout period by determining when the physiological signal returns to the baseline state during the post-stimulation period 96. The duration of the washout period may then be the duration of time between the end of stimulation period 94 (e.g., when IMD 16 terminates therapy delivery or when the final electrical stimulation signal according to the therapy program is delivered) and the time at which the physiological signal returns to the baseline state. In some situations in which the physiological parameter indicates a delayed carryover effect, processor 70 may determine the duration of the washout period by determining when processor 70 determined that the physiological signal differs from the baseline state during the post-stimulation period 96 and when the signal returns to the baseline state during the post-stimulation period 96. However, as previously discussed, in some cases, despite the presence of a delayed carryover effect, a duration of a washout period may be considered to be the duration of time between the end of stimulation period 94 and the time at which the signal returns to the baseline state.

In other embodiments, the characteristic of the washout period may include the peak amplitude value, average amplitude, median amplitude value or any other amplitude value of the physiological signal during the washout period. The characteristic of the washout period may also be a pattern in the physiological signal waveform over time, such as a slope or trend in the inflection points, or one or more frequency band components of the physiological signal. In some cases, processor 70 may determine more than one characteristic of the washout period.

After determining the one or more characteristics of the washout period (144), processor 146 may associate the determined washout period characteristic with the therapy program (146) and store the characteristic in memory 72 (FIG. 4) of clinician programmer 22 or another device, such as patient programmer 24, IMD 16 or a different device. If there are more therapy programs to test during the trialing session (148), processor 70 may establish another baseline for the pre-stimulation period prior to delivery of therapy according to the next-trialed therapy program (131), and repeat the process to establish one or more washout period characteristics for the next-trialed therapy program. Alternatively, processor 70 may utilize a previously established baseline. If there are no more therapy programs to test, processor 70 may not take any further action with respect to determining washout period characteristics associated with trialed therapy programs.

Changes in a physiological signal during the post-stimulation period 96 may be desirable or undesirable, depending on the type of response to the therapy program that is evoked, as well as the intended outcome of the therapy delivery. For example, slight increases in emotional arousal caused by stimulation may be beneficial to a patient with MDD, if it does not interfere with normal function or cause the patient to achieve an emotional state not considered normal (e.g., elation, hypomania). Similarly, a decrease in emotional arousal may be desired in patients engaged in compulsions to reduce anxiety, such as with OCD. In other instances, the observed change may be unwanted, and represent a transient or adverse event. In such cases, the goal of determining the washout period characteristics associated with therapy delivery according to a plurality of therapy programs would be to test and identify therapy programs that produce minimal or no changes in the physiological signal(s).

A washout period characteristic may be determined for more than one segment of the washout period. For example, processor 70 may determine the peak amplitude of the physiological signal for every 5 ms segment of time until the physiological signal returns to the baseline state. This may enable processor 70 to verify the return of the amplitude of the physiological signal to the baseline amplitude is not temporary, i.e., that the physiological signal does not subsequently increase in amplitude following a return of the signal to the baseline state. In addition, determining the washout period characteristic for sequential segments of the washout period may be useful for determining a trend in the washout period relatively quickly, e.g., by establishing specific points in the trend during the washout period.

In some embodiments, processor 70 may monitor more than one physiological parameter of patient 14 to determine effects of the therapy on patient 14. Accordingly, processor 70 may associate multiple washout period characteristics with each trialed therapy program, or a weighted washout period characteristics including respective characteristics from each of a plurality of physiological signals may be associated with each trialed therapy program. If multiple physiological signals are monitored during the pre-stimulation 92, stimulation 94, and post-stimulation periods 96, processor 70 may determine that the washout period has terminated when all the physiological signals return to their respective baseline states. Alternatively, processor 70 may determine that the washout period has terminated when one of the physiological signals has returned to its baseline state or a specific subset of the types of physiological signals have returned to their respective baseline states. The clinician may, for example, denote one or more of the physiological signals as being primary signals that control when the washout period has terminated.

If processor 70 monitors multiple physiological parameters of patient 14 to determine a washout period characteristic, processor 70 may apply weights to the physiological parameters. The physiological parameters may be weighted based on the relationship to patient mood state. For example, processor 70 may apply more weight to a particular physiological parameter based on the directness of its relationship to a patient mood state, which may be specific to a patient. Depending on the patient, a mood state may be characterized by a different set of symptoms. Processor 70 may, for example, generate a weighted summation of the washout period characteristics and compare the weighted summation to a threshold to determine when the physiological signals have returned to a baseline state.

In some embodiments, processor 70 may apply dynamically shifting weights to different physiological parameters. For example, processor 70 may weigh data from different sensors monitoring different physiological signals based on their reliability or dynamic response characteristics. Physiological signals may be subject to interference from factors such as patient movement, patient breathing, or electrical interference. If the level of the interference is sufficiently low, the physiological data signal may still provide accurate data although there may be some acceptable level of error. In one embodiment, a suitable filter may be used to apply a variable weight to more than one physiological parameter according to estimates of the current noise for signal indicative of the respective physiological parameter.

In other cases, different sensing modalities may reflect different transient responses to therapy stimulation or different washout period characteristics. For example, EEG activity or heart rate may reflect relatively short-term trends in behavior of the physiological parameter of the patient, but may not accurately measure long-term affects due to variation. In some cases, long-term patient state (e.g., long term effects of therapy delivery) may be better reflected in the galvanic skin response and blood pressure, which may take longer to reach a new equilibrium following therapy delivery compared to EEG activity or signals indicative of heart rate. In another embodiment, therefore, processor 70 may implement an algorithm to establish or apply weighting factors to different physiological signals from relatively fast-acting sensors in order to estimate short-term trends, while for physiological signals indicating longer-term washout period trends, the weighting may be used to be adjusted to favor slow-response sensors.

With the aid of suitable filters like a Kalman filter, processor 70 may apply less weight to a physiological signal, and, therefore, the characteristics of the signal during the washout period, if the signal is subject to a relatively high level of noise or adjust the relative weighting of sensors to reflect the dynamic behavior of the sensing modality. In other embodiments, other types of digital filters may be used to process signals from sensing module 26 or other sensors of therapy system 10.

Figure 9:
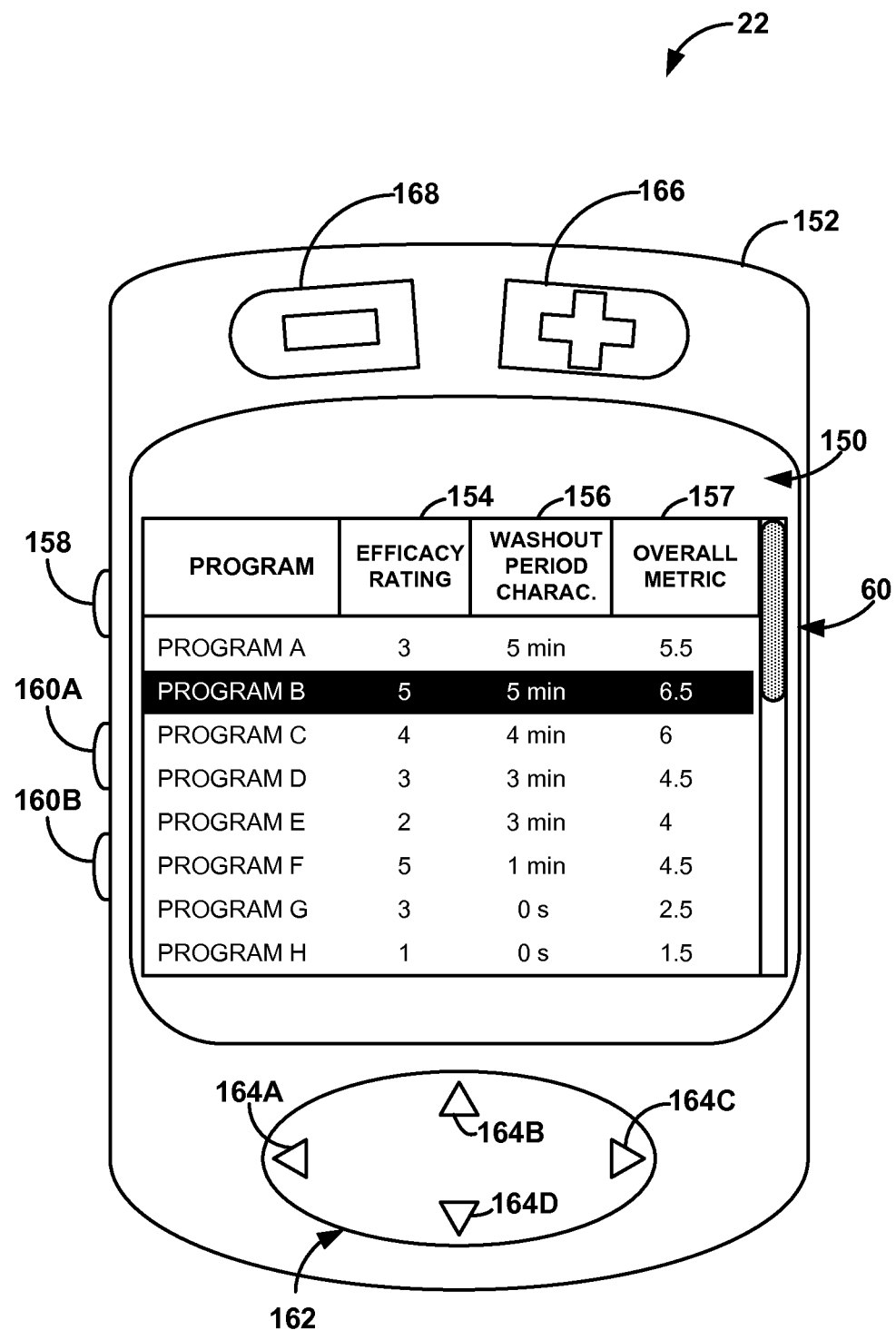
FIG. 9 is a schematic illustration of a clinician programmer, which includes a display presenting a graphical user interface (GUI) with a list of therapy programs.

After trialing a plurality of therapy programs and determining a washout period characteristic for each of the therapy programs, a clinician, with the aid of clinician programmer 22, may order the list of therapy programs based on the washout period characteristics. FIG. 9 is a schematic illustration of clinician programmer 22, which illustrates a graphical user interface (GUI) 150 presented on display 60 of programmer 22. GUI 150 includes a list of therapy programs tested during a programming session, which are designated Program A, Program B, and so forth, along with associated efficacy ratings 154, washout period characteristics 156, and an overall evaluation metric 157. The efficacy rating and washout period characteristic may be considered to be evaluation metrics of the respective therapy program.

The efficacy rating presented by display 60 in the example of FIG. 9 is a numerical rating on a scale from 1 to 5, where a rating of "5" indicates a higher efficacy than a rating of "1." However, other types of scales are possible, and are not limited to a numerical scale or a numerical 1-5 scale. Patient 14 may provide the numerical efficacy ratings, e.g., via clinician programmer 22 or patient programmer 24, in response to therapy delivery according to each therapy program. In this way, the numerical efficacy ratings 154 are subjective assessments of the therapeutic efficacy of a particular therapy program by patient 14. In other embodiments, processor 70 may automatically rate the efficacy of the therapy program based on patient responses to various questions, such as the Beck Depression Inventory, Hamilton Rating Scale for Depression (HAM-D) or the Montgomery-Asberg Depression Rating Scale (MADRS). The Beck Depression Inventory and the HAM-D are both 21-question multiple choice surveys that is filled out by patient 14, and the MADRS is a ten-item questionnaire. The answers to the questions may indicate the severity of patient symptoms or the general patient mood state, and processor 70 may assign an efficacy rating to the therapy program based on the severity of the patient symptoms or patient mood state.

The washout period characteristic shown on display 60 in FIG. 9 is the duration of the washout period. In other embodiments, programmer 22 may display other washout period characteristics, such as the peak amplitude of the physiological signal during the washout period. In addition, in some embodiments, programmer 22 may present more than one washout period characteristic for each tested therapy program.

In addition to a washout period characteristic, in some embodiments, the clinician may evaluate the tested therapy programs based on or a stimulation period characteristic. The stimulation period characteristic may include a characteristic of the physiological signal during the stimulation period 94. For example, the stimulation period characteristic may include the peak, average or median amplitude of the signal during the stimulation period 94, a particular trend in the signal waveform, one or more frequency band characteristics of the signal during the stimulation period 94 or the duration that changes to the signal from the baseline state were observed. One or more characteristics of a physiological signal during stimulation period 94 may be suggestive of the patient's mood state.

In other embodiments, the clinician may evaluate tested therapy programs based on other evaluation metrics, such as a mood indicator rating, an anxiety indicator rating, a patient energy level rating or a subjective rating of the mood improvement (e.g., a mood improvement score) indicated by patient 14 in response to therapy delivery according to each therapy program. Patient 14 may directly provide input to clinician programmer 22 regarding these other evaluation metrics via user interface 74 (FIG. 4) or may provide input to the clinician or another user, who may then input the information to clinician programmer 22 or another computing device. In the case of a mood indicator rating or mood improvement rating, patient 14 may provide a subjective rating of mood or improvement of mood, respectively, following therapy delivery by a therapy program. The rating may be a numerical rating, a sliding scale or any suitable type of rating system. In the case of an anxiety disorder, patient 14 may provide a subjective rating of an anxiety level following therapy delivery by a therapy program. In the case of MDD, patient 14 may provide a subjective rating of depression. In some cases, however, patient 14 may have symptoms of two or more mood disorders, such as MDD and an anxiety disorder, which may be interrelated.

A patient energy level rating may also be received from patient 14 following therapy delivery by a therapy program, e.g., via a numerical rating scale. The patient energy level rating may be useful for evaluating the patient's mood state. For example, in the case of MDD, a relatively high patient energy level (e.g., compared to a baseline energy level prior to delivery of therapy to patient 14) may indicate the therapy system is improving the patient's mood state, i.e., is providing at least a minimal amount of efficacious therapy to patient 14. Processor 70 may associate the mood indicator rating, anxiety indicator rating, and/or patient energy level rating with the therapy program.

Other evaluation metrics may include a rating of the IMD 16 power usage when delivering therapy according to particular therapy program, which may be associated with the power usage rating in memory 72 of programmer 22 or a memory of another device. For example, IMD 16 may consume more energy when generating and delivering electrical stimulation therapy according to some therapy programs versus other therapy programs. The energy associated with each therapy program may be calculated as product of the power required to generate the stimulation signals defined by the therapy program and the duration of the stimulation signal. The power required to generate the stimulation signal may generally be a product of the voltage and current needed to generate the stimulation signal. Therefore, an energy associated with a stimulation signal may be a direct function of voltage, current, and duration of the stimulation signal.

In embodiments in which IMD 16 is implanted within patient 14 for chronic therapy delivery, it may be desirable to minimize power consumption in order to extend the useful life of IMD 16 or minimize time between recharging of power source 36 (FIG. 2). Accordingly, the clinician may evaluate the tested therapy programs based on the respective power usages. The power usage may be, for example, rated on a numerical scale, where the lower power consumption therapy programs are provided with a higher energy efficiency rating. For example, a rating of "5" may be assigned to therapy programs that require a particular range of power to generate the stimulation signals defined by the therapy programs, a rating of "4" may be assigned to therapy programs that require another range of power for signal generation, where the power range for the rating of "4" is higher than the power range for the rating of "5." Other scales for evaluating power usage are contemplated.

In some embodiments, a clinician may also evaluate tested therapy programs based on side effects resulting from therapy delivery according to the respective therapy programs. Side effect information that may be collected for each therapy program may include, for example, the type, duration or severity of the side effects observed during the stimulation period and/or washout period, i.e., after stimulation delivery as ceased, as well as the time during the washout period that the side effects became evident to patient 14. In some embodiments, patient 14 may provide input indicating a numerical rating of the side effects, where a higher numerical rating number indicates a relatively more severe side effect. Alternatively, patient 14 may select the type of side effects experienced in response to therapy delivery by a therapy program from a list provided by programmer 22, and processor 70 may automatically assign a side effect rating based on the selected side effects. For example, patient 14 may select a "severe headache" or "moderate headache" rating from a menu provided by programmer 22, which processor 70 may automatically associate with a particular numerical side effect rating.

Examples of side effects that patient 14 may select from or rate include, but are not limited to, hypomania effects, euphoria, perseveration, anxiety (e.g., panic), vague feelings of unease, subjective feelings of facial flushing, subjective feelings of increased heart rate, actual facial flushing data (e.g., indicated by physiological signals during the washout period), actual heart rate data, paresthesia (e.g., sensations in the face, neck or arms), and subjective feelings muscular contraction (e.g., sensations in the face, neck or arms) or actual EMG data reflecting muscular contraction. The relevant side effects may be determined based on the patient condition for which therapy system 10 is used to manage.

In some cases, an overall evaluation metric 157 may be generated for each trialed therapy program, where the specific evaluation metrics, such as the efficacy rating, washout period characteristic, stimulation period characteristic, mood indicator rating, an anxiety indicator rating, a patient energy level rating, and/or power consumption or efficiency rating, are weighted according to their relative importance to the therapy program evaluation. For example, the clinician may determine that the washout period characteristic should have twice the weight as the efficacy rating, due to the subject nature of the efficacy rating and the relatively objective nature of the washout period characteristic. As another example, the clinician may select the one or more therapy programs having the greatest improvement in patient mood state, minimal or no side effects, and optimal battery life for chronic therapy delivery to patient 14.

In the embodiment shown in FIG. 9, each washout period characteristic is given a score on a scale from 1 to 5, where a score of "1" indicates a washout period duration of between about 0 seconds (s) and about 30 s, a score of "2" indicates a washout period duration of between about 30 s to about 2 minutes (min), a score of about "3" indicates a washout period duration between about 2 min to about 4 min, a score of about "4" indicates a washout period duration between about 4 min to about 6 min, and a score of about "5" indicates a washout period duration between of about 6 min or higher. Some physiological effects, such as facial flushing, may take a relatively long time (on the duration of minutes) to return to a baseline state. These washout period scores may then be weighted with the efficacy rating to arrive at the overall metric. For example, with respect to Program A, the washout period duration is about 5 minutes, thus, the score is 4. If the washout period characteristic has twice the weight as the efficacy rating, the overall metric would equal approximately 5.5 (i.e., (washout period score*2+efficacy rating)/2).

Processor 70 of clinician programmer 22 may receive input from the clinician or another user selecting one of the evaluation metric types with which to order the list of therapy programs. For example, display 60 may be a touch screen display, and the clinician may select efficacy rating box 154, washout period characteristic box 156 or weighted metric box 157, and processor 70 may order the list of therapy programs according to evaluation metric associated with the selected text box. In some cases, the clinician may wish to maximize the duration of the washout period, e.g., to maximize the energy efficiency of IMD 16. The clinician may determine which therapy program resulted in the longest washout period duration by ordering the list of therapy programs according to the washout period duration or the overall metric 157, as shown in FIG. 9.

Ordering the list of therapy programs according to a user-chosen criteria enables the clinician to quickly identify the therapy programs that exhibited the longest washout period duration, as well as to identify the respective efficacy rating for the therapy programs. In contrast, without the automatic ordering of the therapy programs list according a user-chosen criteria, the clinician must typically manually sort through the data in order to identify the therapy program with the desired evaluation metric values. In other embodiments, the clinician may wish to decrease the washout period.

In the embodiment shown in FIG. 9, the therapy programs are ordered according to the associated washout period characteristics. In the example shown in FIG. 9, Programs A and B both exhibited the longest relative washout period duration. However, Program B is associated with a higher efficacy rating (5) than Program A (rating of 3). In addition, Program B has a higher overall metric value than Program A, due to the higher efficacy rating. Accordingly, the clinician may choose to implement Program B for chronic therapy delivery or to use Program B to generate further therapy programs for testing.

In some cases, the clinician may further evaluate Program B, e.g., by rating the efficacy of Program B based on patient responses to various questions, such as the Beck Depression Inventory, Hamilton Rating Scale for Depression (HAM-D) or the Montgomery-Asberg Depression Rating Scale (MADRS). In some cases, processor 70 may prompt patient 14 to answer the questions after therapy is delivered to patient according to Program B. The questions may be presented to patient 14 via display 60 of clinician programmer 22, or by another electronic form or paper form and the answers may be inputted into clinician programmer 22. The patient's answers to the questions may be useful for confirming the usefulness of Program B, as well as other selected therapy programs.

In some cases, processor 70 of clinician programmer 22 may automatically determine more than one washout period characteristic for each therapy program. Thus, in some embodiments, GUI 150 may present more a list of therapy programs along with two or more types of associated washout period characteristics. The clinician may order the list according to any one of the washout period characteristics. In addition, the clinician may order the list according to an overall metric that applies different weights to two or more of evaluation metrics, which may include two or more washout period characteristics (e.g., washout period duration and peak amplitude).

Compared to the respective efficacy ratings 154 or other subjective evaluation metrics received from patient 14 (e.g., ratings as to severity of side effects), a washout period characteristic and stimulation period characteristic may provide a relatively objective metric with which to evaluate therapy programs. The washout period and stimulation period characteristics are determined based on a monitored physiological signal of patient 14 rather than the subjective input from patient 14. Accordingly, the washout period and stimulation period characteristics may also be useful for evaluating therapy programs, e.g., based on a consistency between the patient's subjective input and information determined based on the stimulation and/or washout period characteristics.

As one example, if patient 14 provides an efficacy rating of "3" for Programs A and D, as shown in FIG. 9, but the washout period characteristics are different, the clinician may conclude that the Programs A and D are effective, but not as effective as Therapy Program B, which may be associated with a consistency indication that indicates the patient input regarding a mood state was consistent with a mood state determined based on a washout or stimulation period characteristic. In addition, the clinician may conclude that the washout period characteristic or stimulation period characteristic is useful for differentiating between the effects of Programs A and D. Similar efficacy ratings for two or more therapy programs may indicate that the patient efficacy rating scale is not fine enough. Thus, the washout period characteristic (or the stimulation period characteristic) may be useful for determining between subtle differences in the effects of different therapy programs on patient 14.

In some cases, the patient input may be entitled to less weight than the physiological signal. That is, because the washout period and stimulation period characteristics are determined based on a monitored physiological signal of patient 14 rather than the subjective input from patient 14, the washout period and stimulation period characteristics may also be useful for assessing the consistency of the patient's subjective input for other evaluation metrics and assessing the validity of the patient's input. If, for example, patient 14 provides an efficacy rating of "3" for Programs A and D, as shown in FIG. 9, but the washout period characteristics are different, the clinician may conclude that the patient's efficacy rating is invalid or entitled to less weight than the washout period characteristic. Thus, the clinician may conclude that the washout period characteristic is more useful for differentiating between the effects of Programs A and D.

As another example, the objective nature of the washout period and stimulation period characteristics may be useful for diagnosing a placebo effect from the stimulation therapy. For example, if patient 14 provides an efficacy rating of "5" for all tested therapy programs, but the washout period characteristics or stimulation period characteristics differ greatly between the tested therapy programs, the clinician may determine that minimal to no stimulation therapy is necessary to manage the patient's psychiatric disorder.

Clinician programmer 22 also includes housing 152, power button 158, contrast buttons 160A, 160B, control pad 162 with directional buttons 164A, 164B, 164C, and 164D, increase button 166, and decrease button 168. Housing 152 may substantially enclose the components of programmer 22, such as processor 70 and memory 72. A user may depress power button 158 to turn programmer 22 on or off. Programmer 22 may include safety features to prevent programmer 22 from shutting down during a telemetry session with IMD 16 or another device in order to prevent the loss of transmitted data or the stalling of normal operation. Alternatively, programmer 22 and IMD 16 may include instructions for handling possible unplanned telemetry interruption, such as battery failure or inadvertent device shutdown.

As previously indicated with respect to FIG. 4, display 60 may be a liquid crystal display (LCD), touch screen display, or another type of monochrome or color display capable of presenting information to a user, e.g., a clinician. Contrast buttons 160A, 160B may be used to control the contrast of display 60. In addition to displaying a list of trialed therapy programs and associated evaluation metrics, processor 70 of clinician programmer 22 may also present information regarding the type of IMD 16, operational status of IMD 16, patient data, and operational status of clinician programmer 22 on display 60. Control pad 162 allows the user to navigate through items presented on display 60. For example, the clinician may press control pad 120 on any of arrows 164A-164D in order to move between items presented on display 60 or move to another screen not currently shown by display 60. For example, the clinician may depress or otherwise activate arrows 164A, 164C to navigate between screens of GUI 150, and depress or otherwise activate arrows 164B, 164D to scroll through the therapy programs presented by GUI 150. The clinician may press the center portion of control pad 162 in order to select any highlighted element in GUI 150. For example, the clinician may scroll to and select "PROGRAM B," which is shown to be highlighted in FIG. 9, in order to receive more information about Program B, such as the stimulation parameter values defined by Program B. In other embodiments, scroll bars, a touch pad, scroll wheel, individual buttons, a stylus (in combination with a touch screen display 60) or a joystick may perform the complete or partial function of control pad 162.

Increase button 166 and decrease button 168 provide input mechanisms for a user, such as clinician or patient 14. In general, depressing decrease button 168 one or more times may decrease the value of a highlighted therapy parameter and depressing increase button 166 one or more times may increase the value of a highlighted therapy parameter. While buttons 166, 168 may be used to control the value of any therapy parameter, the user may also utilize buttons 166, 168 to select or generate particular programs for testing during a therapy programming session. In addition, patient 14, the clinician or another user may utilize control pad 120, buttons 166, 168 or display 60 in embodiments in which display 60 comprises a touch screen to input information related to the efficacy of a therapy program or other evaluation metrics. Further, the clinician or another user may utilize control pad 162, buttons 166, 168 or display 60 in embodiments in which display 60 comprises a touch screen in order to input information related to a washout period characteristic. Alternatively, processor 70 of programmer 22 may automatically determine the washout period characteristics based on physiological parameter signals received from sensing module 26 (FIG. 1).

Clinician programmer 22 may take other shapes or sizes not described herein. For example, programmer 22 may take the form of a clam-shell shape, similar to cellular phone designs. In any shape, programmer 22 may be capable of performing the requirements described herein. Furthermore, in other embodiments, the buttons of programmer 22 may perform different functions than the functions provided in FIG. 9 as an example. In addition, other embodiments of programmer 22 may include different button layouts or number of buttons. For example, display 60 may be a touch screen that incorporates all user interface and user input mechanism functionality.

Figure 10:
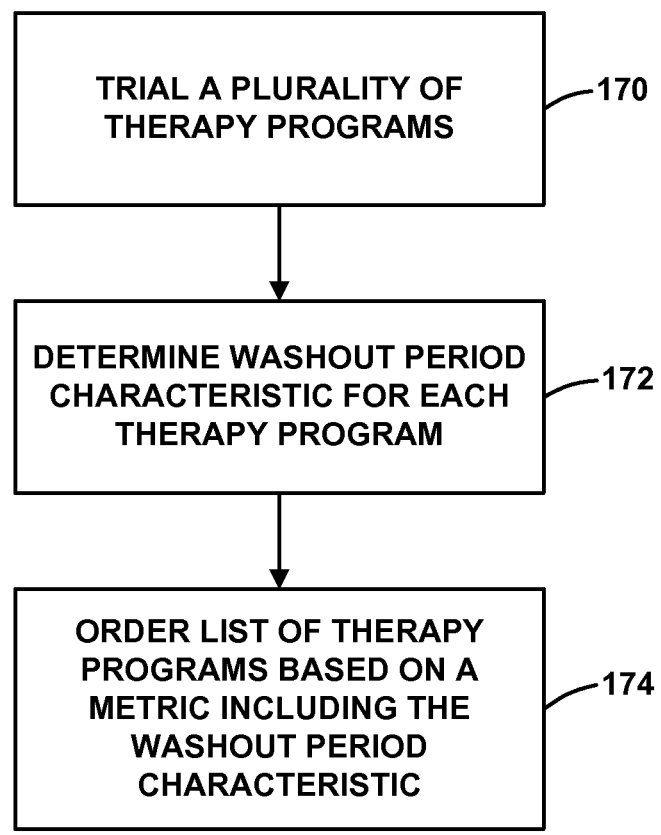
FIG. 10 is a flow diagram illustrating an example technique for ordering therapy programs based on a washout period characteristic.

FIG. 10 is a flow diagram illustrating an embodiment of a technique for ordering a list of therapy programs according to a washout period characteristic. With the aid of clinician programmer 22 or another computing device, a clinician may deliver electrical stimulation to patient 14 according to a plurality of therapy programs during a trial stimulation session (170). As previously indicated, during a trial stimulation session, stimulation may be delivered to patient 14 according to each therapy program for a sufficient period of time to determine the effects, if any, the therapy has on patient 14. For each trialed therapy program, the clinician may determine a washout period characteristic (172). For example, processor 70 of programmer 22 may automatically determine the washout period characteristics during the trial therapy sessions. In addition, other evaluation metrics may be generated for each therapy program, such as an efficacy rating (e.g., a numerical efficacy rating or a pain map) or different thresholds for each therapy program (e.g., a perception threshold).

In some cases, the clinician may determine a weighted evaluation metric (i.e., an overall metric) for each trialed therapy program. As previously indicated, two or more evaluation metrics (e.g., efficacy rating or washout period characteristic) may be combined into a composite metric by applying weights to the evaluation metrics based on their relative importance to the evaluation of the therapy programs, where the evaluation metrics may be weighted the same or differently. The clinician may order the list of therapy programs based on an evaluation metric that considers the washout period characteristic (174). For example, the clinician may order the list of therapy programs with the aid of GUI 150 of clinician programmer 22 (FIG. 9) according to the washout period characteristic or an overall evaluation metric. In this way, the clinician may evaluate the trialed therapy programs based on the washout period characteristic in a relatively quick manner. If more than one washout period characteristic is determined for each therapy program, the clinician may order the list of trialed therapy programs according to one of the characteristics or according to an evaluation metric that considers two or more of the washout period characteristics.

When titrating DBS parameter values to determine an efficacious range of therapy parameter values for managing a mood disorder of patient 14, changes in mood state during stimulation period 94 (FIGS. 5A-5E) as well as during the post-stimulation period 96 (FIGS. 5A-5E) may be desirable. For example, changes to the patient's mood state may indicate the patient's response to therapy delivery according to a particular therapy program. Associating a patient mood state with a washout period characteristic, and, in some cases, a stimulation period characteristic ("mood state classification") may be useful for screening therapy programs, e.g., to help identify a target change in a physiological signal during a washout period that indicates a beneficial change to the patient's psychiatric disorder. Similarly, a washout period characteristic may also be useful for avoiding stimulation parameter values that result in adverse events. For example, after delivering therapy to patient 14 according to a therapy program during a trial session, the clinician may identify a target change in a physiological signal during the washout period that is associated with a negative mood state (e.g., a depressed state, hypomanic state or manic state). In response, the clinician may test another therapy program or modify at least one therapy parameter value of the tested therapy program.

In addition, as described in further detail below, associating a washout period characteristic with a patient mood state may be useful for a closed-loop therapy system. For example, if a certain characteristic of a physiological signal during the washout period is associated with an improvement in a MDD of patient 14, a closed-loop therapy system may deliver therapy, monitor the physiological signal, and continue delivering therapy until the characteristic of the physiological signal is observed following therapy delivery.

Figure 11:
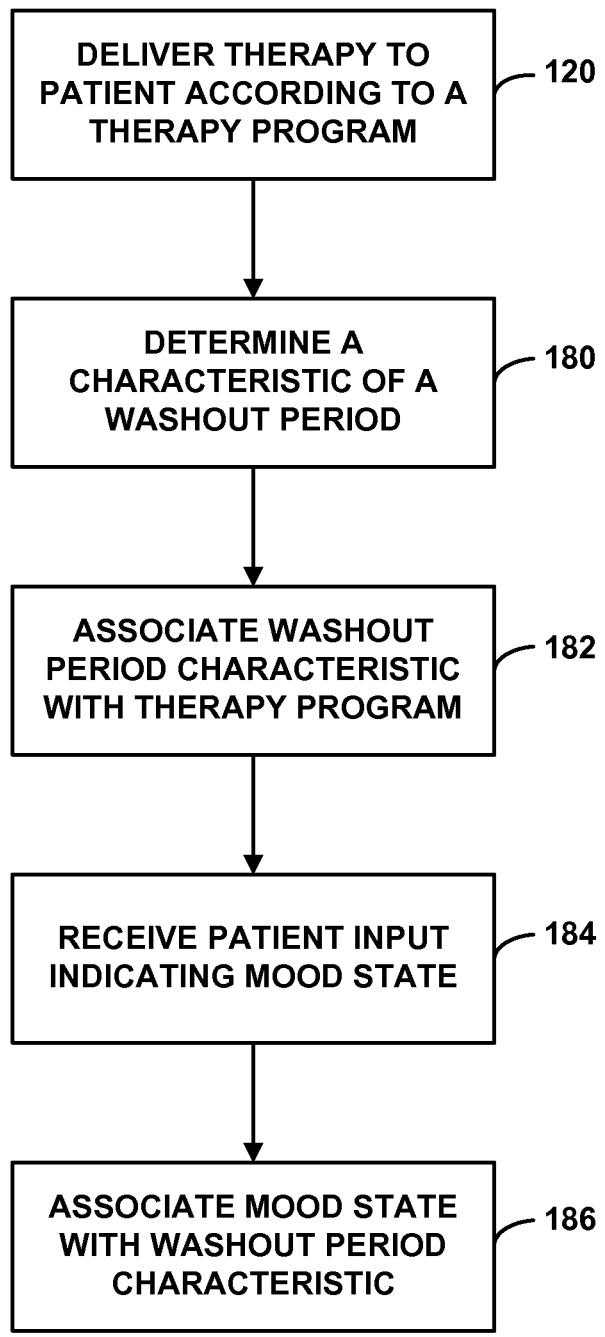
FIG. 11 is a flow diagram illustrating an example technique for associating different patient mood states with one or more washout period characteristics.

FIG. 11 is a flow diagram illustrating an example technique for associating different patient mood states with one or more washout period characteristics. In this way, at a later time, a washout period characteristic resulting from therapy delivery may be used to determine a patient mood state. As with the previous techniques, although the technique shown in FIG. 11 is described as being performed by processor 70 of clinician programmer 22, in other embodiments, processor 40 of patient programmer 24 or a processor of another computing device may associate different patient mood states with one or more washout period characteristics in accordance with the technique shown in FIG. 11.

Processor 70 of clinician programmer 22 may control IMD 16 to deliver therapy to patient 14 according to a therapy program (120) using any suitable technique, such as the ones described above with respect to FIG. 7A. Processor 70 may receive a signal from sensor 26 indicating activity of a physiological parameter of patient 14, such as the patient's respiratory rate, heart rate or galvanic skin response. Based on the physiological signal from sensor 26, processor 70 may automatically determine a characteristic of a washout period associated with the therapy program (180). For example, processor 70 may use the technique described with respect to FIG. 8 to determine the washout period characteristic. Processor 70 may associated the washout period characteristic with the therapy program (182), and record the washout period characteristic in memory 72 (FIG. 4) of clinician programmer 22.

Processor 70 may receive input from patient 14 indicating a mood state during the post-stimulation period, and, in some cases, the stimulation period (184). The patient 14 may indicate a mood state felt by patient 12 in response to therapy delivery according to the therapy program. The mood state may be the mood state that is first observed during the stimulation period and substantially persists throughout a washout period, which follows the stimulation period. In other examples, the mood state associated with the therapy program may be first observed during the post-stimulation period. In one embodiment, patient 14 provides input indicating a mood state by interacting with user input mechanism 56 of user interface 44 of patient programmer 24. As another example, patient 14 may provide input indicating a mood state by interacting with user input mechanism 56 of user interface 74 of clinician programmer 22 either directly or indirectly, e.g., via another user than inputs the information into clinician programmer 22.

Patient 14 may indicate a mood state using any suitable technique. For example, patient 14 may select a mood state from a predefined list of mood states (e.g., moderate anxiety, severe anxiety, lack of anxiety, in the case of an anxiety disorder), manually input a mood state, select a numerical rating of the severity of a specific mood state (e.g., a numerical range of 1 through 5, where a rating of "5" indicates patient 14 experienced a severe depressive state, while a rating of "1" indicates patient 14 was in a relatively non-depressed state compared to a depressive state). Other techniques for receiving input regarding a mood state of patient 14 are contemplated.

Processor 70 may associate the indicated mood state with the washout period characteristic (186) and store the data in memory 72 of programmer 22 or a memory of another device, such as IMD 16 or patient programmer 24. In some cases, upon request by a user, processor 70 may present a list, table or other data format illustrating the washout period characteristics and associated mood states via display 60. For example, if the washout period characteristic includes a peak or average value of the waveform amplitude of the physiological signal during the washout period, processor 70 may present a list of a plurality of mood states and associated physiological signal amplitude values. As another example, if the washout period characteristic includes a trend in the physiological signal waveform during the washout period, processor 70 may present a list of mood states and provide links to a visual representation of the waveform trend.

After associating washout period characteristics with mood states for one or more patients, a clinician may generate a mood state probability for each washout period characteristic. In some cases, the washout period characteristic may not provide a direct link to patient mood and may be a surrogate marker that is suggestive of the patient mood state, rather than symptomatic. Thus, the association between mood states and washout period characteristics may be somewhat inaccurate and imprecise. Furthermore, the patient input regarding the mood state may be inaccurate or inconsistent between therapy programs having similar washout period characteristics. Accordingly, it may be desirable for the clinician to confirm that a mood state is associated with a particular washout period characteristic by recording the patient's mood state for multiple trials of one or more therapy programs that result in the washout period profile. That is, processor 70 may determine that a washout period characteristic is associated with a patient mood state only after the patient indicates the same mood state for the same washout period characteristic a minimum number of times, regardless of whether the washout period characteristic is generated by the same therapy program. Different therapy programs may result in the same washout period characteristic.

In some embodiments, rather than directly associating a patient mood state with a washout period characteristic, processor 70 may assign a probability of the mood state with the washout period characteristic. For example, for a particular washout period characteristic, processor 70 may determine that 85% of the time the washout period characteristic was observed, patient 14 indicated a non-depressive mood state. The washout period characteristics may be associated with a patient mood state based on testing therapy programs on a single patient or more than one patient.

Mood state classification based on washout period characteristics may be beneficial for screening therapy programs. After establishing a library (or catalog or any data structure) of washout period characteristics and associated mood states or mood state probabilities, a clinician may evaluate the efficacy of one or more therapy programs by associating the therapy program with a mood state or mood state probability based on the washout period characteristic associated with the therapy program. The library of period characteristics and associated mood states or mood state probabilities may be specific to patient 14 (i.e., generated based on information from patient 14) or may be more general, e.g., based on information from more than one patient.

In some embodiments, processor 70 may also determine a stimulation period characteristic, receive input from patient 14 indicating a mood state, and associate the stimulation period characteristic with the patient mood state using a technique similar to that shown in FIG. 11.

Although FIG. 11 illustrates associating a mood state with a washout period characteristic based on data from a single patient, in some embodiments, mood states may be associated with washout period characteristics based on data from more than one patient. Thus, in some cases, mood state information and washout period characteristics from a cross-section of patients (e.g., a class of patients having similar conditions) may be used to support an assumed correlation between a mood state and a washout period characteristic.

Figures 12, 13:
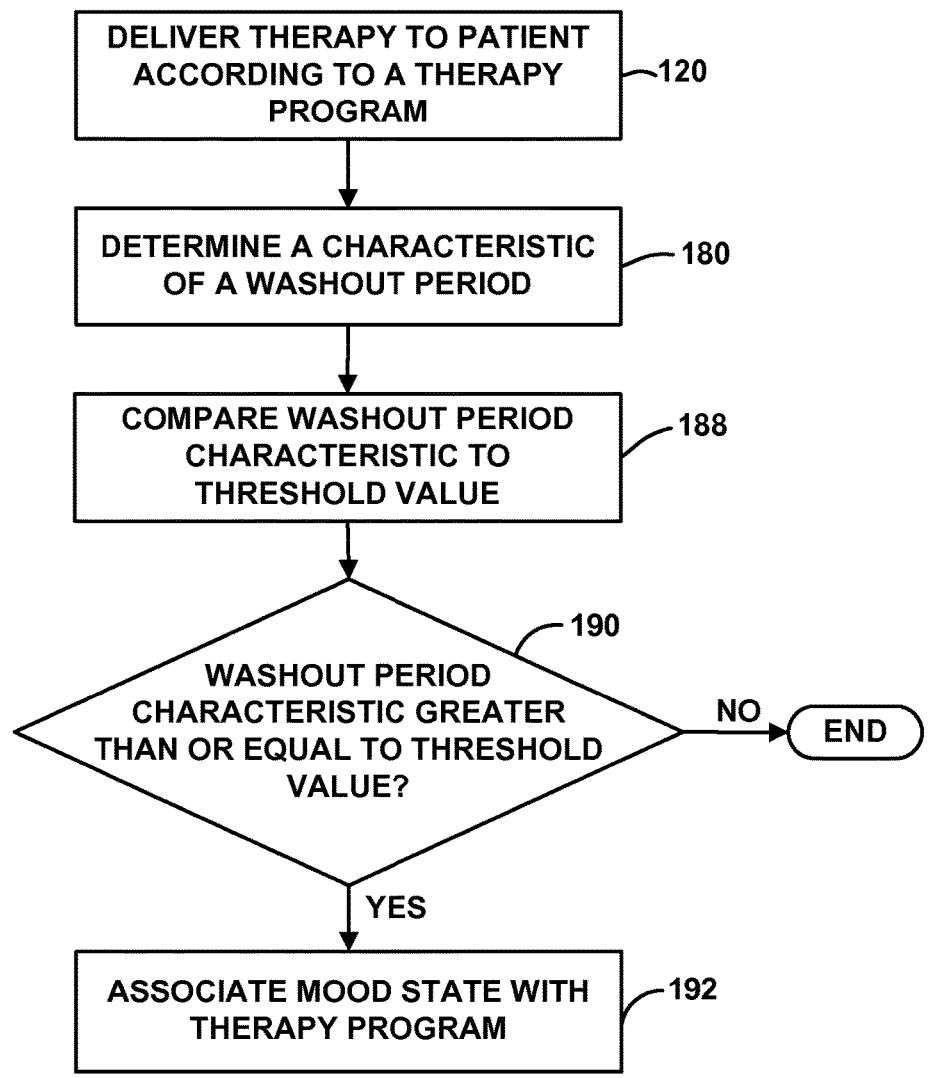
FIG. 12 is a flow diagram illustrating an example technique for associating a therapy program with a patient state based on a comparison between a washout period characteristic and a threshold value.
FIG. 13 is an example data structure that associates different patient mood states with threshold values.

FIG. 12 is a flow diagram illustrating an example technique for associating a therapy program with a patient mood state based on the washout period characteristic associated with the therapy program. Just as with the technique shown in FIG. 11, processor 70 may deliver therapy to patient 14 according to a therapy program (120) and determine a washout period characteristic of the therapy program (180). If the washout period characteristic comprises a washout period duration or physiological signal amplitude, processor 70 may compare the washout period characteristic to a threshold value (188). The threshold value may be stored in memory 72 of clinician programmer 22 or a memory of another device. The threshold value may indicate the presence of a particular patient state during the washout period, and may be established using any suitable technique that associates a washout period characteristic with a patient mood state, such as the technique described with respect to FIG. 11.

In some embodiments, processor 70 may compare the washout period characteristic to one or more threshold values, which may each be associated with a different patient mood state. FIG. 13 illustrates a data structure that associates a plurality of patient mood states with threshold amplitude values. The threshold values are listed in terms of a voltage amplitude change relative to a baseline amplitude value, which may be established during the pre-stimulation period 92 (FIGS. 5A-5E), prior to the delivery of stimulation according to the therapy program. As previously discussed, the baseline amplitude value may include a peak voltage or current amplitude of the signal during the pre-stimulation period 92, a mean, median or average value of the physiological signal amplitude during the pre-stimulation period 92, or other values based on the amplitude of the physiological signal amplitude during the pre-stimulation period 92.

While a baseline amplitude value of the physiological signal may differ between patients, it may be found that for a plurality of patients, a change in the physiological signal amplitude is associated with a particular patient mood state. Accordingly, the threshold value may be stated in terms of the sum of the baseline amplitude value and the absolute change in the physiological signal amplitude. In other embodiments, the threshold value may be merely stated in terms of the amplitude change in the physiological signal, and processor 70 may determine the washout period characteristic to be the change in the physiological signal amplitude relative to the baseline amplitude value.

Processor 70 may compare the washout period characteristic to the threshold values shown in FIG. 13 in order to determine whether patient 14 is in a non-depressed mood state, moderately depressed mood state or a severely depressed mood state. For example, if the amplitude value of the washout period characteristic exceeds (or, in some embodiments, is greater than or equal to) the threshold value associated with the non-depressed mood state, processor 70 may conclude that patient 14 is in a non-depressed mood state. On the other hand, if the amplitude value of the washout period characteristic does not exceed (or, in some embodiments, is less than or equal to) the threshold value associated with the non-depressive mood state, processor 70 may conclude that patient 14 was not in a non-depressed mood state following therapy delivery according to the therapy program.

Processor 70 may then compare the amplitude value of the washout period characteristic to the threshold value associated with the moderate depression mood state. If the amplitude value of the washout period characteristic exceeds (or, in some embodiments, is greater than or equal to) the threshold value associated with the moderate depression mood state, processor 70 may conclude that patient 14 was in a moderately depressed mood state following therapy delivery according to the therapy program. On the other hand, if the amplitude value of the washout period characteristic does not exceed (or, in some embodiments, is less than or equal to) the threshold value associated with the moderate depression mood state, processor 70 may conclude that patient 14 was not moderately depressed following therapy delivery according to the therapy program. Processor 70 may then conclude that patient 14 was in a severely depressed mood state following therapy delivery according to the therapy program. In some cases, processor 70 may compare the amplitude value of the washout period characteristic to the threshold value associated with the severe depression mood state in order to verify that patient 14 was in a severely depressed mood state following therapy delivery according to the therapy program.

Processor 70 may employ a similar technique to compare a washout period characteristic with multiple thresholds other than amplitude thresholds. While a voltage amplitude is shown in FIG. 13, in other embodiments, the baseline amplitude may be a current amplitude. In addition, in other embodiments, other mood state characteristics may be associated with the mood states. For example, the threshold value may be a washout period duration provided in terms of seconds or milliseconds. Furthermore, the threshold values associated with the patient mood state in FIG. 13 are for purposes of illustration only. Other threshold values for determining a patient mood state are contemplated.

Returning now to the flow diagram shown in FIG. 12, if processor 70 determines that the washout period characteristic is not greater than or equal to one or more threshold values (190), processor 70 may not associate the therapy program with a particular mood state. On the other hand, if processor 70 determines that the washout period characteristic is greater than or equal to one or more threshold values (190), processor 70 may associate the determined mood state with the therapy program (192). Processor 70 may determine the mood states for a plurality of therapy programs and compare the efficacy of the therapy programs based on the associated mood states.

Figure 14:
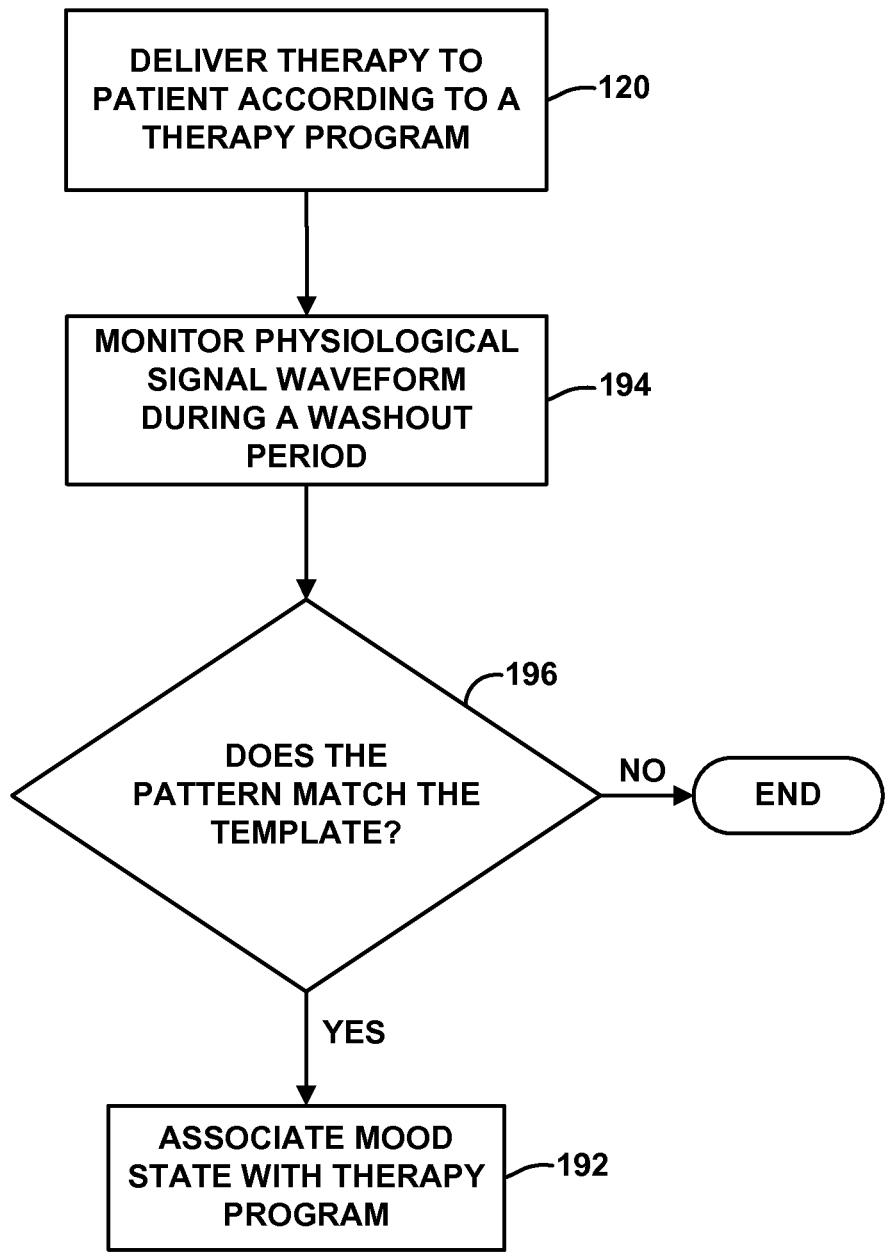
FIG. 14 is a flow diagram illustrating an example technique for associating a therapy program with a patient state based on a comparison between a washout period characteristic and a template.

In some cases, a washout period characteristic may be a trend in the physiological signal during the post-stimulation period. FIG. 14 is a flow diagram illustrating an example technique for associating a therapy program with a patient mood state based on a comparison between a washout period characteristic and a template, which may be stored in memory 72 of clinician programmer 22. Processor 70 may control the delivery of therapy to patient 14 according to a therapy program (120). During the washout period, if any, following the therapy delivery, processor 70 may monitor a pattern of the physiological signal waveform (194) and compare the pattern to a template (196).

In one embodiment, processor 70 performs a temporal correlation between the physiological signal waveform during the washout period and the template. Processor 70 may sample the physiological signal with a sliding window and compare the sampled waveform with a stored template waveform. For example, processor 70 may perform a correlation analysis by moving a window along a digitized plot of the amplitude waveform of physiological signal at regular intervals, such as between about 1 ms to about 10 ms intervals, to define a sample of the physiological signal during the washout period. The sample window is slid along the plot until a correlation is detected between the waveform of the template and the waveform of the sample of the physiological signal defined by the window, or until the end of the washout period (e.g., when the physiological signal returns to a baseline state). By moving the window at regular time intervals, multiple sample periods are defined. The correlation may be detected by, for example, matching multiple points between the template waveform and the waveform of the plot of the physiological signal over time, or by applying any suitable mathematical correlation algorithm between the sample in the sampling window and a corresponding set of samples stored in the template waveform.

If the pattern of the physiological signal waveform does not match the template (196), processor 70 may determine that there is no patient state associated with the washout period characteristic. In some cases, processor 70 may prompt patient 14 to input information relating to the patient mood state following the therapy delivery, e.g., by initiating a communication session with patient 14 via display 60, and associate the patient indicated mood state with the washout period characteristic.

If the pattern of the physiological signal waveform substantially matches (e.g., within a particular percentage, such as 90% to about 100% match) the template (196), processor 70 may associate the patient mood state with the therapy program (192). In some embodiments, processor 70 may compare the physiological signal waveform to a plurality of templates, which are each associated with a different patient state.

Figure 15:
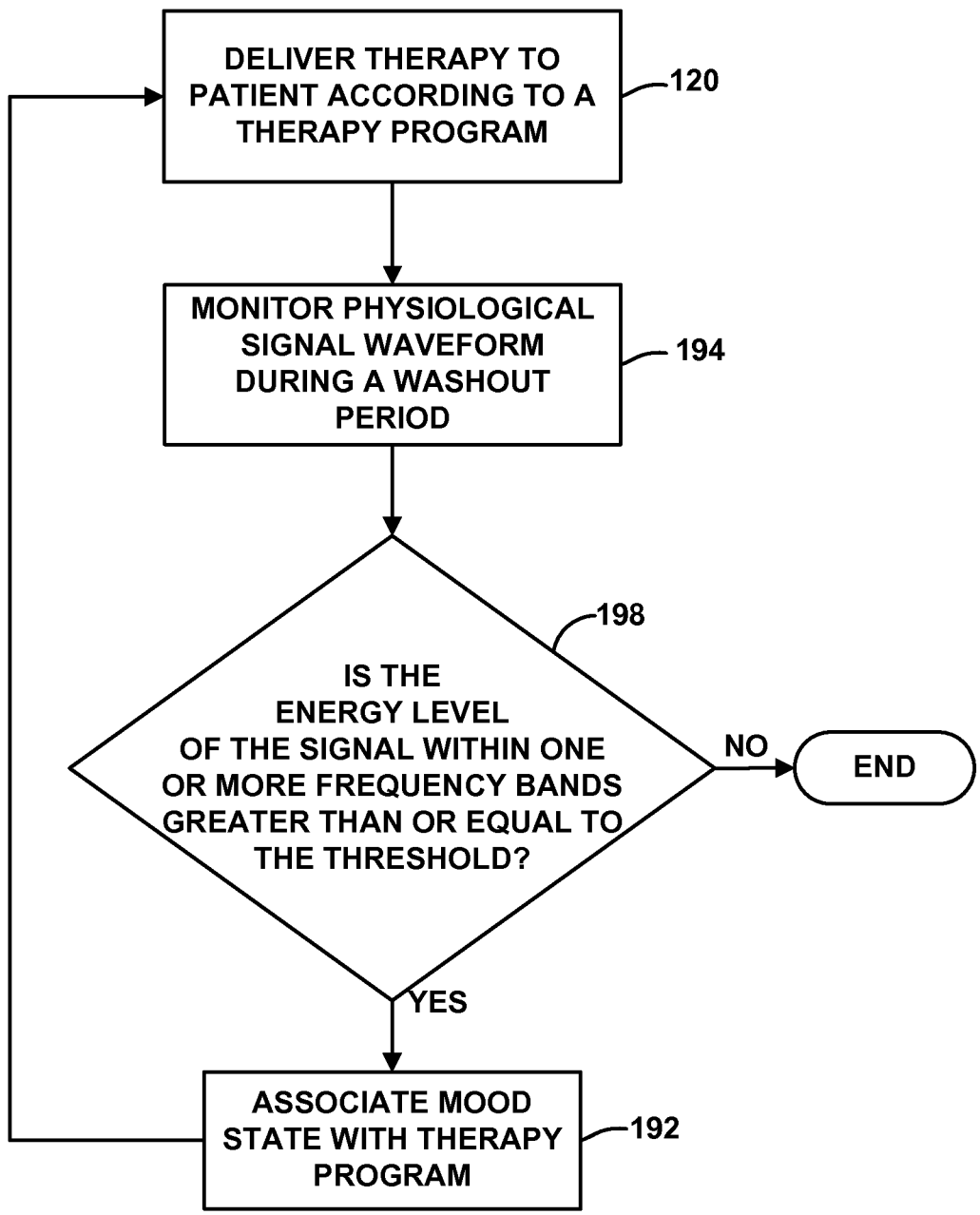
FIG. 15 is a flow diagram illustrating an example technique for associating a therapy program with a patient state based on a comparison between a washout period characteristic and a threshold energy level of a frequency band.

In some cases, a washout period characteristic may be a frequency band characteristic of the physiological signal during the post-stimulation period, such as an energy level in a particular frequency band or a ratio in energy levels between different frequency bands. FIG. 15 is a flow diagram illustrating an example technique for associating a therapy program with a patient state based on a comparison between a washout period characteristic and a threshold energy level of a frequency band, which may be stored in memory 72 of clinician programmer 22 or a memory of another device. Processor 70 may control the delivery of therapy to patient 14 according to a therapy program (120). During the washout period, if any, following the therapy delivery according to the therapy program, processor 70 may monitor a physiological signal (194) and compare the energy level of the physiological signal within one or more frequency bands to a threshold value (198).

Either sensing module 26 or processor 70 may tune the physiological signal to a particular frequency band that is indicative of the patient's mood state. For example, in one embodiment, processor 70 tunes the physiological signal to the alpha band (e.g., about 5 Hz to about 10 Hz). The energy level of the physiological signal within the selected frequency band may be considered to be the washout period characteristic in some embodiments. Processor 70 may compare energy level within the particular frequency band during the washout period to a stored value to determine the patient mood state resulting from therapy delivery according to the therapy program. In another embodiment, processor 70 may compare the ratio of power levels within two or more frequency bands to a stored value in order to determine the patient mood state.

If the energy level of the physiological signal during the washout period is not greater than or equal to the threshold value (198), processor 70 may determine that there is no patient state associated with the washout period characteristic. In some cases, processor 70 may prompt patient 14 to input information relating to the patient mood state following the therapy delivery, e.g., by initiating a communication session with patient 14 via display 60, and associate the patient indicated mood state with the washout period characteristic. If the energy level of the physiological signal during the washout period is greater than or equal to the threshold value (198), processor 70 may associate the patient mood state with the therapy program (192). In some embodiments, processor 70 may compare the energy level or ratio of energy levels of the physiological signal to a plurality of threshold values, which are each associated with a different patient mood state.

Although the technique shown in FIG. 15 associates a patient mood state with a therapy program if the energy level of the physiological signal within one or more frequency bands is greater than or equal to a threshold value, in other embodiments, processor 70 may determine the presence of the mood state if the energy level of the physiological signal within one or more frequency bands is greater than a threshold value, less than the threshold value, or less than or equal to the threshold value.

In another embodiment, the correlation of changes of power between frequency bands may be compared to a stored value to determine whether the physiological signal indicates patient 14 is in a particular mood state. This correlation of changes in power of different frequency bands may be implemented into an algorithm that helps processor 70 eliminate false positives of a patient mood state by relying on energy levels within more than one frequency band.

In some embodiments, processor 70 may also associate a therapy program with a patient mood state based on a stimulation period characteristic with a technique similar to that shown in FIGS. 12, 14, 15. The association between a therapy program and a stimulation period characteristic may be used for similar purposes as the association between a therapy program and a washout period characteristic. The patient mood state may be associated with a stimulation period characteristic in any suitable way, such as with a technique similar to that shown in FIG. 11.

The techniques shown in FIGS. 12, 14, and 15 may be used to determine the efficacy of a therapy program or to determine the relatively efficacy of a plurality of therapy programs based on a patient mood state following delivery of therapy according to the therapy programs. In some cases, mood state classification may also be useful for modifying at least one therapy parameter value of a therapy program. For example, after identifying a target change in a physiological signal during the washout period that is associated with a negative mood state, e.g., using the techniques shown in FIG. 12, 14 or 15, a clinician may test another therapy program or modify at least one therapy parameter value of the tested therapy program. The clinician may adjust the at least one therapy parameter value in order to generate a therapy program that improves the patient's mood state from the patient's baseline state and/or from the patient's mood state following therapy delivery according to the tested therapy program.

Figure 16:
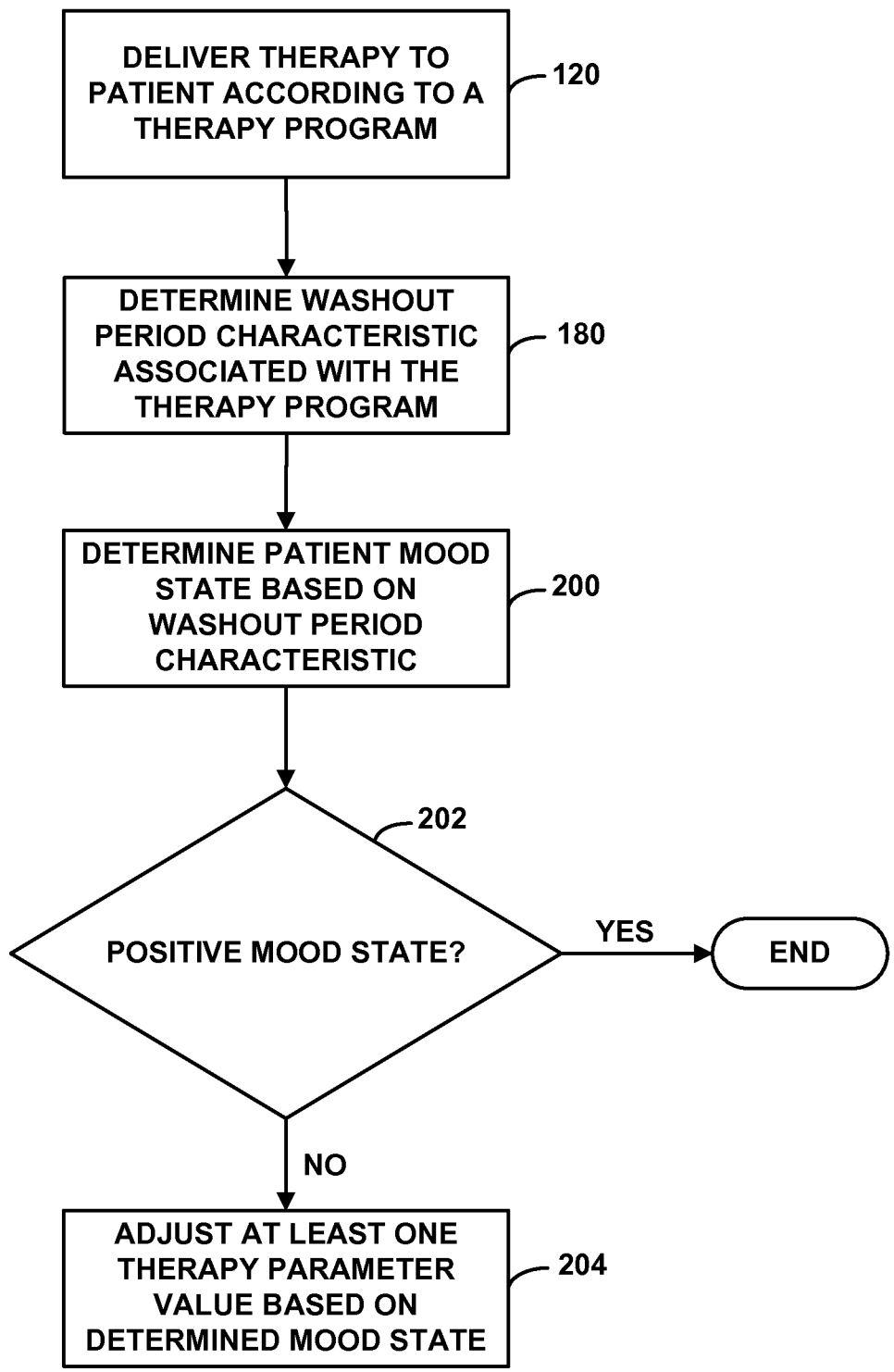
FIG. 16 is a flow diagram illustrating an example technique for adjusting a therapy program based on a patient mood state.

FIG. 16 is a flow diagram illustrating an embodiment of a technique for adjusting a therapy program based on a patient mood state generated in response to therapy delivery according to the therapy program. Processor 70 may control therapy delivery to patient 14 according to a therapy program (120) and determine a washout period characteristic associated with the therapy program (180), e.g., using the technique described above with respect to FIG. 8. Processor 70 may determine a patient mood state based on the washout period characteristic (200), e.g., using the techniques described with respect to FIGS. 12, 14, and 15.

Processor 70 may determine whether the determined patient mood state is a positive mood state (202). For example, if patient 14 has a MDD and therapy system 10 provides therapy to improve the patient's depressive mood, a positive mood state would be a relatively less depressed mood state than the patient's baseline mood state. Alternatively, the positive mood state may be an objectively positive mood state, rather than a relatively positive mood state. For example, although a moderately depressed mood state may be an improvement on the patient's baseline mood state, the clinician may determine that the moderately depressed mood state is not a positive mood state, but rather, a substantially non-depressed mood state is a positive mood state.

If processor 70 determines that the washout period characteristic indicates a positive mood state (202), processor 70 may consider the therapy program efficacious and may not take any action to modify the therapy program. On the other hand, if processor 70 determines that the washout period characteristic does not indicate a positive mood state (202), processor 70 may adjust at least one therapy parameter value of the therapy program based on the determined mood state (204). Processor 70 may modify the therapy program to help improve the patient mood state resulting from therapy delivery according to the therapy program, e.g., to make the therapy delivery more efficacious. Processor 70 may modify the therapy program using any suitable technique, such as the tree-based technique or the genetic algorithm technique described above with respect to FIG. 16. In some cases, the technique shown in FIG. 16 may be used in a closed-loop therapy system to modify a therapy program during chronic therapy delivery, e.g., after a trial session in which efficacious therapy parameter values are titrated.

Many therapy systems 10 used to provide stimulation therapy to patient 14 to manage a psychiatric disorder provide substantially continuous delivery of stimulation to patient 14. One drawback with the continuous stimulation approach is the inefficient use of power. For example, with continuous delivery, therapy may be provided to patient 14 even though patient 14 does not need the therapy. Therapy may be unnecessary or undesired when patient 14 is in a positive mood state. A positive mood state may be a relatively positive mood state, such as an improvement on the patient's baseline mood state (e.g., a moderately depressed mood state compared to a baseline state of severe depression), or may be an objectively positive mood state, such as a non-depressed or non-anxious mood state. Accordingly, a negative mood state may be a relatively negative mood state, such as mood state worse than the patient's baseline mood state (e.g., a severely depressed mood state compared to a baseline state of moderate depression), or may be an objectively negative mood state, such as a state of severe depression or severe anxiousness.

Information associating a patient mood state with a washout period characteristic may be useful for controlling the delivery of therapy. In one embodiment, a physiological parameter of patient 14 may be monitored and a response of the physiological parameter to the delivery of psychiatric disorder therapy may be used to cycle IMD 16 between an active delivery state ("on" state) and a sleep or off state, during which IMD 16 does not deliver therapy to patient 14. The physiological parameter of the patient may, therefore, be monitored to provide "on demand" therapy to patient 14. In particular, a patient mood state may be determined based on the physiological parameter, such as by determining a patient mood state associated with a washout period characteristic that indicates a physiological parameter value or trend. The therapy delivery may then be controlled based on the determined patient mood state.

The physiological parameter of patient 14 that is monitored for the closed-loop control of therapy system 10 may be a parameter that is indicative of the patient's mood state, such as a heart rate, respiratory rate, electrodermal activity, thermal activity or muscle activity (e.g., facial EMG). A physiological parameter characteristic, such as a trend or amplitude value of a physiological signal measuring the activity of the physiological parameter, may be associated with a patient mood state using any suitable technique, such as the one described above with respect to FIG. 11. The information associating a patient mood state with a physiological parameter characteristic may be based specific to patient 14 or may be general to two more patients.

The techniques shown in FIGS. 12, 14, and 15 may also be used to determine the efficacy of a therapy program or to determine the relatively efficacy of a plurality of therapy programs based on a patient mood state during delivery of therapy according to the therapy programs using the technique described with respect to FIG. 16. However, rather than determining a washout period characteristic, processor 70 or another processor may determine a characteristic of a physiological signal during a stimulation period, and determine a patient mood state based on the stimulation period characteristic.

Figure 17:
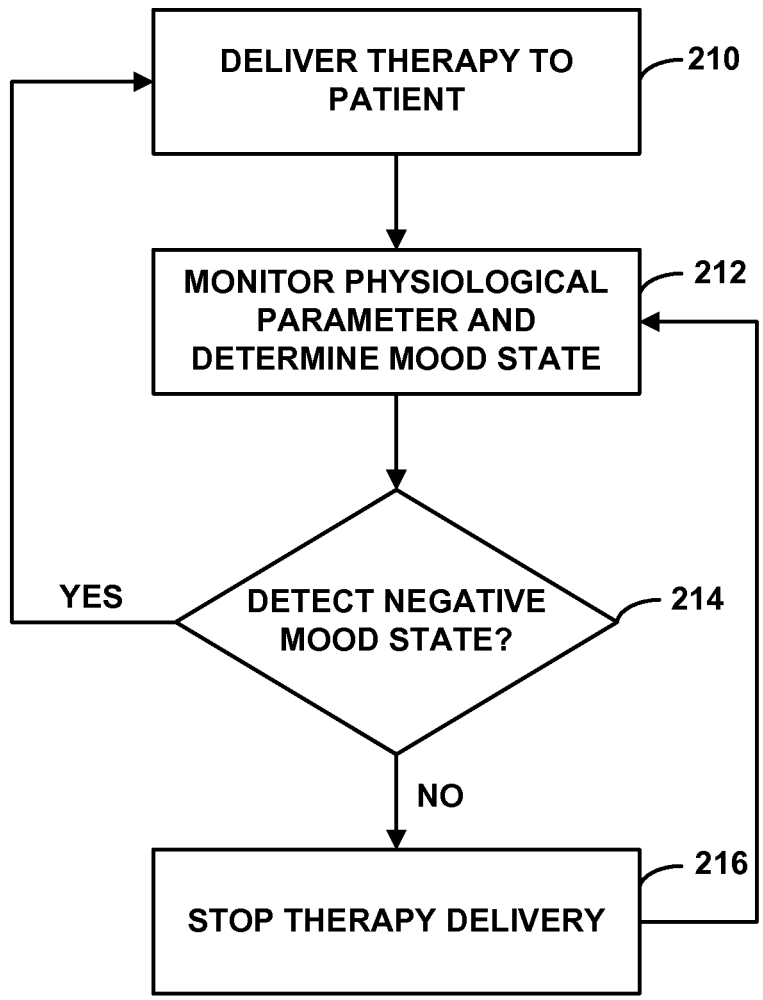
FIGS. 17 and 18 are flow diagrams illustrating example techniques for controlling the delivery of therapy based on a patient mood state.

FIG. 17 is a flow diagram illustrating an embodiment of a technique for controlling the delivery of therapy to patient 14 based on a patient mood state. While processor 34 (FIG. 2) of IMD 16 is primarily referred to throughout the description of FIGS. 17 and 18, in other embodiments, a processor of another device, such as clinician programmer 22 or patient programmer 24 may perform any part of the technique shown in FIGS. 17 and 18. Processor 34 may control therapy module 32 to deliver therapy to patient 14 (210) according to one or more therapy programs that have been determined to provide efficacious therapy to patient 14. The therapy program may be selected using any of the techniques above, such as based a technique that evaluates therapy programs based on a washout period characteristic alone or in combination with other evaluation metrics.

Processor 34 may monitor a physiological parameter of patient and determine a mood state of patient based on the monitored parameter (212) as therapy is actively delivered, e.g., as electrical stimulation signals are delivered to patient 14. For example, processor 34 may monitor a physiological parameter of patient 14, e.g., via signals provided by sensor 26 (FIG. 1) or signals provided by sensors on leads 20 or on a housing of IMD 16. The physiological parameter may be at least one of a respiratory rate, electrodermal activity, thermal activity or muscle activity of patient 14, which may be a surrogate marker for a mood state of patient 14. In addition, in some examples, the physiological parameter may include a brain signal (e.g., an EEG or ECoG) in addition to the respiratory rate, electrodermal activity, thermal activity or muscle activity.

Processor 34 may compare the physiological signal to one or more thresholds or templates in order to determine a mood state, e.g., using techniques similar to those described with respect to FIGS. 12, 14, and 15. Processor 34 may determine the patient mood state at periodic intervals, such as about every one second to every one minute or more. Processor 34 may determine a specific mood state of patient 14, such as a severely depressed mood state, moderately depressed mood state, and the like. Processor 34 may determine the mood state from among a plurality of stored mood states, where each mood state is associated with a physiological signal characteristic in memory 35 of IMD 16 or a memory of another device.

If processor 34 detects a negative mood state (214), processor 34 may continue delivering therapy to patient (210). Processor 34 may detect a negative mood state, e.g., by comparing the determined mood state with a baseline mood state, which may be stored in memory 42. As previously indicated, the baseline mood state may be a mood state of patient 14 prior to any therapy delivery by therapy system 10. Alternatively, processor 34 may automatically determine that predetermined mood states are negative, regardless of the patient's baseline mood state. For example, processor 34 may determine the mood state of patient 14 indicated by the sensed physiological signal by comparing a characteristic of the sensed signal to a plurality of stored templates or threshold values that are each associated with different mood states. If the determined mood state is indicated as being a negative mood state in memory 35, processor 34 may control therapy module 32 to continue delivery therapy to patient 14.

In some embodiments, processor 34 may also modify the therapy program based on the detected mood state. For example, processor 34 may modify the therapy program if processor 34 determines that the current therapy program is insufficiently efficacious, e.g., based on past detection of negative mood states. In one embodiment, processor 34 may track the number of times a negative mood state is detected during the delivery of therapy according to the therapy program and compare the total number of negative mood states or a number of mood states within a particular subset of time to a threshold value.

As another example, processor 34 may determine that the current therapy program is insufficiently efficacious and modify the therapy program if processor 34 determines that the patient mood state has worsened. For example, processor 34 may order stored mood states based on severity of mood states, and determine that the patient mood state has worsened based on the change between the mood states. In this way, determining which of a plurality of stored mood states the physiological parameter of patient 14 indicates may be useful for distinguishing between patient mood states. Different therapy parameter values may be more efficacious for different patient mood states. Thus, an ability to determine different mood states of patient 14 based on a physiological parameter may help provide patient 14 with efficacious psychiatric disorder therapy.

In some embodiments, processor 34 may also receive input from patient 14 indicating a mood state. For example, when patient 14 feels a negative mood state, patient 14 may interact with user interface 44 of patient programmer 24 (FIG. 3), such as by pressing a button dedicated to indicating a negative mood state or by a multi-function button or other user input mechanism. In some embodiments, processor 34 may determine the patient mood state based on both the physiological signal and the patient input. Processor 34 may apply equal weights or different weights to the physiological signal and the patient input. Processor 34 may dynamically change the weight applied to the patient input and physiological signal over time.

If processor 34 does not detect a negative mood state (214), processor 34 may control therapy module 32 to stop therapy delivery (216). Processor 34 may then continue monitoring the physiological parameter and determining the associated mood state (212) until a negative mood state is detected (214), at which time processor 34 may initiate the delivery of therapy to patient 14 (210). In the technique shown in FIG. 17, IMD 16 substantially continuously delivers stimulation therapy to patient 14 until a negative mood state is not detected. Alternatively, IMD 16 may substantially continuously deliver stimulation therapy to patient 14 until a positive mood state is detected.

Figure 18:
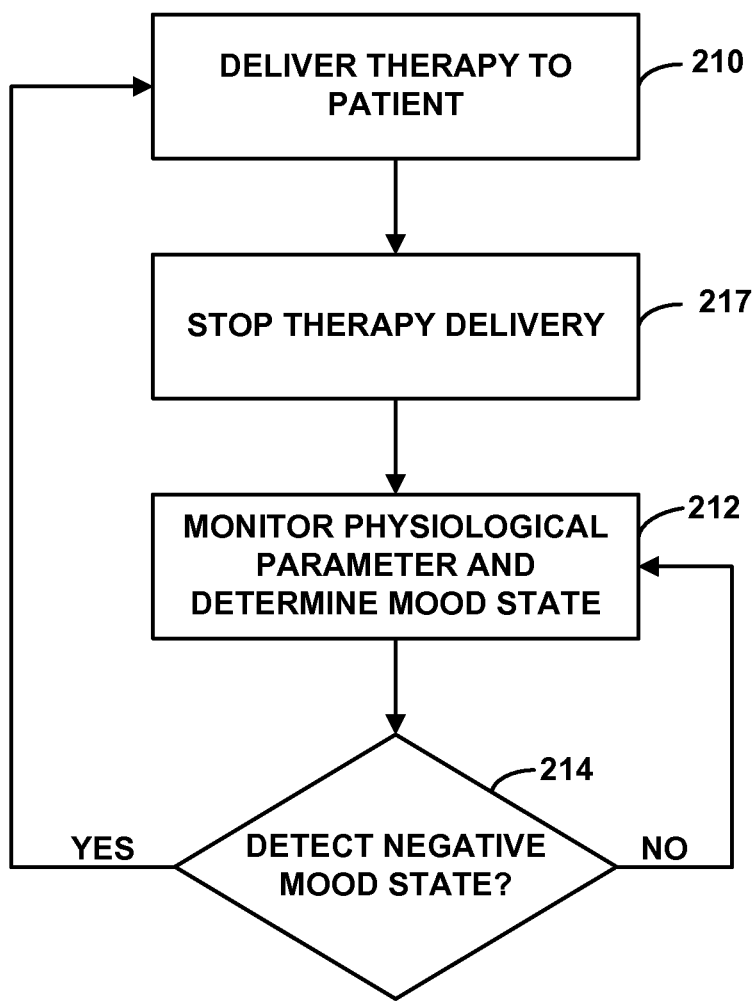

FIG. 18 is a flow diagram illustrating another embodiment of a technique for controlling the delivery of therapy to patient 14 based on a patient mood state. Processor 34 may control therapy module 32 to deliver therapy to patient 14 according to one or more therapy programs determined to provide efficacious therapy to patient 14 (210). Processor 34 may control therapy module 32 to deliver the therapy for a limited period of time, rather than substantially continuously. For example, processor 34 may control therapy module 32 to deliver therapy for about a few seconds to one minute or more (i.e., an "on-cycle") Thereafter, processor 34 may control therapy module 32 to stop therapy delivery (217). After therapy delivery has been stopped, i.e., during an off-cycle of the therapy, processor 34 may monitor a physiological parameter of patient to determine which patient mood state from among a plurality of stored mood states the physiological parameter indicates (212). Again, processor 34 may use any of the techniques described above with respect to FIGS. 12, 14, and 15 to associate a mood state with a monitored physiological signal and determine a mood state. In some embodiments, processor 34 may also receive input from patient 14 indicating a mood state, as described above with respect to FIG. 17.

If processor 34 detects a negative mood state (214) during the post-stimulation period, processor 34 may initiate therapy delivery to patient 14 (210). The frequency at which processor 34 determines the patient's mood state may be selected such that processor 34 detects a negative mood state relatively quickly (e.g., within less than a minute), thereby enabling processor 34 to deliver responsive therapy to the change in the patient's mood state. In some embodiments, processor 34 may also modify the therapy program if processor 34 determines that the current therapy program is not efficacious. If processor 34 does not detect a negative mood state (214) during the post-stimulation period, therapy module 32 may remain in the off-cycle and processor 34 may continue monitoring the physiological signal (212) until a negative mood state is detected, i.e., until a physiological signal of patient 14 indicates that therapy delivery is desirable.

If sensing module 26 or other physiological parameter monitoring systems fail, processor 34 may automatically switch to a particular on-cycle and off-cycle based on a history of the patient's response to therapy. For example, processor 34 may determine that based on the past on-cycle and off-cycle durations, therapy module 32 remained off after a therapy on-cycle for about 20 hours (which is used merely as an example), at which time a negative mood state was detected and therapy module 32 was shifted back to the on-cycle. Accordingly, in the event that sensor 26 fails, processor 34 may control therapy module 32 to deliver therapy to patient 14 with on-cycles separated by an approximately 20 hour off-cycle. In other embodiments, if sensing module 26 or other physiological parameter monitoring systems fail, the processor 34 may also be default such that therapy module 32 delivers therapy in a continuous stimulation or open loop mode.

In addition, in some embodiments, if processor 34 determines that patient 14 provides a substantially consistent response to therapy delivery over a period of time, such as three months to 12 months, such that therapy module 32 delivers therapy to patient 14 with a substantially consistent off-cycle between therapy delivery, processor 34 may control sensor 26 to shut down or enter a sleep mode (a low power mode) to conserve energy. In this way, therapy system 10 may convert to an open-loop therapy system.

The therapy delivery techniques described with respect to FIGS. 17 and 18 may provide a dynamic on/off cycle for therapy delivery to patient 14. In addition, the therapy delivery techniques described with respect to FIGS. 17 and 18 may help reduce the possibility or speed at which patient 14 adapts to the therapy. It has also been found that patient 14 may adapt to DBS provided by IMD 16 over time. That is, a certain level of electrical stimulation provided to brain 12 may be less effective over time. This phenomenon may be referred to as "adaptation." As a result, any beneficial effects to patient 14 from the DBS may decrease over time. While the electrical stimulation levels (e.g., amplitude of the electrical stimulation signal) may be increased to overcome such adaptation, the increase in stimulation levels may consume more power, and may eventually reach undesirable or harmful levels of stimulation.

Figure 19:
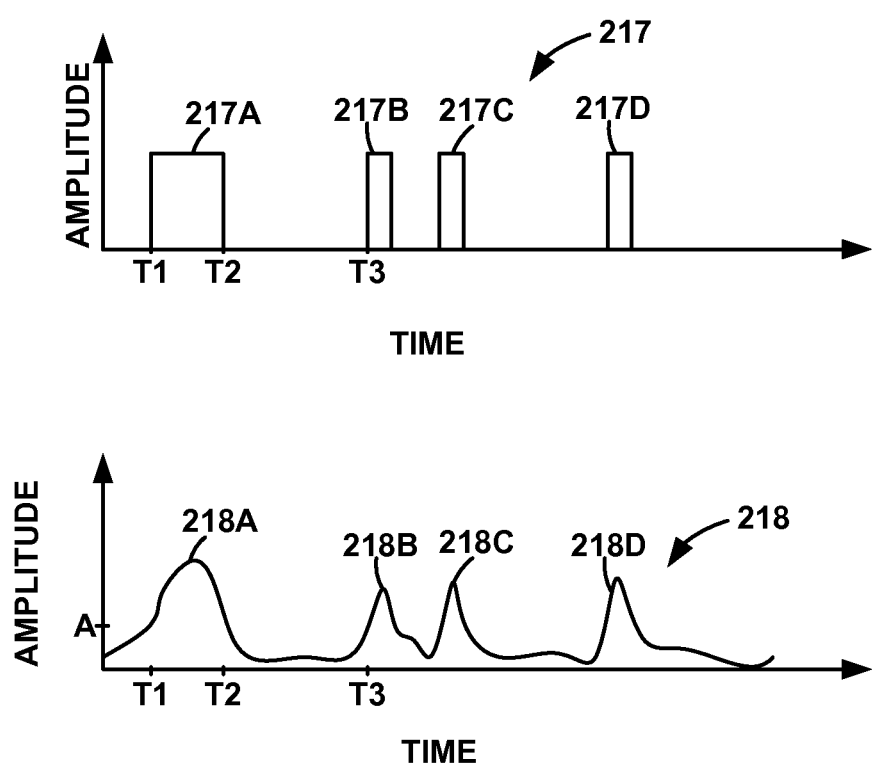
FIG. 19 is a conceptual diagram illustrating the relationship between a physiological signal and stimulation signals.

FIG. 19 is a conceptual diagram illustrating a stimulation signal 217 delivered by IMD 16 to a target tissue site within patient 14 and a corresponding physiological signal 218. Processor 34 may receive physiological signal 218 from sensor 26 or from a sensing module within IMD 16. Physiological signal 218 may be received from a separate sensor 26 via a wired or wireless connection. Processor 34 may determine a patient mood state based on physiological signal 218. In the embodiment shown in FIG. 19, processor 34 detects a negative patient mood state when the amplitude of physiological signal 218 crosses amplitude threshold A.

In accordance with the technique shown in either FIG. 17 or 18, processor 34 may continue delivering therapy or resume therapy when the amplitude of physiological signal 218 crosses (e.g., is greater than or equal to) threshold A. As shown in FIG. 19, stimulation signal 217 indicates therapy is delivered to patient 14, as reflected by a higher waveform amplitude, when physiological signal 218 crosses threshold A. Processor 34 controls IMD 16 to deliver therapy to patient 14 as long as physiological signal 218 indicates patient 14 is in a negative mood state or otherwise not in a positive mood state. Thus, in a first instance, the portion of stimulation signal 217A that indicates IMD 16 was delivering active stimulation to patient 14 temporally correlates with the portion of physiological signal 218A, which has an amplitude at or above threshold T.

Processor 34 controls therapy module 32 to being delivering therapy to patient 14 at time T1. Upon determining an amplitude of physiological signal 218 is below threshold A, at time T2, processor 34 may control therapy module 32 to stop therapy delivery or at least decrease the intensity of the therapy. Processor 34 may continue monitoring physiological signal 218 to determine when signal 218 suggest patient 14 is experiencing a negative mood state.

At time T3, processor 34 may determine that the amplitude of physiological signal is greater than or equal to threshold A, and initiate therapy delivery, as indicated by portion 217B of stimulation signal 217. Therapy is delivered until processor 34 determines an amplitude of physiological signal 218 no longer indicates patient 14 is in the negative mood state, e.g., in the example shown in FIG. 19, the amplitude of physiological signal 218 falls below threshold A. Thus, stimulation signal portion 217B corresponds temporally to physiological signal portion 218B. Similarly, stimulation signal portions 217C, 217D temporally correlate to physiological signal portions 218C, 218D, respectively.

FIG. 19 is merely a conceptual diagram of an example of a stimulation signal 217 and physiological signal 218. In other embodiments, other characteristics of physiological signal 218 may control therapy delivery, and in other embodiments, stimulation signal 217 may not include pulses, but rather continuous wave signals. Similarly, other relationships between a stimulation signal and physiological signal are contemplated and may be specific to the type of physiological signal monitored and the type of washout period or stimulation period characteristic used to associate a patient mood state with a physiological signal characteristic.

Figure 20:
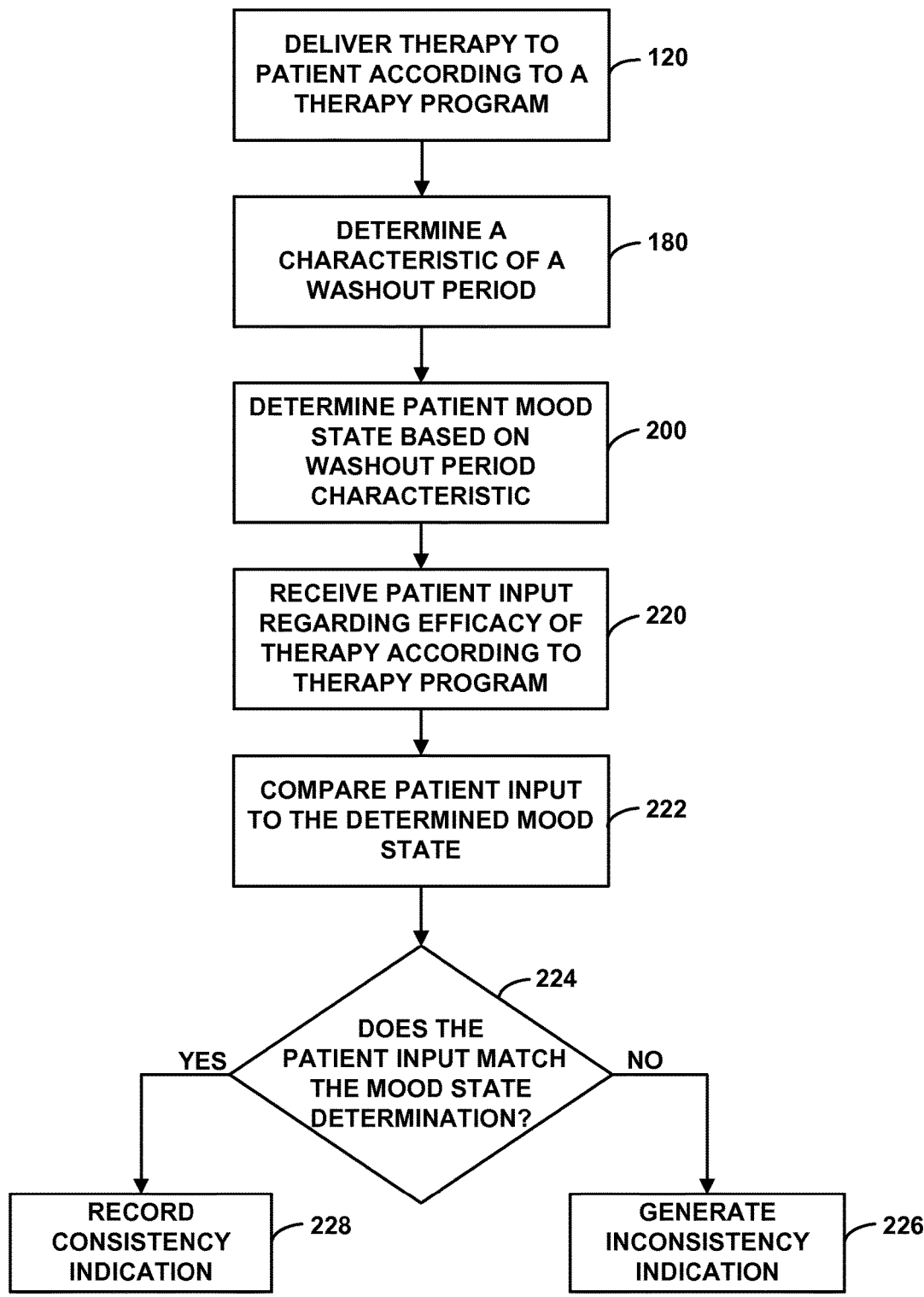
FIG. 20 is a flow diagram illustrating an example technique for determining whether patient input indicating a mood state and a mood state determined based on a physiological signal are consistent.

As previously described, a washout period characteristic or stimulation period characteristic may be compared to patient input regarding the efficacy of a tested therapy program, such as to determine whether the patient input and is consistent with the washout period characteristic. In some cases, a washout period characteristic or stimulation period characteristic may be used to validate patient input regarding the efficacy of a tested therapy program, such as to determine whether the patient input is consistent with relatively objective indicia, such as a washout period characteristic. FIG. 20 is a flow diagram illustrating an example embodiment of a technique for comparing patient feedback to therapy delivery according to a therapy program to information determined based on a washout period characteristic. The technique shown in FIG. 20 may also be used to compare patient feedback to therapy delivery according to a therapy program to information determined based on a stimulation period characteristic.

The patient feedback may be received, e.g., during a trial therapy session in which the therapy program is tested for relative efficacy in managing the patient's psychiatric disorder and minimizing side effects from the therapy delivery. In other embodiments, determining whether patient input regarding the efficacy of a therapy program matches information determined based on a washout period characteristic may be applicable to therapy programs for other therapeutic applications, including other DBS therapies, SCS therapies, peripheral nerve stimulation, and the like. While the description of FIG. 20 primarily refers to processor 70 of clinician programmer 22, in other embodiments, processor 34 of IMD 16, processor 40 of patient programmer 24 or a processor of another device may implement the technique shown in FIG. 20, alone or in combination with processor 70.

Processor 70 may control IMD 16 to deliver therapy to patient 14 according to a therapy program (120), and processor 70 may determine a characteristic of a washout period resulting from the therapy delivery, e.g., using the technique described above with respect to FIG. 8 (180). Processor 70 may determine a patient mood state based on the washout period characteristic (200), which may be a probability of the mood state based on previous data acquired from patient 14 or a plurality of patients. Processor 70 may receive input from patient 14 indicating the efficacy of the therapy delivered according to the therapy program (220). For example, processor 70 may prompt the clinician or patient 14 to input information via user interface 74 (FIG. 4). The information may be, for example, an overall rating of efficacy, a rating of the therapeutic benefits, a rating of the side effects, and the like. The rating information may, but need not be, based on a numerical rating scale or may be determine based on the patient's answer to one or more questions. In some embodiments, the rating information may merely be textual notes inputted by the clinician or patient 14.

Processor 70 may compare the patient input regarding efficacy to the mood state determined based on the washout period characteristic (222) and determine whether the patient input and mood state determination match (224), e.g., whether the patient input and determined mood state are consistent. For example, processor 70 may determine whether the washout period characteristic is associated with a positive patient mood state, which as previously described may be an objectively positive mood state, such as a non-depressive mood state, or may merely be an improvement from the patient's baseline mood state, and whether the patient's input also indicates a positive mood state. If the mood state determined based on the washout period characteristic is a positive mood state, and patient 14 indicates that the therapy delivery according to the therapy program did not provide any beneficial results, processor 70 may determine that the patient input and determined mood state are inconsistent (224).

Similarly, if the mood state determined based on the washout period characteristic is a negative mood state, which may be an objectively negative mood state, such as severe depressive mood state, or may be a degradation in the patient's baseline state, such as a change from a moderate depressive mood state to a severe depressive mood state, and patient 14 provides input indicating that the therapy delivery according to the therapy program provided beneficial results, processor 70 may determine that the patient input and the mood state determined based on the washout period characteristic are inconsistent (224).

Processor 70 may record an inconsistency indication in memory 72 (FIG. 4) that indicates that the patient input in response to the test therapy delivery according to the therapy program was inconsistent with the mood state determined based on the washout period characteristic (226). The inconsistency indication may be, for example, a value, flag or signal that is stored in memory 72 (FIG. 4) of clinician programmer 22 and associated with the therapy program. The clinician may review the recorded information, and, if desired, retest the therapy program may by delivering therapy according to the therapy program. In some cases, processor 70 may automatically retest the therapy program by controlling IMD 16 to deliver therapy according to the therapy program in a subsequent trial, which may, but need not, immediately follow the prior trial therapy delivery according to the therapy program. In other embodiments, processor 70 may generate a prompt and receive clinician approval prior to retesting the therapy program.

In some cases, if the patient input and mood state determination are inconsistent, the clinician may determine whether the washout period characteristic or the patient input is entitled to more weight with respect to evaluating the therapy program. For example, the clinician may determine that patient 14 has provided inconsistent, inaccurate or untruthful responses in the past, and, therefore, attribute more weight to the mood state determination based on the washout period characteristic. The clinician may provide input to programmer 22 indicating whether the patient input or washout period characteristic is entitled to more weight. If the clinician selects the washout period characteristic as the more reliable indicia of patient mood and the patient input and mood state determination are inconsistent, processor 70 may determine that the patient input was invalid (or entitled to less weight) due to its inconsistency with the mood state determined based on the washout period characteristic. On the other hand, if the clinician selects the patient input as the more reliable indicia of patient mood and the patient input and mood state determination are inconsistent, processor 70 may determine that the mood state determination based on a washout period characteristic was invalid (or entitled to less weight) due to its inconsistency with the mood state determined based on the patient input.

Processor 70 may generate a notification to the clinician that the patient input was inconsistent with the determined mood state. In some embodiments, processor 70 may prompt patient 14 to input more detailed information evaluating the efficacy of the therapy program. Processor 70 may determine, for example, whether patient 14 provided input that was inconsistent with the determined patient mood state because the therapy delivery according to the therapy program resulted in a positive mood state, but also generated side effects that patient 14 deemed to render the therapy program unacceptable, e.g., subjectively non-efficacious.

If the mood state determined based on the washout period characteristic and the patient input are consistent, e.g., match (224), processor 70 may record a consistency indication in memory 72 and associate the input with the therapy program (228). The therapy program may be implemented for chronic therapy delivery or may be retested at a later time. Processor 70 may determine that the patient input is consistent with the mood state determined based on the washout period characteristic if the mood state determined based on the washout period characteristic is a positive mood state, and patient 14 indicates that the therapy delivery according to the therapy program provided beneficial results. Similarly, processor 70 may determine that the patient input is consistent with the mood state determined based on the washout period characteristic if the mood state determined based on the washout period characteristic is a negative mood state, and patient 14 indicates that the therapy delivery according to the therapy program did not provide beneficial results.

After testing a plurality of therapy programs and associating each tested therapy program with consistency or inconsistency indications, the clinician may evaluate the therapy programs based on the consistency or inconsistency indications. For example, processor 70 may order the list of therapy programs according to the consistency or inconsistency indications in order to allow the clinician to relatively quickly discern which therapy programs resulted in consistent mood state determinations based on a washout period characteristic and patient input. In some examples, processor 70 may order the list of therapy programs according to the consistency or inconsistency indications. For example, processor 70 may order the list of therapy programs according to the total number of consistency or inconsistency indications associated with the therapy programs, or according to a percentage that represents the percentage of trials that the patient's input matched the mood state determined based on the physiological signal (e.g., the washout period characteristic or a stimulation period characteristic).

If, for example, 3 out of 5 trials of a therapy program (e.g., testing for a limited period of time) resulted in a match between the patient input and mood state, such that 3 consistency indications and 2 inconsistency indications are associated with the therapy program, the match percentage associated with the therapy program may be about 60% and the non-match percentage may be about 40%. The list of tested therapy programs may be ordered upon receiving instructions from clinician indicating the list of therapy programs should be ordered according to the consistency or inconsistency indications. In some cases, the consistency and inconsistency indications may be a part of an overall metric for evaluating therapy programs, such as the overall metric described above with respect to FIG. 9.

Evaluating a list of therapy programs based on whether the therapy programs resulted in consistent patient input indicating a mood state and mood state determination based on a washout period characteristic may be useful for increasing the clinician's confidence about the efficacy of a therapy program. For example, if a therapy program is tested one or more times and has a relatively low match rate (e.g., in terms of percentage of matches for two or more trials), as indicated by the number of consistency or inconsistency indications associated with the therapy program, the clinician may determine that the therapy program is not as efficacious as another therapy program that has a relatively high match rate. In addition, the consistency or inconsistency indications associated with the therapy programs may be useful for differentiating between two therapy programs that are associated with relatively similar patient efficacy inputs.

The technique shown in FIG. 20 may be performed after a washout period characteristic of a physiological signal has been associated with a patient mood state, as described with respect to FIG. 11. In other embodiments, the technique shown in FIG. 20 may be performed without associating washout period characteristics with a patient mood state. For example, activity of a physiological signal during a post-stimulation period may indicate the therapy delivery according to the therapy program resulted in a detectable physiological effect on patient 14. Accordingly, if patient 14 provides input stating that the therapy delivery according to the therapy program did not have any effect, therapeutic or not, on patient 14, the clinician may evaluate the therapy program based on whether the patient's input matches information gained from the physiological signal during the post-stimulation period, which may be automatically detected.

As an example, if the clinician notices a relatively large change in a signal indicating the heart rate of patient 14, but the patient provides input indicating that no physiological effect was felt, the clinician may determine that the therapy program provided inconsistent physiological signal morphology and patient input. The clinician may then apply less weight to the therapy program associated with the inconsistent patient input and physiological effects when selecting therapy programs to implement for chronic therapy delivery for patient 14. In some cases, the inconsistency between the activity of physiological signal during the post-stimulation period, indicating a carryover effect, and the patient's input may prompt the clinician to retest the therapy program.

While the description primarily refers to electrical stimulation therapy, in some cases, a characteristic of a washout period following the delivery of a therapeutic agent to patient 14 may be determined. Just as with the therapy systems 10 described above, for a therapy system that includes delivery of a therapeutic agent, one or more physiological parameters of patient 14 may be monitored in order to detect the washout period and determine a washout period characteristic, such as a brain activity, heart rate, respiratory rate, electrodermal activity, facial electromyogram or thermal activity of the patient's body.

In the case of therapeutic agent delivery, the therapy parameters may include the dosage of the therapeutic agent (e.g., a bolus size or concentration), the rate of delivery of the therapeutic agent, the maximum acceptable dose in each bolus, a time interval at which a dose of the therapeutic agent may be delivered to a patient (lock-out interval), and so forth. Example therapeutic agents include, but are not limited to, selective serotonin reuptake inhibitor drugs, amitriptyline, amoxapine, benzodiazepines, bupropion, clomipramine, desipramine, doxepin, imipramine, monoamine oxidase inhibitors, maprotiline, mirtazapine, nefazodone, nortriptyline, protriptyline, trazodone, trimipramine, venlafaxines to manage OCD, anxiety disorders or MDD; alprazolam, buspirone, chlordiazepoxide, clonazepam, diazepam, halazepam, lorazepam, oxazepam, prazepam to manage anxiety disorders; and carbamazepine, depakote, divalproex sodium (valproic acid), gabapentin, lamotrigine, lithium carbonate, lithium citrate or topimarate to manage bipolar disorder.

The disclosure also contemplates computer-readable media comprising instructions to cause a processor to perform any of the functions described herein. The computer-readable media may take the form of any volatile, non-volatile, magnetic, optical, or electrical media, such as a RAM, ROM, NVRAM, EEPROM, flash memory, or any other digital media. A programmer, such as clinician programmer 22 or patient programmer 24, may also contain a more portable removable memory type to enable easy data transfer or offline data analysis.

The techniques described in this disclosure, including those attributed to IMD 16, programmers 22, 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 40 of IMD 16 and/or processor 60 of programmer 14, any one or more parts of the techniques described herein may be implemented by a processor of one of IMD 16, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Many embodiments of the disclosure have been described. Various modifications may be made without departing from the scope of the claims. These and other embodiments are within the scope of the following claims.

The invention claimed is:

1. A method comprising:
monitoring a signal indicative of a physiological parameter of a patient during and after a first period during which therapy according to a first therapy program is delivered to the patient;
determining, with a processor, a characteristic of a washout period based on the signal monitored after the first period, wherein the washout period follows the first period, and wherein a carryover effect from the delivery of the therapy according to the first therapy program substantially dissipates during the washout period;
determining, with the processor and based on the characteristic of the washout period, a time at which to deliver therapy to the patient according to a second therapy program; and
automatically initiating the delivery of therapy to the patient according to the second therapy program at the time determined based on the characteristic of the washout period.

2. The method of claim 1, wherein the signal indicative of the physiological parameter comprises a first signal indicative of a first physiological parameter of the patient, the method further comprising monitoring a second signal indicative of a second physiological parameter of the patient during and after the first period, wherein determining the characteristic of the washout period comprises determining the characteristic of the washout period based on the first and second signals monitored after the first period.

3. The method of claim 1, wherein the characteristic of the washout period indicates an end of the washout period, and wherein the time determined based on the characteristic of the washout period is at the end of the washout period or after the end of the washout period.

4. The method of claim 1, wherein determining the characteristic of the washout period based on the signal monitored after the first period comprises detecting a change in the signal from a baseline state of the signal during a second period following the first period.

5. The method of claim 4, wherein determining the characteristic of the washout period based on the signal comprises determining when the signal returns to the baseline state during the second period, and wherein determining the time based on the characteristic of the washout period comprises determining the time at which the signal returned to the baseline state during the second period.

6. The method of claim 4, wherein determining the characteristic of the washout period based on the signal comprises determining when the signal returns to the baseline state during the second period, the method further comprising, after determining when the signal returns to the baseline state during the second period, determining whether a minimum waiting period has expired following the first period, wherein determining the time based on the characteristic of the washout period comprises determining the time as the later of a first time at which the signal returned to the baseline state during the second period or a second time at which the minimum waiting period has expired.

7. The method of claim 6, further comprising applying a stimulus to decrease a duration of the washout period.

8. The method of claim 4, wherein the signal indicative of the physiological parameter comprises a first signal indicative of a first physiological parameter of the patient, the change in the first signal from a baseline state comprises a first change in the first signal from a first baseline state of the first signal, the method further comprising monitoring a second signal indicative of a second physiological parameter of the patient, wherein determining the characteristic of the washout period based on the signal comprises detecting the first change in the first signal from the first baseline state during the second period, and detecting a second change in the second signal from a second baseline state of the second signal during the second period.

9. The method of claim 8, wherein determining the characteristic of the washout period based on the signal comprises determining when the first signal returns to the first baseline state during the second period and when the second signal returns to the second baseline state during the second period, and wherein determining the time based on the characteristic of the washout period comprises determining the time at which the first signal returned to the first baseline state and the second signal returned to the second baseline state during the second period.

10. The method of claim 8, wherein determining the characteristic of the washout period based on the signal comprises determining when the first signal returns to the first baseline state during the second period or when the second signal returns to the second baseline state during the second period, and wherein determining the time based on the characteristic of the washout period comprises determining the time at which either the first signal returned to the first baseline state or the second signal returned to the second baseline state during the second period.

11. The method of claim 1, wherein determining the characteristic of the washout period based on the signal comprises determining when the signal returns to a first state during a second period immediately following the first period.

12. The method of claim 11, further comprising determining the first state prior to delivery of the therapy according to the first therapy program.

13. The method of claim 11, wherein the carryover effect comprises a first carryover effect, the signal comprises a first signal, the characteristic comprises a first characteristic, the washout period comprises a first washout period, and the time comprises a first time, the method further comprising:
monitoring a second signal indicative of the physiological parameter of the patient during and after a third period during which therapy according to the second therapy program is delivered to the patient;
determining a second characteristic of a second washout period based on the second signal monitored after the third period, wherein the second washout period follows the third period, and wherein a second carryover effect from the delivery of therapy according to the second program substantially dissipates during the second washout period;
determining, based on the second characteristic of the second washout period, a second time at which to deliver therapy to the patient according to a third therapy program; and
automatically initiating delivery of therapy to the patient according to the third therapy program at the second time determined based on the second characteristic of the second washout period.

14. The method of claim 13, wherein determining the second characteristic of the second washout period based on the second signal comprises determining when the second signal returns to the first state during a fourth period immediately following the third period.

15. The method of claim 13, further comprising determining a second state of the second signal prior to the delivery of therapy according to the second therapy program, wherein determining the second characteristic of the second washout period comprises determining when the second signal returns to the second state during a fourth period immediately following the third period.

16. The method of claim 1, wherein the therapy comprises at least one of electrical stimulation therapy or therapeutic agent delivery therapy.

17. The method of claim 1, wherein the characteristic of the washout period comprises an amplitude of the signal, a power level in a frequency band of the signal, or a ratio of power levels in two or more frequency bands of the signal, the method further comprising:
comparing the amplitude of the signal, the power level in the frequency band of the signal, or the ratio of power levels to a threshold value,
wherein determining the time based on the characteristic of the washout period comprises determining the time based on the comparison of the amplitude of the signal, the power level in the frequency band of the signal, or the ratio of power levels to the threshold value.

18. The method of claim 17, wherein comparing the amplitude of the signal, the power level in the frequency band of the signal, or the ratio of power levels to the threshold value comprises comparing the amplitude to the threshold value by at least comparing at least one of a peak amplitude, average amplitude or median amplitude of the signal during a sample period to the threshold value.

19. The method of claim 17, wherein determining the time based on the characteristic of the washout period comprises determining the time at which the amplitude of the signal has fallen to or below the threshold value.

20. The method of claim 1, wherein the characteristic of the washout period comprises a trend in the signal, and wherein determining the time based on the characteristic of the washout period comprises comparing the trend in the signal to a template and determining the time based on the comparison.

21. The method of claim 1, further comprising applying a stimulus to decrease a duration of the washout period.

22. The method of claim 1, wherein monitoring the signal comprises monitoring a signal indicative of at least one of a heart rate, respiratory rate, electrodermal activity, facial electromyogram or thermal activity of the patient.

23. The method of claim 1, wherein automatically initiating the delivery of therapy to the patient according to the second therapy program comprises generating an indication to a user to notify the user of the delivery of therapy or to seek approval prior to delivery of the therapy according to the second therapy program.

24. The method of claim 1, wherein the therapy is configured to manage a psychiatric condition of the patient, and wherein the second therapy program is selected to improve a mood state of the patient.

25. A method comprising:
determining a baseline state of a physiological signal of a patient;
with a processor, controlling a medical device to deliver electrical stimulation therapy to a patient according to a first therapy program during a predetermined stimulation period;
monitoring the physiological signal of the patient during a post-stimulation period following the stimulation period;
automatically determining, with the processor, a first time during the post-stimulation period at which the physiological signal returns to a first state that is based on the baseline state, based on the monitored physiological signal;

determining, with the processor, a second time during the post-stimulation period at which to deliver therapy to the patient according to a second therapy program based on the first time; and with the processor, automatically controlling the medical device to deliver electrical stimulation therapy to the patient according to a second therapy program at the second time.

26. The method of claim 25, wherein the first state comprises the baseline state.

27. The method of claim 25, further comprising, after determining the first time at which the physiological signal returns to the first state, automatically determining whether a minimum time has passed prior to controlling the medical device to deliver electrical stimulation therapy to the patient according to the second therapy program.

28. A system comprising:
a medical device configured to deliver therapy to the patient according to a first therapy program during a first period;
a sensor configured to generate a signal indicative of a physiological parameter of the patient during and after the first period; and
a processor configured to receive the signal from the sensor, determine a characteristic of a washout period based on the signal monitored after the first period, wherein the washout period follows the first period and wherein a carryover effect from the delivery of the therapy according to the first therapy program substantially dissipates during the washout period, determine, based on the characteristic of the washout period, a time at which to deliver therapy to the patient according to a second therapy program, and automatically control the medical device to deliver the therapy to the patient according to the second therapy program at the time determined based on the characteristic of the washout period.

29. The system of claim 28, wherein the processor is configured to generate an indication to a user to notify the user of the delivery of therapy or to seek approval prior to controlling the medical device to deliver the therapy according to the second therapy program.

30. The system of claim 28, wherein the processor is configured to determine the characteristic of the washout period by at least, during a second period following the first period, detecting a change in the signal from a first state of the signal.

31. The system of claim 30, wherein the first state comprises a baseline state of the signal that is determined prior to the first period.

32. The system of claim 31, wherein the processor is configured to determine the characteristic of the washout period by at least determining when the signal returns to the baseline state during the second period and wherein the time is the time at which the signal returned to the baseline state during the second period.

33. The system of claim 31, wherein the processor is configured to determine the characteristic of the washout period by at least determining when the signal returns to the baseline state during the second period, and, after determining when the signal returns to the baseline state during the second period, determine whether a minimum waiting period has expired following the first period, wherein the processor determines the time based on the characteristic of the washout period by at least determining the time as the later of a first time at which the signal returned to the baseline state during the second period or a second time at which the minimum waiting period has expired.

34. The system of claim 33, wherein the processor is configured to control the medical device to deliver a stimulus to the patient to decrease a duration of the washout period.

35. The system of claim 28, wherein the processor is configured to initiate the delivery of a stimulus to the patient to decrease a duration of the washout period.

36. The system of claim 28, wherein the sensor is configured to generate the signal as a function of at least one of a heart rate, respiratory rate, electrodermal activity, facial electromyogram or thermal activity of the patient.

37. The system of claim 28, wherein the characteristic of the washout period indicates an end of the washout period, and wherein the time determined based on the characteristic of the washout period is at the end of the washout period or after the end of the washout period.

38. The system of claim 28, wherein the characteristic of the washout period comprises an amplitude of the signal, a power level in a frequency band of the signal, or a ratio of power levels in two or more frequency bands of the signal, and wherein the processor is configured to compare the amplitude of the signal, the power level in the frequency band of the signal, or the ratio of power levels to a threshold value, and determine the time based on the characteristic of the washout period by at least determining the time based on the comparison of the amplitude of the signal, the power level in the frequency band of the signal, or the ratio of power levels to the threshold value.

39. The system of claim 28, wherein the therapy is configured to manage a psychiatric condition of the patient, and wherein the processor is configured to select the second therapy program to improve a mood state of the patient.

40. A system comprising:
means for monitoring a signal indicative of a physiological parameter of a patient during and after a first period during which therapy according to a first therapy program is delivered to the patient;
means for determining a characteristic of a washout period based on the signal monitored after the first period, wherein the washout period follows the first period and wherein a carryover effect from the delivery of the therapy according to the first therapy program substantially dissipates during the washout period;
means for determining, based on the characteristic of the washout period, a time at which to deliver therapy to the patient according to a second therapy program; and
means for automatically initiating delivery of the therapy to the patient according to the second therapy program at the time determined based on the characteristic of the washout period.

41. The system of claim 40, further comprising means for applying a stimulus to decrease a duration of the washout period.

* * * * *